US010733866B2

(12) United States Patent
Rabinowitz et al.

(10) Patent No.: US 10,733,866 B2
(45) Date of Patent: Aug. 4, 2020

(54) WALKER-ASSIST DEVICE

(71) Applicants: The Sheba Fund for Health Services and Research, Ramat Gan (IL); Avraham Rabinowitz, Givat Shmuel (IL); Yohana Ram, Gedera (IL)

(72) Inventors: Avraham Rabinowitz, Givat Shmuel (IL); Yohana Ram, Gedera (IL)

(73) Assignees: The Sheba Fund for Health Services and Research, Ramat Gan (IL); Avraham Rabinowitz, Givat Shmuel (IL); Yohana Ram, Gedera (IL)

( * ) Notice: Subject to any disclaimer, the term of this patent is extended or adjusted under 35 U.S.C. 154(b) by 0 days.

(21) Appl. No.: 15/030,874

(22) PCT Filed: Oct. 29, 2014

(86) PCT No.: PCT/IL2014/050935
§ 371 (c)(1),
(2) Date: Apr. 21, 2016

(87) PCT Pub. No.: WO2015/063765
PCT Pub. Date: May 7, 2015

(65) Prior Publication Data
US 2016/0253890 A1    Sep. 1, 2016

Related U.S. Application Data

(60) Provisional application No. 61/896,746, filed on Oct. 29, 2013.

(51) Int. Cl.
G08B 21/04        (2006.01)
G06F 19/00        (2018.01)
(Continued)

(52) U.S. Cl.
CPC ............ *G08B 21/0461* (2013.01); *A45B 3/00* (2013.01); *A45B 3/02* (2013.01); *A45B 3/08* (2013.01);
(Continued)

(58) Field of Classification Search
CPC ......... A61H 3/04; G08B 21/0461; A45B 3/04
See application file for complete search history.

(56) References Cited

U.S. PATENT DOCUMENTS 5,511,571 A * 4/1996 Adrezin ............... A61B 5/1038
135/66
5,853,219 A   12/1998 Santuccio
(Continued)

FOREIGN PATENT DOCUMENTS

WO   WO 2006/014533   2/2006
WO   WO 2006/074029   7/2006
(Continued)

OTHER PUBLICATIONS

Office Action dated Oct. 31, 2016 From the Israel Patent Office Re. Application No. 245207 and Its Translation Into English. (6 Pages).
(Continued)

*Primary Examiner* — Curtis B Odom

(57) ABSTRACT

A system for monitoring the use of a walker comprising: at least one sensor adapted for retrofitting to a walker, for measuring a physical parameter at at least one location on the walker and for sending at least one feedback signal indicating a value of the physical parameter measured.

24 Claims, 44 Drawing Sheets

(51) Int. Cl.

| | |
|---|---|
| A45B 3/02 | (2006.01) |
| A61B 5/11 | (2006.01) |
| A61H 1/02 | (2006.01) |
| A45B 9/00 | (2006.01) |
| A61H 3/04 | (2006.01) |
| A45B 3/00 | (2006.01) |
| A45B 3/08 | (2006.01) |
| A61B 5/22 | (2006.01) |
| A61B 5/103 | (2006.01) |
| A61H 3/02 | (2006.01) |
| A61H 3/00 | (2006.01) |
| G09B 19/24 | (2006.01) |

(52) U.S. Cl.
CPC ............... *A45B 9/00* (2013.01); *A61B 5/103* (2013.01); *A61B 5/112* (2013.01); *A61B 5/1112* (2013.01); *A61B 5/1113* (2013.01); *A61B 5/1116* (2013.01); *A61B 5/225* (2013.01); *A61H 1/02* (2013.01); *A61H 3/00* (2013.01); *A61H 3/02* (2013.01); *A61H 3/04* (2013.01); *G06F 19/3481* (2013.01); *G08B 21/0446* (2013.01); *G09B 19/24* (2013.01); *A61H 2201/0107* (2013.01); *A61H 2201/0184* (2013.01); *A61H 2201/501* (2013.01); *A61H 2201/5043* (2013.01); *A61H 2201/5048* (2013.01); *A61H 2201/5061* (2013.01); *A61H 2201/5084* (2013.01)

(56) References Cited

U.S. PATENT DOCUMENTS

| | | | | |
|---|---|---|---|---|
| 7,963,294 | B1 * | 6/2011 | Trout | A61H 3/00 135/66 |
| 2005/0077345 | A1 | 4/2005 | March | |
| 2006/0183603 | A1 * | 8/2006 | Astilean | A63B 22/0242 482/8 |
| 2006/0206167 | A1 | 9/2006 | Flaherty et al. | |
| 2006/0292533 | A1 | 12/2006 | Selod | |
| 2007/0233403 | A1 * | 10/2007 | Alwan | A61B 5/1038 702/33 |
| 2008/0042853 | A1 | 2/2008 | Dempsey | |
| 2010/0318005 | A1 | 12/2010 | Amonette et al. | |
| 2013/0014790 | A1 * | 1/2013 | Van Gerpen | A61H 3/04 135/66 |
| 2013/0167888 | A1 * | 7/2013 | LoSasso | A63B 71/0622 135/66 |

FOREIGN PATENT DOCUMENTS

| | | |
|---|---|---|
| WO | WO 2008/036782 | 3/2008 |
| WO | WO 2009/070676 | 6/2009 |
| WO | WO 2011/079320 | 6/2011 |
| WO | WO 2015/063765 | 5/2015 |

OTHER PUBLICATIONS

International Preliminary Report on Patentability dated Mar. 13, 2016 From the International Preliminary Examining Authority Re. Application No. PCT/IL2014/050935.
International Search Report and the Written Opinion dated Feb. 17, 2015 From the International Searching Authority Re. Application No. PCT/IL2014/050935.
Alwan et al. "Basic Walker-Assisted Gait Characteristics Derived From Forces and Moments Exerted on the Walker's Handles: Results on Normal Subjects", Medical Engineering & Physics, 29: 380-389, 2007.
Bechly et al. "Determining the Preferred Modality for Real-Time Biofeedback During Balance Training", Gait & Posture, 37: 391-396, 2013.
Cakrt et al. "Balance Rehabilitation Therapy by Tongue Electrotactile Biofeedback in Patients With Degenerative Cerebellar Disease", NeuroRehabilitation, 31: 429-434, 2012.
Fast et al. "The Instrument Walker: Usage Patterns and Forces", Archives of Physical Medicine and Rehabilitation, 76: 484-491, May 1995.
Frizera et al. "The Smart Walkers as Geriatric Assistive Device. THE SIMBIOSIS Purpose", Gerontechnology, 7(2): 108-113, 2008.
Jorgensen et al. "Efficacy of Nintendo Wii Training on Mechanical Leg Muscle Function and Postural Balance in Community-Dwelling Older Adults: A Randomized Controlled Trial", The Journals of Gerontology, Series A: Biological Sciences and Medical Sciences, 68(7): 845-852, Jul. 2013.
Lamoth et al. "Exergaming for Elderly: Effects of Different Types of Game Feedback on Performance of a Balance Task", Annual Review of Cybertherapy and Telemedicine 2012, Studies in Health Technology and Informatics, 181: 103-107, 2012.
Lange et al. "Development and Evaluation of Low Cost Game-Based Balance Rehabilitation Tool Using the Microsoft Kinect Sensor", Conference Proceedings of the 33rd Annual International Conference of the IEEE Engineering in Medicine and Biology Society, EMBS, Boston, Massachusetts, USA, Aug. 30-Sep. 3, 2011, 2011: 1831-1834, 2011.
Mirelman et al. "Audio-Biofeedback Training for Posture and Balance in Patients With Parkinson's Disease", Journal of NeuEngineering and Rehabilitation, 8(35): 1-7, Published Online Jun. 21, 2011.
Pallavicini et al. "Interreality for the Management and Training of Psychological Stress: Study Protocol for a Randomized Controlled Trial", Trials, 14(191): 1-14, Jun. 28, 2013.
Peco-Antic et al. "Bladder Control Training in Girls With Lower Urinary Tract Dysfunction", International Brazilian Journal of Urology, 39(1): 118-127, Jan.-Feb. 2013.
Rao et al. "Pregait Balance Rehabilitation in Acute Stroke Patients", International Journal of Rehabilitation Research, 36(2): 112-117, Jun. 2013.
Riener et al. "Virtual Reality Aided Training of Combined Arm and Leg Movements of Children With CP", Medicine Meets Virtual Reality 20, Studies in Health Technology and Informatics, 184: 349-355, 2013.
Sisto "An Overview of the Value of Information Resulting From Instrumented Gait analysis for the Physical Therapist", Gait Analysis in the Science of Rehabilitation, Section 3(Chap.2): 76-84, 1998.
Stevens et al. "Unintentional Fall Injuries Associated With Walkers and Canes in Older Adults Treated in U.S. Emergency Departments", Journal of the American Geriatrics Society, JAGS, 57(8): 1464-1469, Aug. 2009.
Thomas et al. "Walking Aid Use After Discharge Following Hip Fracture Is Rarely Reviewed and Often Inappropriate: an Observational Study", Journal of Physiotherapy, 56: 267-272, 2010.
Varoqui et al. "Effect of Coordination Biofeedback on (Re)Learning Preferred Postural Patterns in Post-Stroke Patients", Motor Control, 15: 187-205, 2011.
Volk et al. "EMG Biofeedback Training Zuhause zur Therapie der Defektheilung bei Chronischer Fazialisparese [EMG Biofeedback Training at Home for Patient With Chronic Facial Palsy and Defective Healing] ", Laryngo -Rhino -Otologie, 93(1): 15-24, Published Online on Jul. 5, 2013.
Xu et al. "Wireless Walker Dynamometer Design and Static Calibration Based on Ant Colony System", IET Wireless Sensor Systems, 3(3): 233-238, 2013.

* cited by examiner

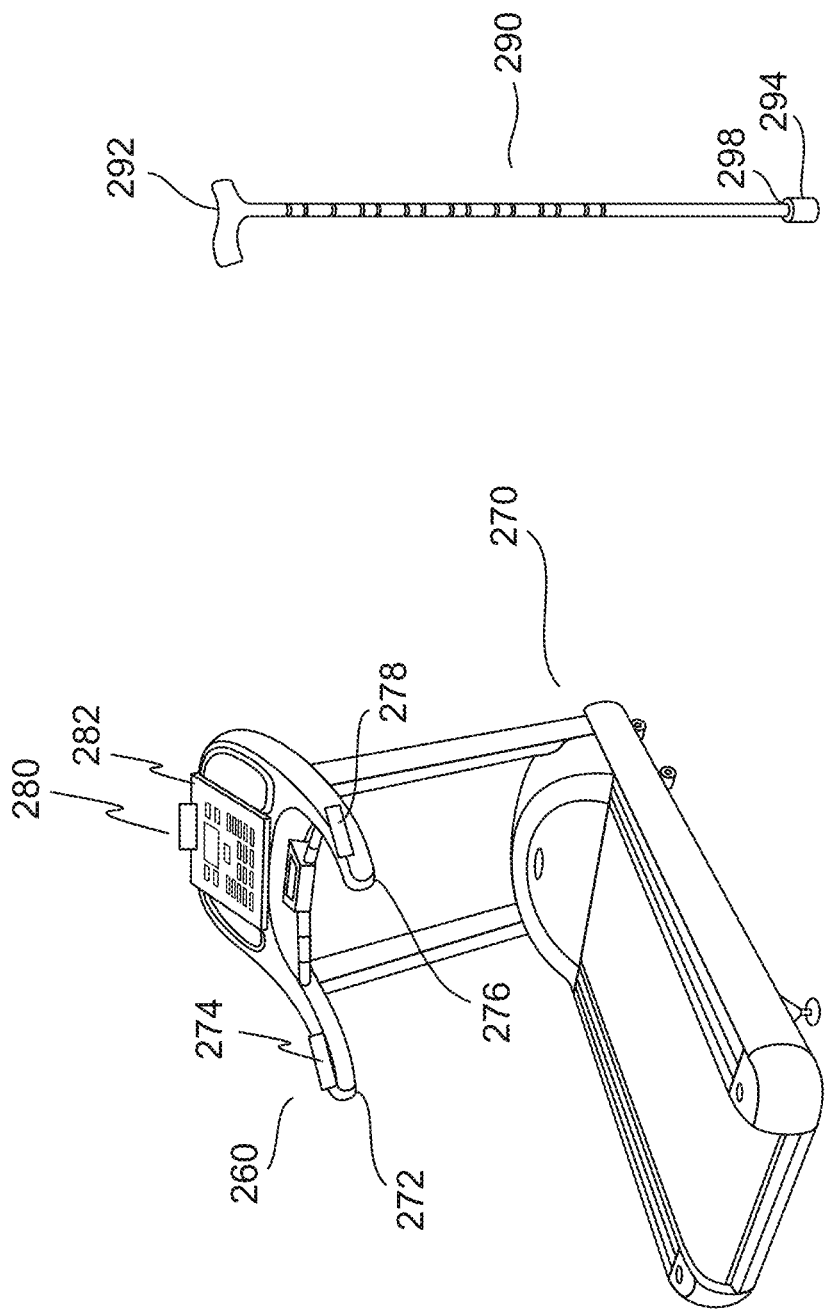

| F4 | F3 | F2 | F1 | X | W | Duration | Task |
|---|---|---|---|---|---|---|---|
| | | | | | | | Getting up from the chair |
| | | | | | | | Walking to the start of turn |
| | | | | | | | the turn |
| | | | | | | | Walking Back |
| | | | | | | | Sitting on chair |
| | | | | | | | Total |

Figure 16

| Units | Measured value | Threshold | Definition |
|---|---|---|---|
| Kg | W | w | total load |
| Kg | XR | non | right hand side load |
| Kg | XL | non | left hand side load |
| Kg | X | x | difference in Load Right / left |
| Degrees | F1 | f1 | Tilt to the right |
| Degrees | F2 | f2 | Tilt to the left |
| Degrees | F3 | f3 | Tilt forward |
| Degrees | F4 | f4 | Tilt backward |
| Degrees | | f | Tilting angle which means immediate danger of falling. |

Figure 17

WELCOME TO ...

| Results | | | | |
|---|---|---|---|---|
| Weight bearing | Symmetry | Walker Tilt | TUG walking results | Endurance |
| Date | Target rt-lt load differences | Actual rt-lt load differences | Daily walking time | Time maintaining target threshold (%) |

| Results | | | | | | | |
|---|---|---|---|---|---|---|---|
| Weight bearing | Symmetry | Walker Tilt | TUG walking results | Endurance | | | |
| Date | Activity period | Average load | Rt-Lt differences | No. forward tilts | No. backward tilts | No. left tilts | No. right tilts |

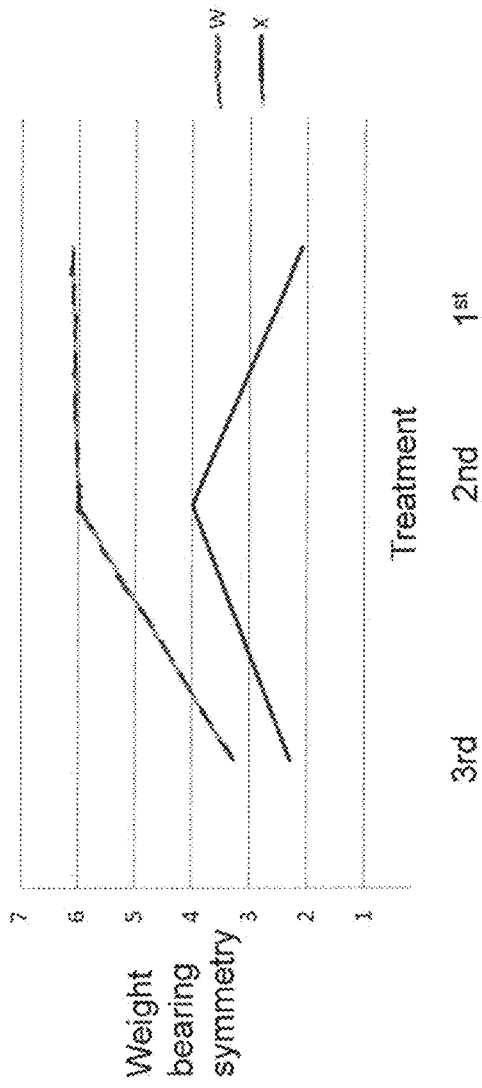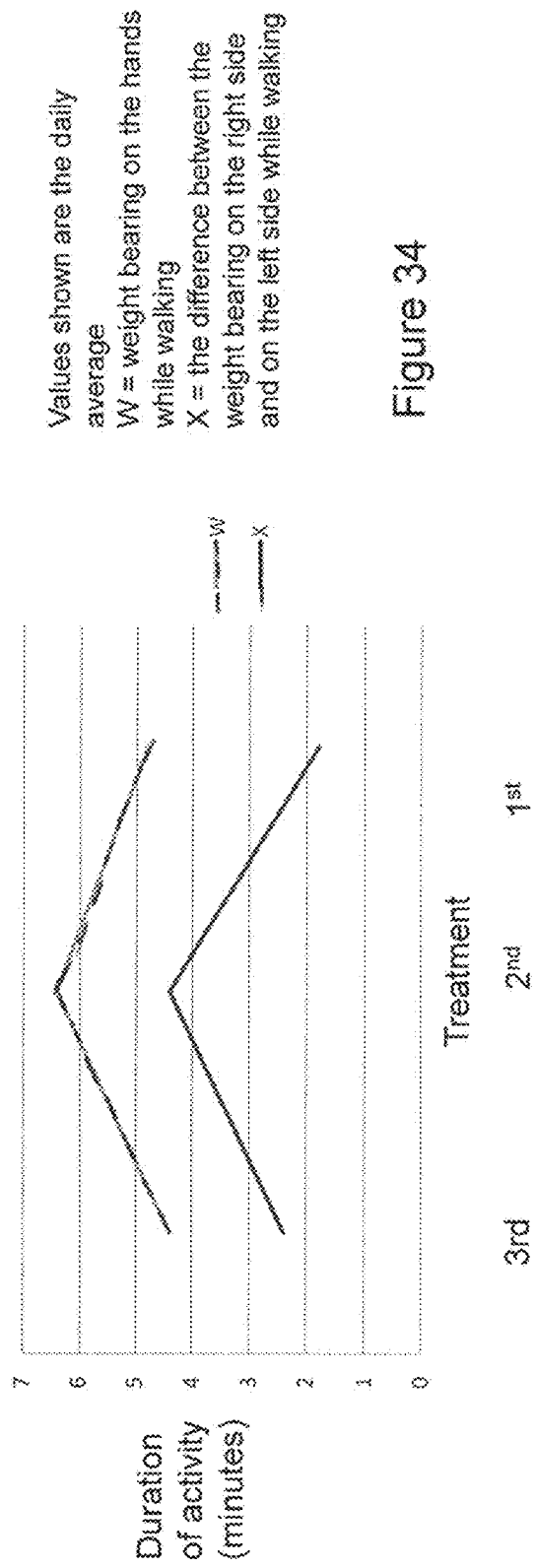
Figure 34

Distribution of weight bearing on the walker grips

| XL – Load on the left side | XR – Load on the right side | Date |
|---|---|---|
| | | |
| | | |
| | | |
| | | |
| | | |

Return to main menu

Return to previous screen

Figure 35

Endurance

| Activity level for 6 minutes | Date |
|---|---|
| | |
| | |
| | |

[ Return to main menu ]   [ Return to previous screen ]

Figure 36

TUG Results from walker test

| F4 | F3 | F2 | F1 | X | W | Duration of activities | Date |
|---|---|---|---|---|---|---|---|
|  |  |  |  |  |  |  |  |
|  |  |  |  |  |  |  |  |
|  |  |  |  |  |  |  |  |
|  |  |  |  |  |  |  |  |
|  |  |  |  |  |  |  |  |

Return to main menu

Return to previous screen

Figure 37

Planning a program for the continuation of therapy at home

| X | W | Activity level for 6 minutes | Date |
|---|---|---|---|
| | | | |
| | | | |
| | | | |
| | | | |
| | | | |

[Print]   [Return to main menu]   [Return to previous screen]

Figure 38

WALKER-ASSIST DEVICE

RELATED APPLICATIONS

This application is a National Phase of PCT Patent Application No. PCT/IL2014/050935 having International filing date of Oct. 29, 2014, which claims the benefit of priority under 35 USC § 119(e) of U.S. Provisional Patent Application No. 61/896,746 filed on Oct. 29, 2013. The contents of the above applications are all incorporated by reference as if fully set forth herein in their entirety.

FIELD AND BACKGROUND OF THE INVENTION

The present invention, in some embodiments thereof, relates to a device for retrofitting to a walker and, more particularly, but not exclusively, to a system, device and method for providing real time instructions to a user of a walker.

Bolton, in U.S. Patent Application Publication No. 2011/0023920 A1, discloses a "digital walker comprising a walker with a digital monitoring device and digital display". The digital monitoring device comprises at least one sensor. The sensor may be a biological or physiological sensor, a geographical or distance sensor, or a speed sensor. The data from the sensor may be displayed on the digital display.

Flentov et al., in U.S. Pat. No. 7,054,784, discloses methods and systems "for determining speed, power and/or impact (sporting characteristics) of persons involved in activity. Wireless signals may be generated indicative of the sporting characteristics for receipt and display on a watch worn by the user or on a remote display. Sensors may attach to the person or to a vehicle ridden by the person, to gauge activities such as jogging, hockey, biking, football and aerobics".

Additional background art includes the following references:

"Balance Rehabilitation Therapy by Tongue Electrotactile Biofeedback in Patients with Degenerative Cerebellar Disease", Cakrt et al., *NeuroRehabilitation,* 2012, 31(4), 429-34.

"Pregait Balance Rehabilitation in Acute Stroke Patients", Rao et al., *Int. J. Rehabil. Res.,* 2013 June; 36(2), 112-7.

"EMG Biofeedback Training at Home for Patient with Chronic Facial Palsy and Defective Healing," Fabian Volk G. et al., *Laryngorhinootologie,* 2013 Jul. 5.

"Development and Evaluation of Low Cost Game-Based Balance Rehabilitation Tool Using the Microsoft Kinect Sensor", Lange B. et al., *Conf. Proc. IEEE Eng. Med. Biol. Soc.,* 2011; 2011:1831-4.

"Efficacy of Nintendo Wii Training on Mechanical Leg Muscle Function and Postural Balance in Community-Dwelling Older Adults: A Randomized Controlled Trial", Jorgensen M G et al., *J. Gerontol. A Biol. Sci. Med. Sci.,* 2013 July, 68(7), 845-52.

"Determining the Preferred Modality for Real-Time Biofeedback during Balance Training", Bechly K E et al., Gait Posture, 2013 March, 37(3), 391-6.

"Audio-Biofeedback Training for Posture and Balance in Patients with Parkinson's Disease", Mirelman A. et al., *J. Neuroeng., Rehabil.,* 2011 June, 8:35.

"Exergaming for Elderly: Effects of Different Types of Game Feedback on Performance of a Balance Task", Lamoth C J et al., *Stud. Health Technol. Inform.,* 2012, 181:103-7.

"Virtual Reality Aided Training of Combined Arm and Leg Movements of Children with CP", Riener R et al., *Stud. Health Technol. Inform.,* 2013, 184: 349-55.

"Effect of Coordination Biofeedback on (Re)learning Preferred Postural Patterns in Post-Stroke Patients", Varoqui D., *Motor Control,* 2011 April, 15(2): 187-205.

SUMMARY OF THE INVENTION

The present invention, in some embodiments thereof, relates to a device for retrofitting to a walker and, more particularly, but not exclusively, to a system, device and method for providing real time instructions to a user of a walker. The device may provide feedback to the user of the walker or to a caregiver, physician, or other professional regarding at least one physical parameter of at least one location on the walker.

According to an aspect of some embodiments of the present invention there is provided a system for monitoring the use of a walker comprising: at least one sensor adapted for retrofitting to a walker, for measuring a physical parameter at at least one location on the walker and for sending at least one feedback signal indicating a value of the physical parameter measured.

According to some embodiments of the invention, the system further comprises: a computerized processor configured to receive the at least one signal indicating the value of the physical parameter measured from the at least one sensor, to analyze the at least one signal, and to provide a feedback signal to at least one of a user of the walker and a third party monitor of the user of the walker; and a memory coupled to the computerized processor.

According to some embodiments of the invention, the physical parameter is at least one of a step length, swing/stance, duration and base of support.

According to some embodiments of the invention, the walker includes at least one of at least one handle and wheels and the at least one location includes at least one of the at least one handle and the wheels of the walker.

According to some embodiments of the invention, the at least one sensor includes at least one of a mechanical sensor, an electromechanical sensor, and an electro-optical sensor.

According to some embodiments of the invention, at least one connector fastens the system for monitoring the use of a walker to the walker.

According to some embodiments of the invention, at least one connector fastens the system for monitoring the use of a walker to the walker without at least one of a need to disassemble the walker, a need to disassemble the system for monitoring the use of a walker, a need for a technician and a need for tools.

According to some embodiments of the invention, the system comprises a flexible joint bendable to the shape of a top portion of the walker.

According to some embodiments of the invention, at least one signal is provided instantly.

According to some embodiments of the invention, the at least one sensor comprises one of a pressure sensor and a force sensor; the measuring a physical parameter comprises measuring one of pressure and force of a hand upon at least one hand grip; and the analysis of the at least one signal comprises comparing the values of the one of pressure and force measured.

According to some embodiments of the invention, the system further comprises an accelerometer configured to measure at least one of movement and acceleration of the walker along a longitudinal axis, a lateral axis and a vertical axis about the walker's center of mass.

According to some embodiments of the invention, the accelerometer is comprised in a portable communication device.

According to some embodiments of the invention, the system further comprises a GPS monitor measuring the walker's location over time.

According to some embodiments of the invention, the GPS monitor is comprised in a portable communication device.

According to some embodiments of the invention, a portable communication device acts as the processor.

According to some embodiments of the invention, a portable communication device transmits the at least one feedback signal.

According to some embodiments of the invention, the at least one feedback signal is provided to at least a patient using the walker.

According to some embodiments of the invention, the at least one feedback signal is provided through vibration of at least one part of a frame of the walker.

According to some embodiments of the invention, the at least one feedback signal is provided on a display screen located in view of the patient using the walker.

According to some embodiments of the invention, the display screen is an integral part of the system.

According to some embodiments of the invention, the display screen is comprised in a portable communication device attached to a dock, wherein the dock is an integral part of the system.

According to some embodiments of the invention, the at least one feedback signal is provided to at least a third party monitoring a patient using the walker.

According to some embodiments of the invention, the at least one feedback signal is provided to the third party by a portable communication device.

According to some embodiments of the invention, the at least one feedback signal is provided by at least one of an email, a text message and a voice mail message.

According to some embodiments of the invention, an alert signal is provided when at least an increased risk of a user of the walker falling is detected.

According to some embodiments of the invention, the system further comprises an audio speaker configured to deliver the alert signal.

According to some embodiments of the invention, the system further comprises a portable communication device configured to deliver the alert signal to at least a third party monitoring a patient.

According to some embodiments of the invention, data collected by the system is analyzed to create guidelines for a patient's rehabilitation.

According to some embodiments of the invention, the at least one sensor is integrated into the walker during the manufacture of the walker.

According to an aspect of some embodiments of the present invention there is provided a system for monitoring the use of a walker comprising: a dock which attaches to a walker; wherein the dock is configured to interface with a portable communication device comprising: a processor; an application for monitoring the use of the walker; a screen display; and at least one of an imbalance sensor, an accelerometer, and a GPS monitor; wherein: the at least one of an imbalance sensor, an accelerometer and a GPS monitor measures at least one movement parameter of the walker; the measured at least one movement parameter is analyzed by the processor to create feedback; the screen display displays the feedback; and the portable communication device transmits the feedback to a third party monitor of a patient using the walker.

According to some embodiments of the invention, the processor is configured to determine the degree to which a patient is tilting to a side.

According to an aspect of some embodiments of the present invention there is provided a method for monitoring the use of a walker comprising: measuring at least one physical parameter on a walker; sending at least one signal indicating a value obtained by the measuring of at least one physical parameter to a computerized processor with a coupled memory; analyzing the at least one signal indicating a value; and providing an instant feedback signal to at least one of a user of the walker and a third party monitor of the user of the walker.

According to some embodiments of the invention, the method further comprises creating a personalized profile of the user of the walker wherein the analyzing comprises analyzing the at least one signal indicating a value in the context of the personalized profile.

According to some embodiments of the invention, the personalized profile includes a plurality of stages of rehabilitation through which the user of the walker is expected to pass.

According to some embodiments of the invention, the instant feedback signal is an alert signal.

According to some embodiments of the invention, the instant feedback signal comprises a light emanating from a walker-assist device and creating an indication, on the ground in front of the walker, of a direction in which the user of the walker should proceed.

According to some embodiments of the invention, the instant feedback signal comprises the vibrations of a vibrating element.

According to an aspect of some embodiments of the present invention there is provided a walker-assist device comprising: at least one sensor for retrofitting to a walker, for measuring a physical parameter on the walker and for sending at least one feedback signal indicating a value of the measurement of the physical parameter; a memory coupled to a computerized processor; and at least one connector fastening the at least one sensor to the walker.

According to some embodiments of the invention, the at least one sensor is at least one pressure or force sensor.

According to some embodiments of the invention, the at least one pressure sensor is located in at least one hand grip of the walker.

According to some embodiments of the invention, the at least one feedback signal is an indication of imbalance of the user of the walker.

According to some embodiments of the invention, the at least one feedback signal is provided instantly upon measuring the physical parameter.

According to some embodiments of the invention, the feedback signal is an alert signal.

According to some embodiments of the invention, the alert signal is delivered one of through vibration of at least one part of the walker-assist device and through vibration of at least one grip of the walker.

According to some embodiments of the invention, the at least one connector connects to the walker without the need for any tools or for a technician.

According to some embodiments of the invention, the walker-assist device further comprises a computerized processor configured to receive the at least one feedback signal indicating the value of the physical parameter measured from each one of the at least one sensor, to analyze the at least one signal, and to provide an feedback signal to at least one of a user of the walker and a third party monitor of the user of the walker.

According to an aspect of some embodiments of the present invention there is provided a system for monitoring the use of a walker comprising: at least one sensor for measuring at least one physical parameter of the walker and for sending at least one feedback signal indicating a value of the at least one physical parameter measured, wherein the at least one feedback signal includes a vibration of at least one part of the walker.

According to some embodiments of the invention, the vibration provides feedback to a user of the walker, said feedback including an indication of the at least one physical parameter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2c is an image of a walker-assist device utilizing tape containing pressure sensors, as a retrofit for a treadmill, according to some embodiments of the invention;

FIG. 2d is a schematic illustration of a walker-assist device utilizing a pressure sensitive disk located on a walking stick, according to some embodiments of the invention;

FIG. 16 is a table showing measurements of different parameters and time duration for each stage of the TUG test, according to some embodiments of the invention;

FIG. 17 is a table showing definitions of parameters measured during a TUG test, their units of measure, and the corresponding symbol for the pre-determined threshold value of each parameter, according to some embodiments of the invention;

FIG. 19 is a screen shot of the welcome screen which appears when the walker-assist device is turned on, according to some embodiments of the invention;

FIG. 23 is a screen shot of a new patient identification screen, according to some embodiments of the invention;

FIGS. 25*a*-*b* and FIGS. 26-27 are screen shots viewable after pressing the various tabs shown in FIG. 24, according to some embodiments of the invention;

FIG. 34 is a screen shot of a patient progress report shown in graph form, according to some embodiments of the invention;

FIG. 35 is a screen shot of patient data summarizing measured load levels, according to some embodiments of the invention;

FIG. 36 is a screen shot of patient data summarizing activity levels achieved, according to some embodiments of the invention;

FIG. 37 is a screen shot of patient data summarizing TUG test results, according to some embodiments of the invention; and FIG. 38 is a screen shot of a home therapy program plan, according to some embodiments of the invention.

DESCRIPTION OF SPECIFIC EMBODIMENTS OF THE INVENTION

Figure 1A:
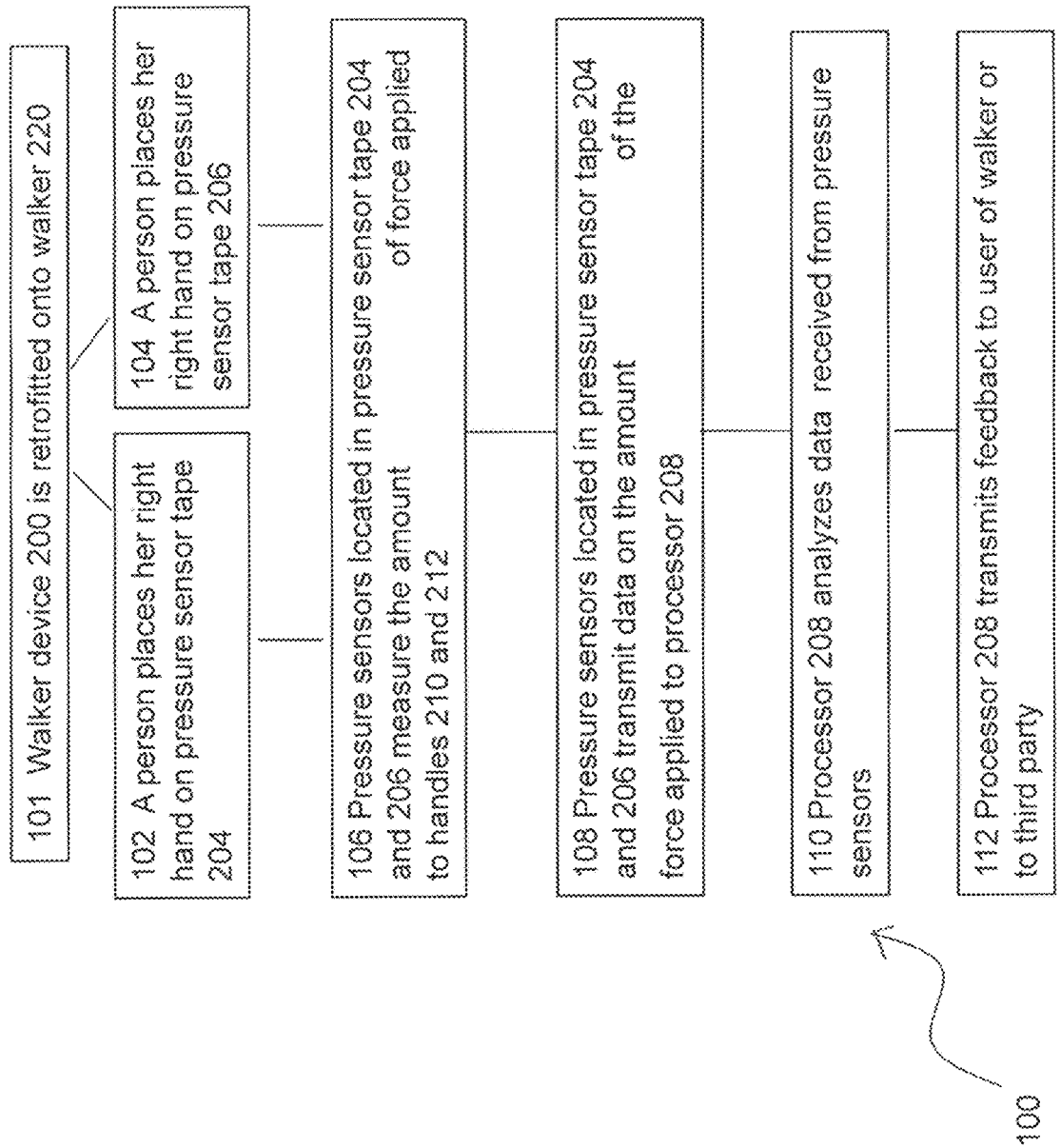
FIG. 1a is a flow chart demonstrating the use of a walker-assist device with a walker, according to some embodiments of the invention.

The present invention, in some embodiments thereof, relates to a device for retrofitting to a walker or a walker including a device and, more particularly, but not exclusively, to a system, device and method for providing real time instructions to a user of a walker (hereinafter, "the patient").

An aspect of some embodiments of the present invention relates to retrofitting a walker with a walker-assist device. In an exemplary embodiment of the invention, the walker-assist device includes at least one sensor to sense a patient activity. In an exemplary embodiment of the invention, the device is retrofitted to a walker without the need for using any tools or for a technician.

In an exemplary embodiment of the invention, the assist-device is a flexible device, for example, in the form of a flat flexible strip (e.g., a tape of uniform or varying width). In an exemplary embodiment of the invention, the tape includes embedded sensors and/or defines a sandwich of layers with sensors in an inside layer. Optionally, the tape is attached to the walker by a self-adhesive layer thereon, by an over layer and/or using two-sided tape.

In an exemplary embodiment of the invention, the use of a flexible device allows the device to be attached to a range of walker designs. Optionally or alternatively, the device is thin enough so as to not interfere with the geometry of a walker.

In an exemplary embodiment of the invention, the device is flexible by having one or more flexible sections or joints therein. For example, the device may include a plurality of rigid sections attachable to a walker frame, which are interconnected by one or more flexible joints or sections. In an exemplary embodiment of the invention, such rigid sections are attached to an existing walker frame using one or more connectors. In some embodiments, the connectors define a spacing between the device and the frame. In other embodiments, the spacers allow the device to abut the frame.

In an exemplary embodiment of the invention, the walker-assist device includes a dock for integrating a portable device for computing and optionally sensing, the portable device having a processor, a display, a user interface such as, for example, a touch screen, optionally with a communicator. The portable device may be, for example, a Smartphone, PDA (personal digital assistant), portable media player or tablet computer. Optionally, the dock attaches to the flexible joint. Optionally or alternatively, the portable communication device acts as a processor for processing signals provided by the assist device and/or for external communication and/or for display to a patient or other user (such as a physical therapist).

Optionally, the device may include at least one sensor such as, for example, a mechanical sensor, an electromechanical sensor, and an electro-optical sensor. Exemplary sensors include, for example, a pressure sensor, an accelerometer, a barometer, a gyro, and/or a position indication device such as, for example, a GPS, and a base station-based position estimation device, in the portable communication device.

According to some embodiments, at least one sensor, such as a pressure sensor or a force sensor, may be located on the device, for example on a hand grip which fits the side of a walker, and a computerized processor analyzes the measurements provided by the at least one sensor. While, for the sake of clarity, the description may refer to a pressure sensor, it should be understood that the particular sensor may alternatively be a force sensor or any other sensor described herein. In one example, a pressure sensor is located at each hand grip on opposite sides of the walker. This may allow relative pressure on each side of the walker to be assessed. Optionally, pressure sensors are located at other parts of a frame where a grip may be applied, for example, a forward part of the frame. The sensing of pressure applied by a user of the walker to the handles may provide an indication that the user is leaning to one side while walking or standing, using the walker.

In some embodiments, two pressure or other sensors are provided on each grip, so as to provide an indication of which part of the grip receives more pressure relative to the remainder of the walker frame. This may assist in determining a center of gravity and/or a direction of a force vector of the patient. Optionally, the at least two pressure sensors in each hand grip are spaced sufficiently apart from each other to allow for the measurement of force in different vectors, including forward, backward, down, up, right and/or left. Other sensors, such as tension sensors, elongate pressure sensors (e.g., with position encoding), an accelerometer (optionally included in a portable communication device or a tablet computer) a tilt sensor, and an electro-optical sensor may be used instead or in addition and may be provided in the walker itself or as a separate unit which may be fastened to the walker or to the user of the walker and may communicate with the walker-assist device by Bluetooth technology.

Additionally, combinations of sensor measurements may be used to identify various conditions of a user of a walker having a walker-assist device. For example, measurements from an accelerometer, a gyro, and a pressure/force sensor may be used to identify a condition of imbalance, which is characterized by a tilt or a large sway. This may be identified by a variation in accelerometer reading and/or inconsistency between pressure/force readings on the right and left sides of the walker while the user is walking. This is discussed further herein.

An aspect of some embodiments of the invention relates to a walking assisting device (e.g., a walker) or a walker-retrofit device which provides feedback and/or guidance to a user of the device. In an exemplary embodiment of the invention, the device provides feedback to the patient, to her monitor, or to another person who may be remotely located, on physical parameters such as imbalance. Optionally, the device transmits feedback date in real time to a remote portable device such as, for example, a laptop, an iPad, or a Smartphone. Optionally, the device provides feedback on physical parameters of the walker and patient using the walker, the physical parameters measured by the device including at least one of walking speed, cadence, walking distance, stride length, step length, weight distribution, and sway. In an exemplary embodiment of the invention, the feedback is provided instantly (e.g., within less than 1 minute, less than 30 seconds, less than 10 seconds, less than 1 second, less than ½ second). Optionally, the feedback may be transmitted by a portable communication device provided on the walker-retrofit device.

Optionally, the feedback may provide data to a third party such as, for example, a physician or other medical professional, and the data may be used to provide the physician with processed information and clinical recommendations regarding the condition of the patient using the walker.

Optionally, the device monitors gait parameters such as, for example, step length, stance/swing, step duration, base of support, and sway of the patient, as discussed herein. In an exemplary embodiment, differences in measurements obtained from pressure/force sensors together with data collected from an accelerometer can be used to indicate the time of heel and toe contact with a walking surface, from which stance/swing/step/stride duration and cadence can be determined. When this data is combined with walking distance and speed, which may be calculated from data collected from an electro-optical sensor which measures wheel turns, step/stride length may be determined. Weight distribution and sway can be calculated from measurements obtained throughout the gait cycle from pressure/force sensors on the right and left sides of the walker-assist device.

These measurements may be used to calculate a swing base of support. The total weight measured on the handles gives an indication of a center of mass relative to the sides of the walker, and periodic differences between the right and left pressure/force measurements may indicate the sway of the patient in a direction of walking.

A sudden degradation or change in these parameters could indicate a potential risk of falling. Based on these parameters, the feedback may provide an indication of a deteriorating gait performance or sway/imbalance which might indicate an increased risk of patient falling, especially if the patient is elderly. For example, the feedback regarding gait of the patient, for example an inconsistent gait, may be used to provide an indication of a high risk of falling. For example, various parameters may be monitored and the measured values or a combination of these values may be compared to values in a table or to threshold values to determine an increased risk of falling for the user.

Optionally, in the case of a patient suffering from Parkinson's disease, the continuous collection of data by the device regarding the walking pace/gait of the patient may allow the identification of shuffling steps and/or "freezing spells." After such identification the device may provide the walker handle(s) with vibrations/pulses which may be transmitted to the patient at a rate appropriate for him, the vibrations/pulses acting as an external trigger to release him from a "frozen state" and which may allow him to continue walking at a more consistent pace/gait. Such feedback may have a metronome effect in that it assists the patient in maintaining a particular walking rhythm.

In an exemplary embodiment of the invention, guidance comprises one or more of a visual or auditory display indicating what a next activity should be. Optionally, the display is projected onto a ground. In another example, guidance comprises a vibration delivered to at least one grip of the walker and/or to at least one part of the walker-assist device, for example indicating a grip which should have less pressure applied thereto. In one example, activity is immediate, for example, where should a next step be. In another example activity is ongoing, for example, "walk 50 meters." Optionally, the performance of the activity and/or other guidance and/or result thereof is monitored by the device. In some embodiments the guidance is not rehabilitation related. For example, it may include navigation instructions. Optionally, such navigation instructions include an indication of paths suitable for the patient and/or include warning of problematic locations to traverse (e.g., uneven steps). Hazard indications are optionally provided by the patient or caregiver, or may be determined automatically from patient performance at certain locations and/or may be provided by a central and/or shared repository.

In an exemplary embodiment of the invention, feedback is in the form of an alert, for example, indicting tipping danger or inappropriate amounts of force and/or force vectors on different parts of the device. In some embodiments, an alert is a visual or auditory alert or an alert delivered through vibration of at least one part of the walker-assist device. Optionally or alternatively, the feedback is in the form of a summary to a therapist of, for example, recent activity, compliance and/or difficulty.

In an exemplary embodiment of the invention, the alerts (or other feedback) and/or guidance are dependent on a stage of rehabilitation of the patient and/or a rehabilitation plan for the patient. In embodiments, statistical reports may be derived in a variety of portions of a computer programs provided with the system, which allow the building of a user profile suitable for his characteristics and performance, thereby allowing for the improvement of quality of treatment and for the determining of the type of treatment.

In some exemplary embodiments of the invention, the feedback may comprise a display screen or text message, optionally on a portable communication device such as, for example, a Smartphone or a tablet computer, such as "move your right foot forward"; a hand grip vibrating to indicate that excessive force is being applied to that hand grip; an audio alert stating "shift some of your weight to your left side," and/or a laser light indicating the area of the ground to which the patient should strive to reach.

In some exemplary embodiments of the invention, instant feedback may comprise an alert signal when standard and/or patient specific thresholds, such as tilting thresholds, are exceeded or not reached. These thresholds may include, for example, a predetermined amount of combined weight exerted on both hand grips, a predetermined amount of weight exerted a predetermined number of times or at a predetermined frequency. Absence of reaching such thresholds may indicate an activity level which is lower than desired according to a caregiver's or physiotherapist's instructions.

In embodiments, feedback due to leaning to one side may result in an alert to indicate a dangerous situation when a user is walking straight, but may not result in a warning when the user is turning. In embodiments, the system may determine normal activity of a user during a specific time period and may issue an alert when at least one or a combination of measured parameters deviates from the determined normal activity. This may provide an indication that something is not right with the user and can preempt a fall or other problem. For example, a text message sent to a third party monitor may state "danger of falling," with the identity of the patient and/or GPS provided location of the device. Optionally, an audio alert such as a siren or a loud recording of the words "Fall Alert," and/or a visual alert such as swirling lights, may act as an alert signal emanating from the device itself, in order to alert the patient and/or people close to the patient.

In an exemplary embodiment of the invention, a personal profile of each patient is created based on answers provided to questions and/or based on test and/or activity results. Optionally, questions are provided on a display screen attached to the walker-assist device. Optionally, the device uses the personal profiles and/or data from previous uses of the device by a patient to create individualized thresholds and/or other settings suitable to that particular patient and/or his/her particular situation. Optionally, different thresholds are established for different stages of rehabilitation through which a patient is expected to pass, for example, from standing with equal weight distribution to walking long distances.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Retrofitting the Walker-Assist Device to a Walker

According to some embodiments of the invention, the components of the walker-assist device, for example, sensors, a computerized processor and/or a display screen, are retrofitted to a walker. As used herein, the term "retrofitting" means installing or fitting (the walker-assist device or system, for example) for use in and/or on an existing walker structure. For example, the walker-assist device may be retrofitted onto an existing walker after the manufacture of the walker is complete.

According to some embodiments of the invention, a plurality of components is each individually retrofitted to the walker. Optionally or alternatively, some or all of the components are first joined to each other and then retrofitted to the walker. For example, the components may be attached to a strip of tape or to a flexible joint before being retrofitted. In some embodiments, a walker-assist device is provided pre-integrated and only needs to be attached to a walker (or other walking assisting device, such as a cane). In some cases, the walker-assist device is in two or more parts which communicate wirelessly with each other.

Retrofitting with a Thin Flexible Device

Figure 2B:
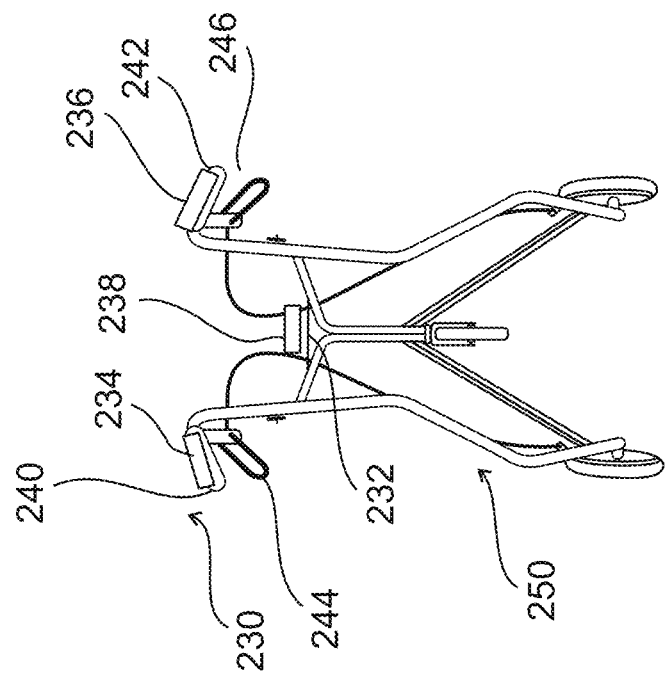
FIG. 2b is an image of a walker-assist device utilizing tape containing pressure sensors, as a retrofit for a foldable walker with brakes, according to some embodiments of the invention.
Figure 2A:
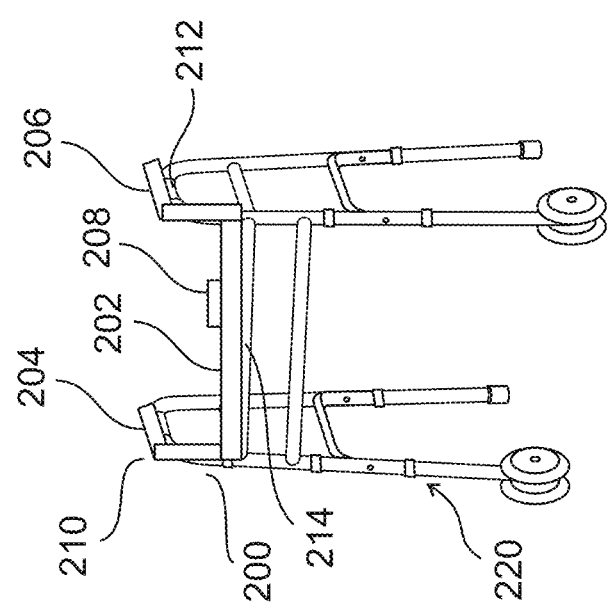
FIG. 2a is a schematic illustration of a walker-assist device utilizing a tape containing pressure sensors, as a retrofit, according to some embodiments.

Referring now to the drawings, FIG. 2a is a schematic illustration of a walker-assist device utilizing a thin, flexible element containing one or more pressure or other sensors, mounted on a walker, according to some embodiments of the invention. Optionally, the thin, flexible element is a light and/or sticky material. Optionally, the light and/or sticky material is in the form of a tape. According to some embodiments, walker-assist device 200, comprising a film of tape 202, comprising pressure sensors 204 and 206 and/or other elements optionally embedded into film of tape 202 or located on the exterior of film of tape 202, such that the pressure sensors may receive input from each handle grip and from the point of connection between each of the handles and the rest of the walker 220. Optionally, the walker-assist device is retrofitted to standard walker 220. Optionally or alternatively, pressure sensors 204 and 206 and/or other elements may receive input from each handle grip and from the point of connection between each of the handles and the rest of the walker 220, in a flexible cable and/or wire which is attached to film of tape 202. According to some embodiments, the flexible cable and/or wire has a thickness of 0.2-3 mm, optionally 1.5 mm.

According to some embodiments, film of tape 202 is made from plastic, cloth, paper and/or polyimide. According to some embodiments, film of tape 202 further comprises an adhesive. Optionally, the adhesive is made from, for example, high- or medium density polyurethane.

Optionally, the adhesive is located on one side of the film of tape 202. Alternatively, the adhesive is located on both sides of the film of tape 202.

According to some embodiments, film of tape 202 is sufficiently thin to allow the user of the walker to comfortably wrap her hands around the side grips of the walker. For example, film of tape 202 may have a thickness of 0.03-4.00 mm, optionally about 1 mm. Optionally, when pressure sensors are embedded into film of tape 202, the thickness of the film of tape 202 at greater in the locations of embedment. For example, film of tape 202 may be 1-4 mm, optionally 2 mm, thicker in the locations of embedment. Optionally, film of tape 202 only covers part of the hand grips and/or other parts of the walker. Alternatively, film of tape 202 fully covers parts of the walker.

The hand grips may be fabricated from a material that is comfortable to grasp, and may be fabricated from a material that prevents or minimizes sweating, is non-corrosive, and can withstand prolonged exposure to environmental elements such as sun and moisture. Further, the hand grips may be easily sterilizable or replaceable for hygienic purposes, for example, when in use in a hospital or clinic.

According to some embodiments, film of tape 202 is oriented on the side grips such that pressure sensors 204 and 206 are located on the top of the side grips. Alternatively, film of tape 202 is oriented on the side grips such that pressure sensors 204 and 206 are located on the bottom of the side grips. Alternatively, film of tape 202 is oriented on the side grips such that pressure sensors 204 and 206 are located on the side of the side grips. Optionally or alternatively, a plurality of pressure sensors is located on each of the side grips. Optionally or alternatively, the pressure sensors on each side grip are spaced apart from each other. Optionally, the spacing apart of the sensors allows the device to measure force sensed at from the point of connection between each of the handles and the rest of the walker 220 in different vectors, such as up/down, right/left and forward/backward.

Retrofitting with a Flexible Joint

Figure 3:
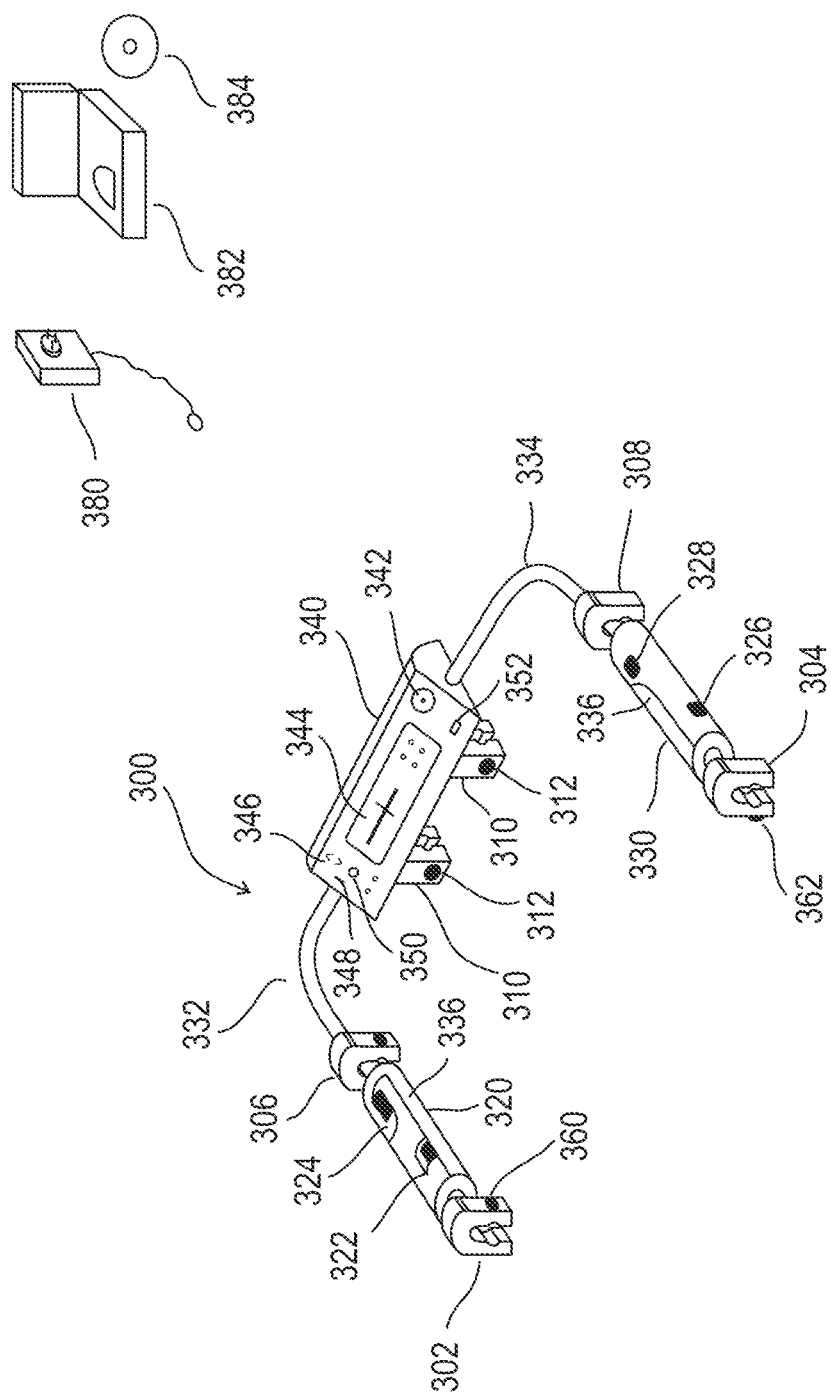
FIG. 3 is a schematic illustration of a walker-assist device with a display screen for retrofitting to a walker, according to some embodiments of the invention.

FIG. 3 is a schematic illustration of a walker-assist device 300 for retrofitting to a frame, for example a frame of a walker, according to some embodiments of the invention. In an exemplary embodiment, sensors, computerized processor, a display screen and/or other components of the walker-assist device are mechanically interconnected using a joint, optionally one or more flexible joints 332, 334, comprising connectors. Optionally, the flexible joint allows the walker-assist device to fit walkers of various shapes and/or sizes. Optionally, the connecting elements clip onto a walker without the need for using any tools. Wires for electrically interconnecting components optionally pass through a lumen in the joint and/or on an outside surface thereof.

Optionally, device 300 and/or flexible joint 332 is made from a light metal, for example aluminum, and/or PVC. According to some embodiments, flexible joint 332 and/or device 300 is sufficiently thin and/or suitably shaped so as to allow the user of the walker to comfortably wrap her hands around the side grips of the walker. For example, flexible joint 332 may have a thickness of 0.5-6 mm, optionally 2 mm.

In an exemplary embodiment of the invention, pressure sensors are embedded into flexible and/or rigid sections of device 300. Optionally, the thickness of the flexible joint 332 is the same in the locations of embedment. Alternatively, the thickness of the flexible joint 332 is greater in the locations of embedment. For example, flexible joint 332 may be 1-4 mm, optionally 2 mm, thicker in the locations of embedment. Optionally, flexible joint 332 only overlays and/or abuts part of the hand grips and/or other parts of the walker. Alternatively, flexible joint 332 fully covers parts of the walker.

Optionally, device 300 may be attached to part of the hand grips and/or other parts of the walker at a single point, with a flexible joint, thereby allowing angular adjustment of the device. This may improve the comfort level of gripping the device for users of different heights.

In embodiments, the device may be screwed onto a portion of the walker. Optionally, each hand grip is separately attachable to the structure of the walker and the feedback mechanism is optionally independently fastened to the horizontal portion of the walker facing the user. Between the feedback mechanism and each hand grip there are cables which are flexible, thereby allowing the walker to fold, such as for storage when not in use.

In some embodiments, pressure sensors and/or other elements are located in a flexible cable and/or wire which is attached to flexible joint 332 and/or other parts of device 300. Optionally or alternatively, the flexible cable and/or wire has a thickness of 0.5-3 mm, optionally 1.5 mm. Optionally or alternatively, pressure sensors and/or other elements are separate elements which directly attach to flexible joint 332.

According to some embodiments, device 300 and/or flexible joint 332 comprises at least one hand grip. Optionally, the hand grip may wrap around the top of the side bar of the walker. Alternatively, the hand grip may wrap completely around the side bar of the walker.

According to some embodiments, the hand grip is sufficiently thin to allow the user of the walker to comfortably wrap her hands around the side of the walker. For example, the hand grip may have a thickness of 0.5-4 mm, optionally 2 mm. According to some embodiments, the hand grip adds to the thickness of the side bar both on top and underneath the side bar when the hand grip wraps completely around the side bar of the walker. For example, a hand grip of 1 mm thickness that wraps completely around the side bar adds 2 mm to the thickness of the side bar. In some embodiments, a gap is formed between the handgrip of device 300/flexible joint 332 and the original walker frame. This gap may be, for example 3 cm, or any other desired distance, so as to allow enough space so that a user may comfortably and safely grip the hand grip with all of his fingers.

In some embodiments, pressure (or other) sensors are embedded into the hand grip. In some embodiments, one or more vibratory elements 336 are integrated into the handgrip(s) and/or into the tape walker assist device, to provide feedback. In an exemplary embodiment of the invention, vibratory elements are embedded into flexible and/or rigid sections of device 300. In embodiments, the vibratory elements may include vibration components such as, for example, piezoelectric crystals which are electrified to vibrate, an ERM (eccentric rotating mass) vibration motor, a vibrating magnet, and a vibration speaker coupled to the device. Optionally or alternatively, one or more acoustic outputs are integrated into the handgrip or tape device.

According to some embodiments, the hand grip is made of or covered with foam, rubber, a blend of foam and rubber and/or rubber compounds, for example, NPVC, UV-NPVC and/or EPDM. According to some embodiments, the exterior and/or exterior of the hand grip is smooth, textured and/or buffed.

According to some embodiments, control unit 340 comprises at least one fastener 310 configured to attach control unit 340 to a front cross bar 202 of a walker 220. At least one fastening screw 312 may be adjusted (e.g., using fingers) to tighten at least one fastener 310 and stabilize control unit 340. A potential advantage provided by the fasteners is that they allow the walker-assist device to be retrofitted to existing walkers of various shapes and sizes, treadmill and/or walking cane, according to some embodiments.

According to some embodiments, left side grip 320 comprises at least one fastener 302 configured to attach to the left cross bar 212 of a walker 220. At least one fastening screw 360 may be tightened to stabilize left side grip 320.

According to some embodiments, right side grip 330 comprises at least one fastener 304 configured to attach to the right cross bar 210 of a walker 220. At least one fastening screw 362 may be tightened to stabilize right side grip 330.

According to some embodiments, fasteners 310, 302 and 304 contain "claws," butterfly screws and/or other self-contained mechanisms for tightening and/or clipping on the fasteners around or to the parts of the walker to which they attach without the need for tools.

In an exemplary embodiment of the invention, a flexible joint 332 connects left side grip 320 to control unit 340. Optionally, a flexible joint 334 connects right side grip 330 to control unit 340. In an exemplary embodiment of the invention, flexible joints 332 and 334 allow walker-assist device 300 to bend sufficiently to fit different sized and shaped walkers, for example, foldable walker 250 of FIG. 2b, with a short cross bar 232.

In some embodiments, a rigid frame is used instead of a flexibly jointed frame, optionally being sized and/or shaped for a particular walker design.

Retrofitting a Walker-Assist Device to a Foldable Walker

According to some embodiments, the walker to which the walker-assist device may be attached is a foldable walker. For example, FIG. 2b is an image of a walker-assist device 230 utilizing a tape containing pressure sensors 234 and 236 on hand grips 240 and 242, respectively, on foldable walker 250. Optionally, foldable walker 250 contains hand brakes 244 and 246, according to some embodiments.

According to some embodiments, the cross bar 232 of foldable walker 250 has a shorter length than a standard cross bar. Optionally, computerized processor 238 attaches to cross bar 232.

Retrofitting Walker-Assist Device to a Treadmill

According to some embodiments, the walker-assist device attaches to a treadmill. For example, FIG. 2c is an image of a walker-assist device 260 utilizing tape containing pressure sensors 274 and 278 on hand grips 272 and 276, respectively, on treadmill 270. Optionally, computerized processor 280 attaches to control panel 282 of treadmill 270.

Retrofitting Walker-Assist Device to a Cane

When attaching to a cane, generally only one handgrip exists and has one or more pressure sensors attached thereto. FIG. 1b is a flow chart 140 demonstrating the use of a walker-assist device with a walking stick, according to some embodiments. At 142, a person places her hand on a walker handle 292 of walking stick 290 in FIG. 2d. Pressure sensor 294 then measures (144) the amount and/or direction of force applied to walking stick 290 and transmits the measurement data to computerized processor 298 (146), which may then provide, for example, feedback.

Use of a Portable Communication Device in Retrofitting

According to some embodiments, a compact, portable device, optionally with a communicator, such as a Smartphone, PDA, portable media device, or tablet computer acts as the processor, an imbalance sensor, an accelerometer, a GPS monitor, a tilt sensor, and/or the transmitter of messages to a third party monitor, as a pressure monitor and/or as the screen display. A potential advantage provided by the use of the portable communication device is that it may be lighter than the components it replaces, making the device lighter and potentially smaller and easier to retrofit to an existing walker.

As noted herein, pressure sensing or force sensing is performed by pressure sensors or force sensors located on the handles. Data from these sensors may be processed by the system and the basic functions of the system may be performed as discussed herein without the use of a compact processor.

While not absolutely necessary, a compact processor may, however, provide additional advantages, such as allowing a user to view an impressive and accurate display, as well as providing better graphical display of information than would be possible without the use of a compact processor. This would allow for storage and later analysis of the data acquired in the control unit of the walker, without relevance to the compact processor. Additionally, use of a compact processor may provide all the functions associated with a GPS, including transmitting the location of a user in the event of an emergency.

Dock for a Compact Processor

According to some embodiments, a dock for a portable communication device is provided which holds, attaches to and/or interfaces with the compact processor. For example, the dock may be attached to the front bar of a walker to provide the user of the walker a direct view of the compact processor when a patient is holding the walker and the compact processor is placed in the dock.

Preferably, at least some components of the walker-assist device are connected to the compact processor wirelessly, by Bluetooth. Optionally, the various sensors of the device are attached to a port in the compact processor. Optionally or alternatively, at least some components of the walker-assist device are connected to the compact processor wirelessly, for example, using NFC or Wi-Fi connections.

Power Supply

According to some embodiments, the walker-assist device is a cordless device powered by batteries in order to facilitate its retrofitting to a walker. According to some embodiments, the walker-assist device is integrated into the walker and is powered by batteries. Optionally, the batteries are rechargeable. Optionally, the walker-assist device may be recharged via the same USB cable which may be used to connect the walker to a computer for downloading data therefrom to the walker-assist device and vice versa. Optionally, there may be provided a charger having a USB connection for recharging the walker-assist device, if a connection to a computer is not available.

Optionally, the walker-assist device includes a sensor such that the walker-assist device is configured to revert to sleep mode when not in use in order to conserve energy. Optionally, non-use is detected based on lack of change in pressure and/or use of an accelerometer. Optionally, when movement is later detected, the walker-assist device is "woken up." Optionally, such a sensor is periodically monitored. A potential advantage provided by the conservation of energy while in sleep mode is that less charging is required or that charging is required less frequently, for example, once a day such as, for example, at night when the walker is not in use. Another potential advantage is that a lighter battery may be used, making the device lighter and potentially smaller and easier to retrofit to an existing walker. Alternatively, a power cable connecting to an electricity source powers the walker-assist device. Optionally, the device is provided with an on/off switch which allows the device to be turned off when not in use for an extended period or when in storage.

Integrating Walker-Assist Device During Manufacture

In an exemplary embodiment of the invention, the walker assist device is attached after manufacture. In some cases, a walker assist device and/or at least some components thereof may be attached during manufacture. For example, walker-assist device 200 is integrated into walker 220, and/or a walker of a different shape and/or design, during the manufacture of the walker, or at any other point prior to the provision of the walker to an end user of the walker.

Feedback

In an exemplary embodiment, the data obtained by at least one of the sensors is transmitted to a computerized processor which analyzes the data and provides guidance and/or feedback to a patient and/or to a third party monitoring the patient's walking and/or progress. According to some embodiments, the data is analyzed to provide instructions to the patient and/or her third party monitor on how she should proceed. For example, instructions may be provide in order to stabilize the patient's stance and/or gait. Optionally, the data analysis includes the creation of a rehabilitation plan for the patient. Optionally, the data analysis provides an indication of walking speed, cadence, walking distance, stride length, step length, weight distribution, and sway of the patient.

For example, changes in the amount of pressure/force applied to the handles together with data collected from an accelerator may indicate the time of heel and toe contact with a walking surface, and from these measurements the stance/swing/stride duration and cadence can be determined. By combining this data with information collected from an electro-optical sensor regarding the number of wheel turns, which directly corresponds to distance walked and speed, the step/stride length may be calculated.

Weight distribution and sway can be calculated from the mean and variance of the amount of pressure/force applied on each handle throughout the gait cycle, as known in the art.

The information derived may be used to provide real-time feedback to a patient, caregiver, or health care professional, as discussed herein.

Instant Feedback Signal—Non-Emergency

Figure 1B:
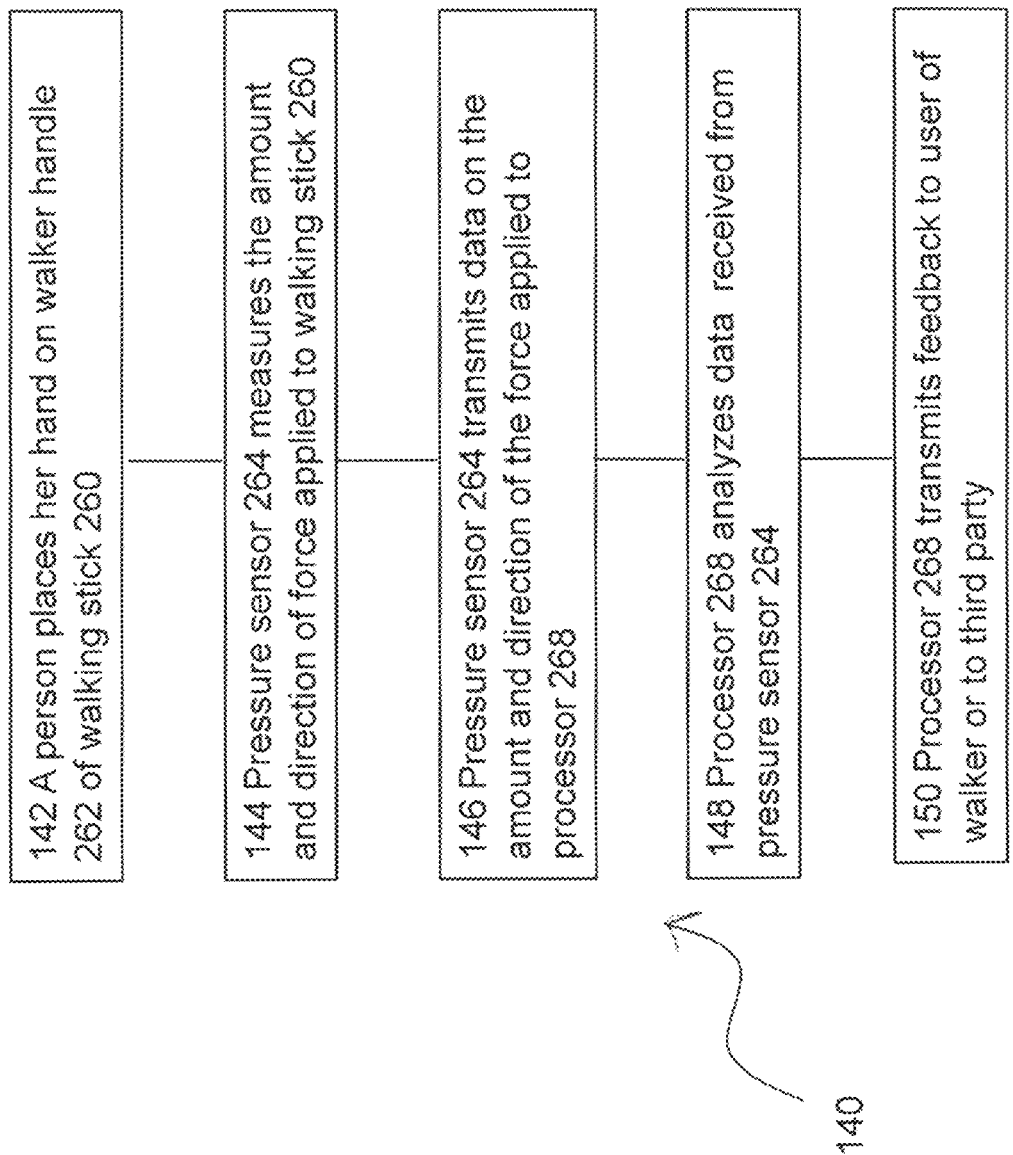
FIG. 1b is a flow chart demonstrating the use of a walker-assist device with a walking stick, according to some embodiments of the invention.

FIG. 1a is a flow chart 100 demonstrating the use of a walker-assist device for retrofitting to a walker, according to some embodiments. Flow chart 100 describes the use of a walker-assist device 200, schematically illustrated in FIG. 2a. Optionally, walker-assist device 200 is retrofitted onto an existing walker after the walker has been fully manufactured and sold to a retailer, hospital, rehabilitation center or end user. In an exemplary embodiment, no tools are required to retrofit the walker-assist device to a walker.

According to some embodiments, the computerized processor compares the established thresholds with obtained measurements to provide instant and/or personalized guidance to the patient and/or her third party monitor. For example, a display screen or text message may display "move your right foot forward," a hand grip may vibrate to indicate that excessive force is being applied to that hand grip, an audio alert may state "immediately shift some of your weight to your left side," a text message to a third party monitor may state "danger of falling," and/or a laser light may indicate the area of the ground to which the patient should strive to reach. Additional examples of instructions may include "take two steps forward," "walk 3 meters forward," and/or "walk for 10 minutes." Optionally or alternatively, real time guidance in using the walker is provided by creating a visual display, described below in the section "Visual Display." Optionally, a test may be performed. There a two standard tests which are often performed by physiotherapists for assessment purposes. A first test is a "6MW" test, in which a patient must walk for 6 minutes and feedback is received. A second test is a "TUG" test, in which a patient is first seated; then must stand, at which point timing begins; after which he must walk 3 meters, turn, return the 3 meters, and sit down.

The data analysis (110) potentially provides the advantage of informing both the patient and/or her monitor of the extent to which she is balanced and/or the degree to which she needs to adjust her stance, gait and/or use of the walker in order to stabilize herself and/or increase her walking efficiency, according to some embodiments. For example, the feedback provided at 112 may include a feedback signal indicating a percentage which indicates a corresponding degree of conformity with the expected use of the walker according to at least one measured parameter, such as weight load borne by the handle grips. Optionally, the feedback signal is provided instantly.

Figure 18A:
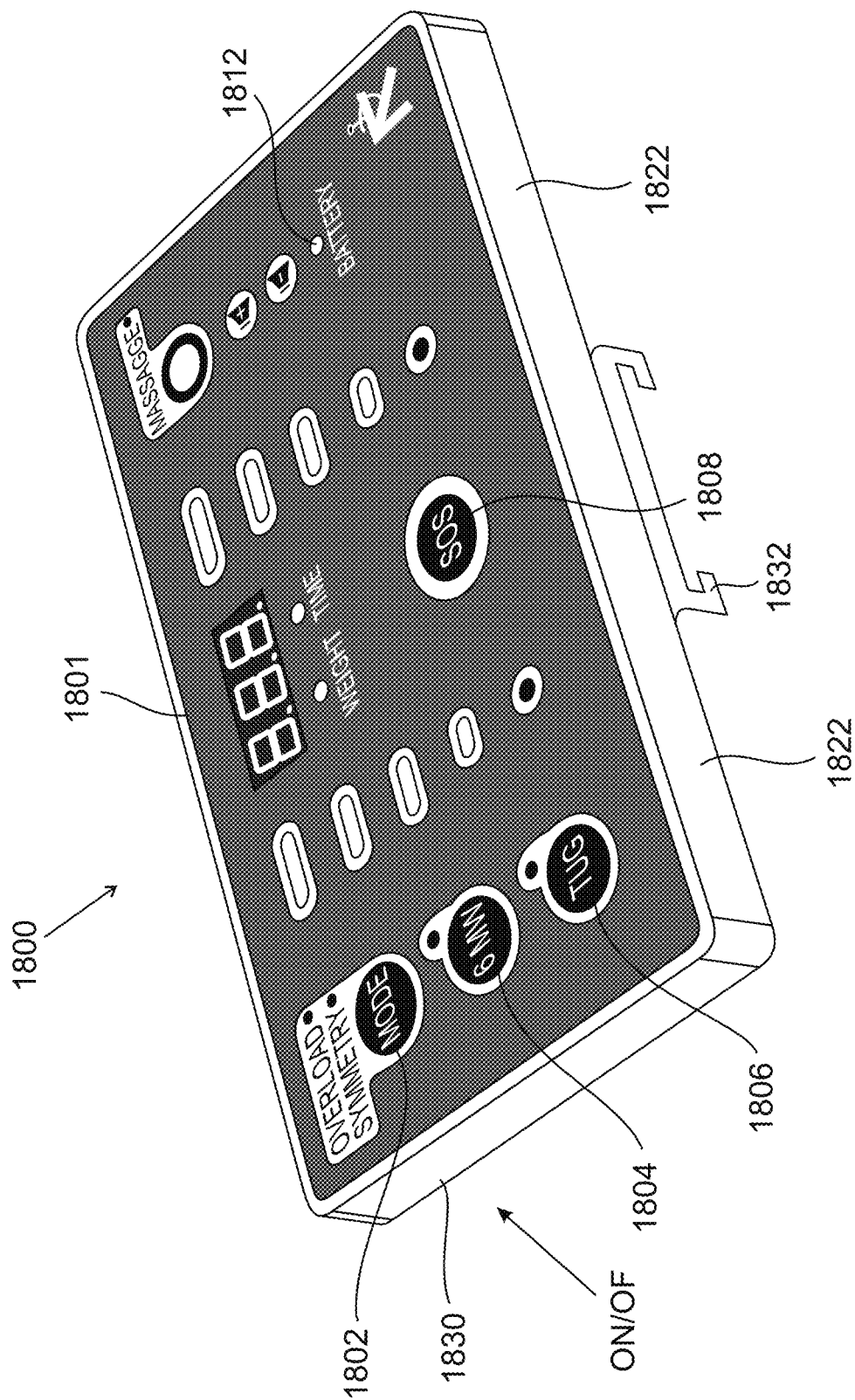
FIG. 18a is a schematic illustration of the buttons, speaker and display screen of a control unit of a walker-assist device showing a sample screen shot on the display screen, according to some embodiments of the invention.

According to some embodiments, the feedback signal may be sent to the patient, for example, through a speaker, headphones and/or a display screen, and/or to a third party monitoring the patient, for example, via a text message. For example, the feedback signal may be appear on a coordinate axis 1804 on screen shot 1802 of display screen 1800 (FIG. 18A). For example, the extent to which the force exerted on one side exceeds the force exerted on the other side may appear as a series of lit up squares, with more squares lit up when the difference is greater. Optionally, the screen may contain additional information such as an indication of the percentage by which the force on one side exceeds the force on the other side and the threshold percentage, i.e., the percentage by which the force on one side may exceed the force on the other side, that has been established for the current use of the walker. Optionally, the threshold percentage may be determined and programmed into the device by, for example, a doctor or physiotherapist treating the user of the walker, and may be changed in accordance with a treatment plan suitable for the user of the walker. Optionally, the determination of the threshold percentage may be based on a standard threshold for all users, for example, a difference of 10-40%, optionally 25%, between the amount of force applied to the right hand grip and the amount of force applied to the left hand grip, according to some embodiments.

Display Screen

In an exemplary embodiment of the invention, walker-assist device 300 of FIG. 3 comprises a Liquid Crystal Display (LCD) screen 344 on the face of control unit 340, according to some embodiments. Screen 344 displays information, for example status and/or feedback on use of the walker. Optionally, screen 344 displays information related to interactive use of the system, for example questions and/or answer choices. Some of the possible display screens are described below in the section entitled "Screen Shots".

In an exemplary embodiment, control unit 340 further comprises buttons 346, 348 and/or 350, allowing the user of the walker or a third party to input information into control unit 340. Optionally, one or more buttons enable one to scroll through choices displayed on screen 344 in response to questions and/or prompts. Answers to prompts are optionally provided by pressing on a touch screen on the display and/or by pressing buttons located around the display screen, according to some embodiments.

Visual Ground Display Feedback

Optionally or alternatively, real time guidance in using the walker is provided by creating a visual display, optionally a walking path] on the ground for a patient to follow. Optionally, the walking path is created by a laser light emanating from the walker-assist device. For example, the laser light creates an image of an arrow on the ground in front of the patient, pointing in the direction that the patient should proceed. Optionally, the arrow may point forward, backward, to the right, to the left, or any angle between those four directions. Optionally, the laser light creates an image of text on the ground in front of the patient, for example, an image of the words, "shift weight to right side." Optionally or alternatively, the image presented on the ground indicates a location to place the foot of the patient and/or of the walker. Optionally, the laser light creates an image of an ellipse on the floor for each leg of the walker, the frequency and duration of appearance of the ellipses to be computer-determined in accordance with a predetermined protocol suitable for the user of the walker depending on his condition. Such a protocol may be particularly advantageous for a particular type of patient using the walker-assist device, for example, a patient suffering from Parkinson's disease or a patient who has suffered a cerebrovascular event and is learning to walk again.

Instant Feedback Signal—Emergency

The data analysis potentially provides the advantage of warning the patient and/or her monitor of a risk of falling or of actual falling, according to some embodiments. For example, the feedback provided at 112 may include an alert signal, which may be sent to the user of the walker, for example, an audio signal sent through a speaker or headphones and/or tactile feedback and/or a visual signal on a display screen, or to a third party monitoring the user of the walker, for example, via a text message. The determination to send an alert signal may be based on a standard threshold for all users, for example, a difference of 10-40%, optionally 25%, between the amount of force applied to the right hand grip and the amount of force applied to the left hand grip, according to some embodiments. For example, the difference in the amount of force measured by two pressure sensitive grips (one on the right side and one on the left side) may indicate the extent of a patient's lack of balance.

Optionally, an alert may be sent in the event of the walker being tilted to one side by more than a predetermined amount, for more than a predetermined amount of time, and for more than a predetermined rate. For example, a walker that is tilted more than 10 degrees, for more than 2 seconds, at a rate of at least 5 times a minute, may indicate that the user of the walker is likely to fall.

Alert Signal

Figure 14:
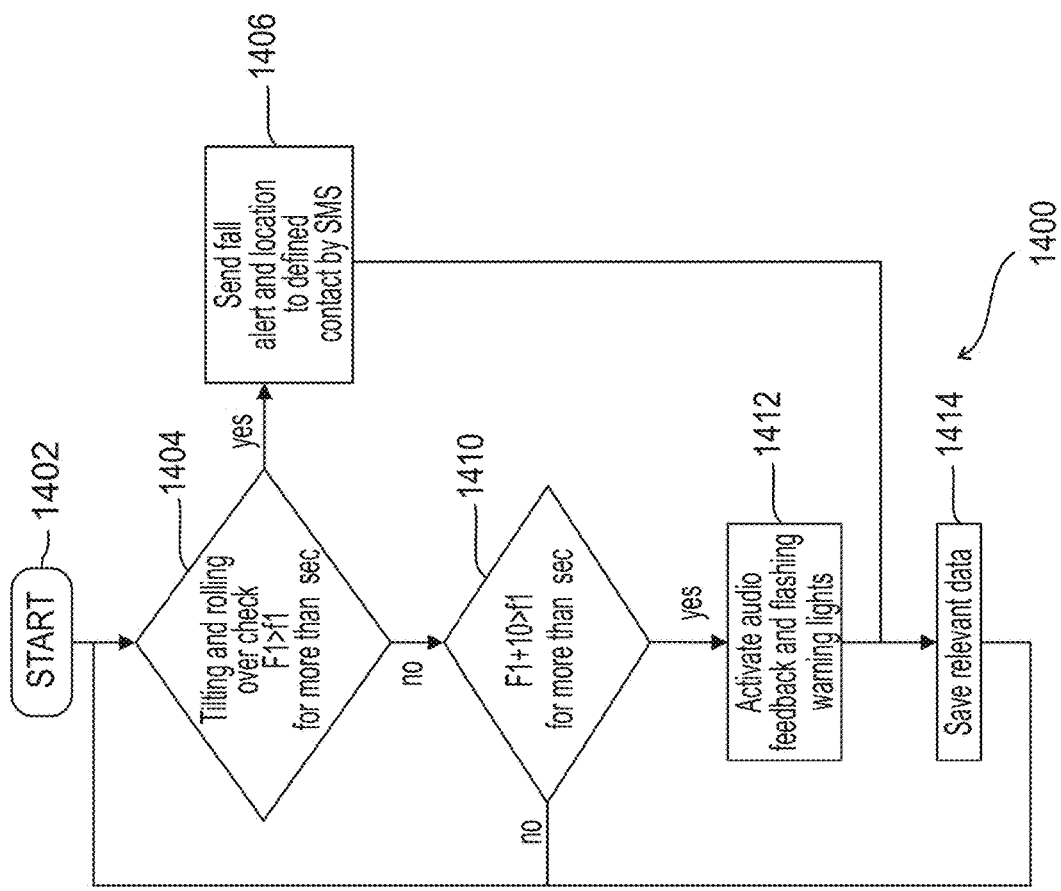
FIG. 14 is a flow chart showing the different acts in the automatic activation of a distress signal in the use of a walker-assist device, according to some embodiments of the invention.

FIG. 14 is a flow chart 1400 showing the different acts in the automatic activation of a distress signal in the use of a walker-assist device, according to some embodiments. For example, a distress signal may be sent when a danger of tilting and/or rolling over is detected.

At 1402, the walker-assist device enters "start" mode, for example, because "start" has been selected and/or the walker-assist device automatically detects movement.

According to some embodiments, after entering "start" mode, the walker-assist device automatically begins checking whether pre-determined tilt thresholds have been exceeded over a pre-determined duration of time. Optionally, pre-determined tilt thresholds for Fall Alerts are established in four directions, F1 (right), F2 (left), F3 (forward) and F4 (backward). For example, the walker-assist device may begin determining whether the actual tilt in the right direction (F1), as measured by the sensors on the walker-assist device, exceeds the pre-determined threshold for tilt in the right direction (f1) 1404. Optionally, it is determined whether the actual tilt in the right direction (F1), as measured by the sensors on the walker-assist device, exceeds the pre-determined threshold for tilt in the right direction (f1) 1404, for more than a preselected amount of time such as, for example, more than 2 seconds.

In an exemplary embodiment, a determination is continuously made as to whether actual tilt exceeds the pre-determined threshold for tilting in all four directions either simultaneously or one after the other in alternating fashion (right, left, forward and backward).

According to some embodiments, if F1 exceeds f1 (and/or F2 exceeds f2 and/or F3 exceeds f3 and/or F4 exceeds f4), an immediate feedback Fall Alert signal will be sent 1006. For example, an SMS message with the location of the walking device may be sent to the third party monitor and/or vibrating elements may be activated inside the hand grip on the side to which the patient is tilting, and/or the words "FALL ALERT: Excessive Tilt to the Right" may be displayed on the display screen.

According to some embodiments, if F1 does not exceed f1, F2 does not exceed f2, F3 does not exceed f3 and F4 does not exceed f4, then the walker-assist device begins determining how close the actual levels are to their respective thresholds. For example, the walker-assist device may determine whether the actual tilt in the right direction (F1), as measured by the sensors on the walker-assist device, reaches a level within 5-35%, optionally 10%, of the pre-determined threshold for tilt in the right direction (f1) 1410. Optionally, the walker-assist device determines whether the actual tilt in the right direction (F1) reaches a level within 5-35, optionally 10, raw units of measurement, of the of the pre-determined threshold for tilt in the right direction (f1).

A similar determination is made for each of the other directions (F2 (left), F3 (forward) and F4 (backward)), according to some embodiments. In an exemplary embodiment, a determination is continuously made as to whether the actual tilt reaches a pre-determined percentage (or comes within a certain number of units of measurement) of the pre-determined threshold for tilting in all four directions, either simultaneously or one after the other in alternating fashion (right, left, forward and backward).

According to some embodiments, if the actual tilt reaches a pre-determined percentage (or comes within a certain number of units of measurement) of the pre-determined threshold for tilting in any of the four directions, an immediate feedback Fall Alert signal will be sent to the patient 1412. For example, active audio feedback and flashing warning lights may be directed at the patient to immediately warn her of a danger of falling. Optionally, vibrating elements may be activated inside the hand grip on the side to which the patient is tilting, and/or the words "FALL ALERT: Excessive Tilt to the Right" may be displayed on the display screen.

According to some embodiments, relevant data regarding any incident, in which the Fall Alert threshold was exceeded or where the measured data is sufficiently close to the set thresholds, is saved. For example, the date, time and measure of the relevant parameters, such as tilt in each direction, may all be saved 1414.

According to some embodiments, these acts are continuously and automatically repeated in order to check for any incident in which the thresholds are exceeded.

Optionally, the system stores data related to incidents in which the thresholds are exceeded, as discussed above, in order to determine a typical behavioral history of a patient who uses the walker. The stored data may also include pressure sensed by both handles, tilting in all directions, speed of movement (determined by GPS), path traveled (determined by GPS), and amount of time and frequency of use of the walker. This behavioral history may be used to prepare a training program for the patient and may allow the system to provide the user of the walker with an alert when movement of the walker is not within a predetermined range of movement parameters for that user.

Tactile Alert

In an exemplary embodiment, tactile feedback, for example vibration, protruding pins and/or electricity, is provided to the patient. Optionally, a vibrating element may be located in the hand grips and/or another part of the walker-assist device. Optionally or alternatively, the vibrating elements may vibrate separately or together. Optionally, a vibrating element may be provided having a nonbalanced motor which rotates with a speed and force controlled by the system.

According to some embodiments, the tactile feedback may be used to indicate that a patient is providing excessive force to the hand grip which is providing the tactile feedback. Optionally or alternatively, the tactile feedback may indicate that an imbalance exceeds a certain threshold and/or that an obstacle is in the patient's path. For example, the hand grip on the side to which a patient is tilting may vibrate, while the hand grip on the other side does not vibrate, as a signal to the patient that she should shift her weight off of the hand grip that is vibrating. Optionally, the force, frequency, speed, or any other quality of the vibration may be varied as desired, to indicate varying types or degrees of alerts.

Manual Alert

According to some embodiments, control unit 340 further comprises alert button 342, which may be activated by a user of a walker to alert a third part monitor that the user of the walker requests assistance.

Figure 15:
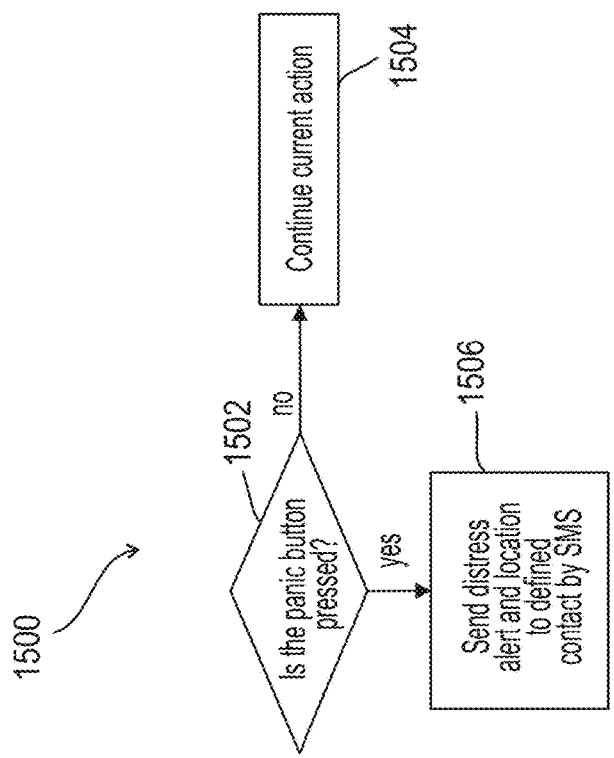
FIG. 15 is a flow chart showing the different steps in the manual activation of a distress signal in the use of a walker-assist device, according to some embodiments of the invention.

FIG. 15 is a flow chart 1500 showing the different acts in the manual activation of a distress signal in the use of a walker-assist device, according to some embodiments.

According to some embodiments, a button is dedicated for functioning as a panic button alert. The dedicated button may be an actual button, for example a button marked "PANIC" and located to the side of the display screen on the control panel, or a "PANIC" prompt located on the display screen which may be touch-activated or may be activated by scrolling through different screen option in order to arrive at and select "PANIC." Alternatively, "PANIC" may be selected by entering a general menu which then includes a "PANIC" prompt.

According to some embodiments, the walker-assist device continuously determines whether "PANIC" is selected 1502. If "PANIC" is not selected, the walker-assist device continues to perform the action it is already performing or, if no action is already being performed, the walker-assist device continues to operate in standby status 1504.

If the walker-assist device determines that "PANIC" has been selected, the walker-assist device then sends a distress signal, for example, an SMS text message, to a third party monitor 1506. Optionally, the distress signal includes a location, for example, as may be determined by a GPS contained within the control box.

Thresholds

According to some embodiments, the computerized processor creates thresholds for each measurement parameter being provided. According to some embodiments, the computerized processor creates a personal profile of a patient based on answers provided to questions which appear as prompts on the display screen and uses this profile to create individualized thresholds suitable to each particular patient.

Sensors

According to some embodiments of the present invention, there is provided a device for retrofitting to a walker which contains sensors measuring at least one physical parameter in the use of a walker and a processor analyzing the obtained measurements and a feedback system. The device may contain sensors such as, for example, pressure sensors or force sensors, for attaching to the hand grips of a walker which sense pressure or force applied to the connection between the hand grips and the walker frame, a computerized processor to analyze the pressure or force measurements and a display screen to indicate the degree of balance or imbalance of the user of the walker (hereinafter "the patient").

When the walker-assist device is first activated, the control panel performs an automatic calibration of each sensor. For example, the sensors will be calibrated when they are not being touched to establish a zero load measurement.

The physical parameters measured include at least one of the amount and/or direction of force applied to the left and right handgrips of the walker, the balance of the walker and/or the speed, acceleration, acceleration in at least one dimension/direction, gait, blood oxygen saturation and/or force, variability and/or rapidity of the pulse of the patient. According to some embodiments, pressure sensors, force sensors, electro-optical sensors, an imbalance sensor, a tilt sensor, a gyroscope, an accelerometer, an oxygen sensor, a pulsometer, a laser scanner and/or other sensors are retrofitted to a walker and transmit data they measured to a computerized processor which analyzes the data and provides feedback to a patient and/or to a third party. For example, electro-optical sensors may be used to measure walking speed and distance walked by counting the number of turns of wheels on the walker. The electro-optical sensors may be placed on the walker frame and aimed at the wheels, and a beam transmitted by the sensor may be reflected back from the wheels as they turn, providing an indication of several parameters including, for example, the number of turns of the wheels and the speed of turning of the wheels.

Pressure Sensors and Force Sensors

According to some embodiments of the present invention, a mechanical sensor such as, for example, a pressure sensor, a force sensor, or a strain gauge, is located in (or on) at least one hand grip on the side of the walker. According to some embodiments, sensors 204 and 206 obtain measurements on the two side grips (the left hand grip and the right hand grip) of walker 220, i.e., the weight applied to the side grips is measured. Optionally, the obtained measurements are compared by the computerized processor of the walker-assist device.

According to some embodiments, sensors 204 and 206 are tape contained sensors such as, for example, piezoelectric sensors, strain gauges, and resistive film sensors. One example of a strain gauge is model J2A-XX-S 1425-35B, manufactured by Vishay Precision Group of Wendell, N.C., USA.

Optionally, for a walker having wheels (see FIG. 2a), sensors 204 and 206 may be placed on the outer surface of the wheels. Alternatively, walker 220 may have four legs and no wheels and sensors 204 and 206 may be disc shaped sensors, for example, placed on the bottoms of the two front legs of walker 220.

In an exemplary embodiment, sensors 204 and 206 are integrated into hand grips 210 and 212, respectively. Optionally or alternatively, sensors 204 and 206 are located in hand grip covers which slide onto hand grips 210 and 212, respectively. Optionally, sensors 204 and 206, and/or the covers or film of tape which contain them are waterproof, washable and/or flexible to torsion and/or bending.

Exemplary sensors for use with the walker-assisted device as described herein are piezoresistive sensors such as, for example, UPX3/CHR100, manufactured by SHR Automation Technology Co., Ltd. (China); pressure sensors such as, for example, MS5541, manufactured by Measurement Specialties Inc.; force sensitive sensors such as, for example, FSR, manufactured by Versapoint Ltd.; and MEMS sensors, for example, LM series sensors, manufactured by Measurement Specialties Inc. Each sensor is configured according to the portion of the walker to which it is to be attached such as, for example, a sensor in a film of tape or a sensor to be attached to the bottom of a leg of a walker.

In an exemplary embodiment, the pressure sensitive grips measure force load along a longitudinal axis and along a lateral axis.

Plurality of Pressure Sensors on Each Grip

In an exemplary embodiment of the invention, walker-assist device 300 comprises pressure sensors 322, 324 on left hand grip 320 and pressure sensors 326 and 328 on right hand grip 330. Pressure sensors 324 and 328 face the top of the handgrips, while pressure sensors 322 and 326 face the side of the handgrips, according to some embodiments. The top and side locations of the pressure sensors increase the accuracy of the measurement of the direction of the force applied to the hand grips. As discussed herein, the pressure sensors measure weight applied by the user of the walker to the each of the sides of the walker. Tilting of the walker, as discussed herein, is measured by tilt sensors which are separate from the pressure sensors.

Measuring Imbalance

At 102 and 104, a person using a walker 220 places his right hand on right hand grip 210 of walker 220 (step 102) and his left hand on left hand grip 212 of walker 220 (step 104). In placing his hands on grips 210 and 212, the person will also be placing his hands on pressure sensor 204, embedded in tape which is affixed to right hand grip 210, and on pressure sensor 206, embedded in tape which is affixed to left hand grip 212.

At 106, pressure sensors 204 and 206 measure the amount of force applied to right hand grip 210 and left hand grip 212, respectively, and transmit that data (108) to computerized processor 208, which is embedded in and/or held by a film of tape connecting pressure sensor 204 and pressure sensor 206. Optionally, the part of the film of tape 202 containing computerized processor 208 attaches to front cross bar 214 of walker 220.

Analysis of Imbalance Data

Computerized processor 208 analyzes the data received from pressure sensors 204 and pressure sensor 206 (110) and transmits feedback (112) to the user of the walker (the "patient") or to a third party monitor of the user.

According to some embodiments, computerized processor 208 may analyze (110) the difference in the amount of force measured by the pressure sensors on the right and left hand grips to determine the degree of stability of the user of the walker and the degree of imbalance of the user and/or of the walker.

Optionally, feedback related to the imbalance data is provided to the patient and/or to an excessive amount of weight applied to either or both hand grips is provided to the patient in the form of at least one of sensed feedback, visual feedback, and acoustic feedback. The feedback is intended to indicate to the patient the need to reduce the amount of weight applied to at least one of the hand grips. Optionally, if there is excessive weight applied to a particular one of the hand grips, feedback provided to the patient may include vibration sensed at that particular hand grip.

In an exemplary embodiment, the data is analyzed to provide instructions to the patient or the third party monitor on how to stabilize the patient's gait. Optionally, the data analysis includes the creation of a rehabilitation plan for the patient.

Laser Scanner

Optionally or alternatively, the vibrating elements vibrate, separately or together, to warn of an imbalance and/or of an obstacle detected by the laser scanner in the patient's path. Alternatively, a portable communication device used in conjunction with the system of the present invention, may allow a patient to scan the area near the walker, thereby providing a picture thereof.

Gyroscope

According to some embodiments, a gyroscope provides measurements of orientation. Optionally, the measurements of orientation include forward/backward orientation, left/right orientation and up/down orientation. Optionally, the gyroscope is optionally located inside control unit 340. Optionally and/or alternatively, the determination of a patient's balance or imbalance is based on the measurements of the amount and direction of force applied to the hand grips and/or the measurements of orientation provided by the gyroscope.

Accelerometer

According to some embodiments, the walker-assist device further comprises sensors obtaining movement and/or acceleration data on a person using a walker, in addition to imbalance data. In an exemplary embodiment, the walker-assist device further comprises an accelerometer. Optionally, the accelerometer measures a patient's movement and acceleration in gait in three axes: longitudinal, lateral and vertical. As used herein, the axes are respectively referred to as a roll rotation, an elevation rotation and a yaw rotation (azimuth). Utilizing this convention, a roll rotation refers to acting about the longitudinal axis; an elevation rotation is acting about the lateral axis and a yaw rotation is acting about the vertical axis.

According to some embodiments, the movement and acceleration parameters include three axes in a three-dimensional space adopting the alta-azimuth coordinate system. The figures describe an exemplary feedback device 300 in a three-dimensional space and three orthogonal axes of rotation about the walker's center of mass: a longitudinal axis, a lateral axis and a vertical axis. According to some embodiments, the imbalance parameter includes two of the axes: longitudinal axis 104 and lateral axis 106.

GPS Monitor

In an exemplary embodiment, the control unit 340 of the walker-assist device 300 further comprises a GPS monitor which detects a patient's location over time, providing movement and/or speed data and/or path information. Optionally, the GPS monitor also provides a location of the walker to a third party monitor, for example, when an alert signal is generated.

Biomeasurements

In an exemplary embodiment, hand grip 320 and/or hand grip 330 of the walker-assist device 300 further comprises at least one oxygen sensor and/or at least one pulsometer, measuring the variability and/or rapidity of the pulse of the patient. According to some embodiments, a patient's blood oxygen saturation levels and/or heart rate are measured. Alternatively a separate sensor is provided. This may, however, be less desirable as it may cause the patient to let go of the walker and possibly fall.

Processor

According to some embodiments, the collected data is analyzed by a computerized processor, located inside control unit 340. Optionally, the computerized processor transmits feedback to the patient via display screen 344 and/or to a third party monitoring the patient's walking. Optionally, the processor transmits feedback via direct wiring to a display screen, a modem and/or a Bluetooth device.

According to some embodiments, the computerized processor comprises a PC card. Optionally, the computerized processor is coupled to a memory. Optionally, the memory is a flash memory, indelible flash memory, memory card, SD expansion card, or other portable memory device. Optionally or alternatively, the processor is located on a remote computer.

Personalized Monitoring

According to some embodiments, in addition to the basic function of sensing the weight applied to each side of the walker by means of the walker-assist device, as discussed herein, the computerized processor creates and/or modifies (e.g., one created by a therapist) a personal profile of a patient based on the input of personal information of the user of the walker in response to prompts appearing on the display screen 344, as described below in the section entitled Screen Shots, and/or on previously recorded data from the user's use of the walker-assist device.

In an exemplary embodiment, thresholds suitable to each individual user are determined, progress is tracked and the computerized processor provides personalized guidance to the patient. Optionally, detailed feedback, including a learning system and instruction in real time, are provided.

In an exemplary embodiment, the computerized processor provides a feedback signal comprising instant, personalized instructions to the user which change as parameter measurements change. For example, the instructions may state, "shift some of your weight to your left side," "move your right foot forward," "take two steps forward," "walk 3 meters forward," and/or "walk for 10 minutes." Optionally, the instructions are based on the user's personal profile, the user's stage of rehabilitation, the thresholds determined for the patient, the patient's performance since the beginning of her use of the walker-assist device and/or the patient's performance during the rehabilitation session in which the patient is performing.

Rehabilitation Plan

According to some embodiments, different thresholds, for activating an alert signal and/or for activating a non-emergency signal, are established for different stages of rehabilitation of a user. These different stages may include, for example, Phase I—standing with equal weight distribution; Phase IIa—standing with one's weight on his "stronger" side and extending the weaker leg; Phase IIb—standing with one's weight on his "weaker" side and extending the stronger leg forward; Phase IIIa—walking short distances, and/or Phase IIIb—walking long distances. Optionally, thresholds within each phase of rehabilitation may be set based on a standard threshold for all users. Optionally or alternatively, the computerized processor creates thresholds suitable to each individual user, within each phase of rehabilitation, based on the input of personal information of the user, as described below in the section entitled Screen Shots, and/or on previously recorded data from the user's use of the walker-assist device. In embodiments, a computer program includes a management program which includes feedback parameters and thresholds for the patient that is programmed into the control unit. As discussed herein, in embodiments, the feedback parameters may be adapted for each particular patient and then programmed into the control unit. In an exemplary embodiment, the thresholds are automatically updated in real time on the basis of the patient's past and/or current performance.

Rehabilitation

In an exemplary embodiment, the walker-assist device provides guidance specific to different phases of rehabilitation that a user of a walker may pass through during her rehabilitation. For example, the walker-assist device may establish and provide different thresholds for different stages of rehabilitation of a patient, for example, standing with equal weight distribution, standing with weight on a user's weaker side, extending one's stronger leg, walking short distances, and/or walking long distances.

According to some embodiments, a user of a walker may progress through the below described phases of rehabilitation, beginning with Phase I. Optionally, a user of a walker may begin her rehabilitation at a stage more advanced stage than Phase I. Optionally, a user of a walker may skip at least one of the above described phases of rehabilitation as she proceeds towards the final phase. In an exemplary embodiment, the thresholds are automatically updated in real time on the basis of the patient's performance throughout her use of the walker-assist device, during her use of the device in the particular stage of rehabilitation in which she is currently and/or during the session in which she is currently using the walker-assist device. The device may store data at a predetermined rate and may store data related to parameters which have exceeded predetermined thresholds.

Phase I: Standing with Two Sided Support

Figure 4:
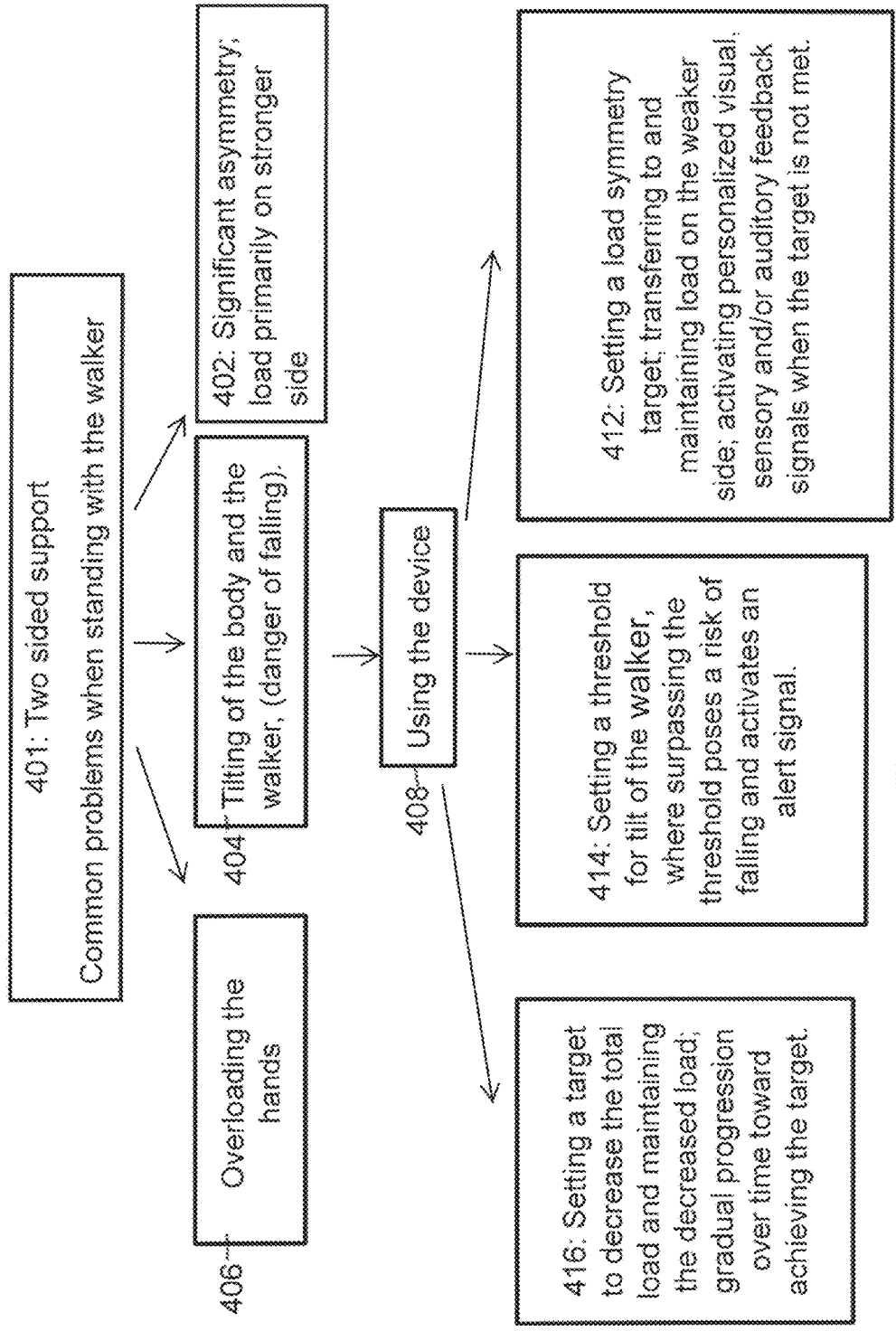
FIG. 4 is a flow chart demonstrating the use of the walker-assist device of FIG. 3 in the acute phase (Phase I) of rehabilitation of a person with walking difficulties, according to some embodiments of the invention.

FIG. 4 is a flow chart 400 demonstrating the use of the walker-assist device of FIG. 3 in the acute phase (Phase I) of rehabilitation of a person with walking difficulties, according to some embodiments. In this acute phase, a patient attempts to stand while holding the walker and placing her weight on both legs 401, without walking and without shifting her weight to one side.

Potential problems experienced by patients in this phase may include significant asymmetry in the placement of load 402, tilting of the patient and/or the walker (and corresponding danger of falling) 404 and excessive weight bearing by one or both hands 406.

These potential problems are optionally addressed in the use of the device 408 as follows, according to some embodiments: Asymmetry of load 402 is addressed by setting a load symmetry target; transferring the load to the weaker side and maintaining the load on that weaker side; and activating personalized visual, sensory and/or auditory feedback signals when the target is not met (412).

Tilting 404 is optionally addressed by setting a threshold for tilt of the walker, where surpassing the threshold poses a risk of falling and activates an alert signal 414. Overloading 406 is addressed by setting a target to decrease the total load and maintaining the decreased load with gradual progression over time toward achieving the target (416).

Phase IIa: Standing on Stronger Leg

Figure 5:
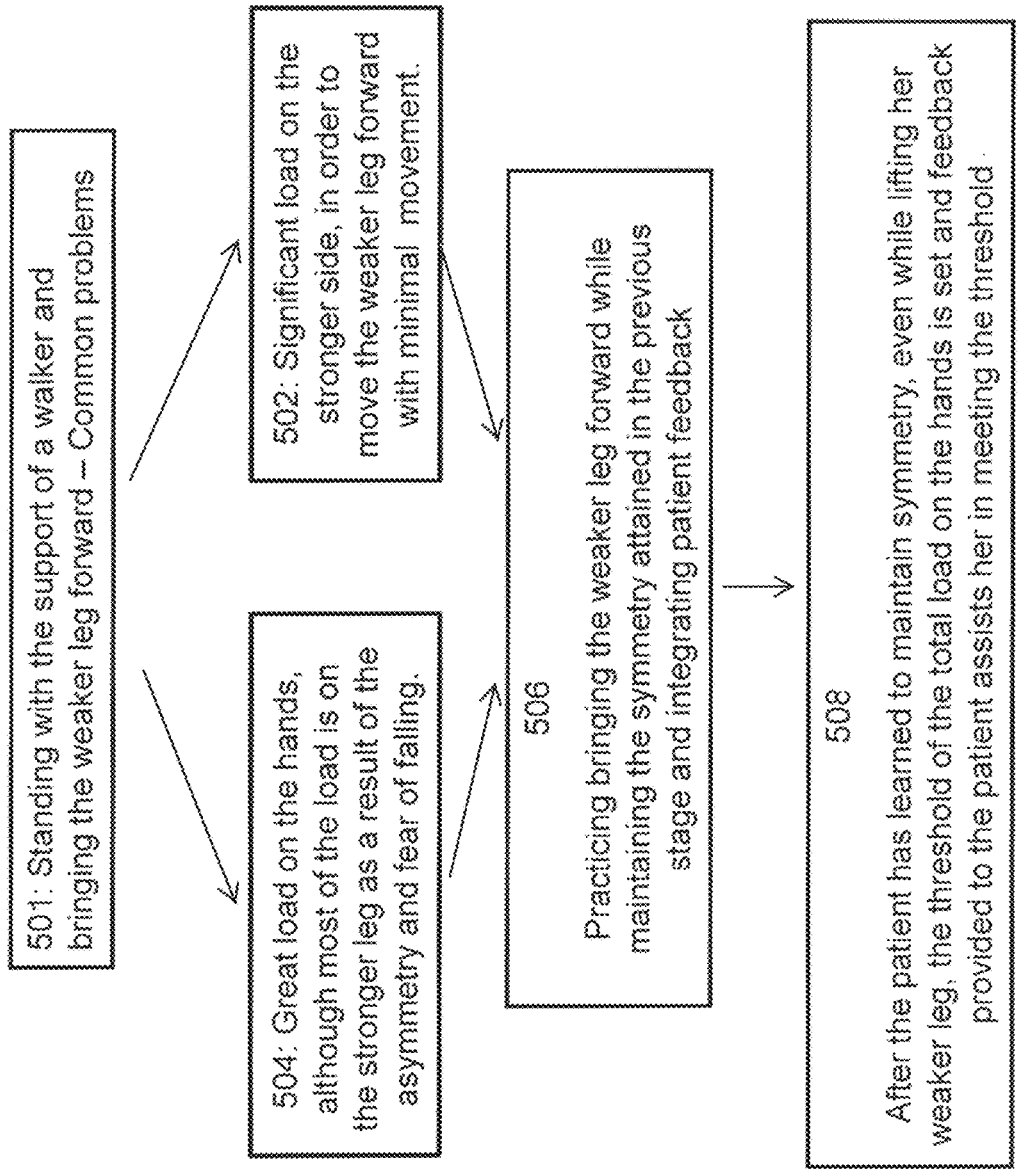
FIG. 5 is a flow chart demonstrating the use of the walker-assist device of FIG. 3 in the walking preparation phase (Phase IIa) of rehabilitation of a person with walking difficulties, according to some embodiments of the invention.

FIG. 5 is a flow chart 500 demonstrating the use of the walker-assist device of FIG. 3 in the walking preparation phase (Phase IIa) of rehabilitation of a person with walking difficulties, according to some embodiments. In this walking preparation phase, a patient prepares for walking by placing her weight on her "stronger side," defined as the side more capable of bearing weight, and brings her weaker leg forward (501), according to some embodiments.

Potential problems experienced by patients in this phase may include, at 502, significant load on the patient's stronger side, as a patient attempts to move her weaker leg forward while minimizing the use of her weaker side. An additional potential problem may include an excessive load on the hands 504. This excessive load on the hands may occur even when most of the load is on the stronger leg as a result of the asymmetry and the patient's fear of falling.

Significant load on the patient's stronger side 502 and excessive load on the hands 504 may both be initially addressed by directing the patient to practice bringing her weaker leg forward while maintaining the symmetry attained in the previous stage while integrating patient feedback 506 (using the device of FIG. 3).

Subsequently, significant load on the patient's stronger side 502 and excessive load on the hands 504 may both be addressed by setting the threshold of the total load on the hands and providing feedback to the patient to assist her in meeting that threshold 508. Optionally, step 508 takes place only after the patient has learned to maintain symmetry while standing, even while lifting her weaker leg and using her "stronger side" to support herself, without walking.

Phase IIb: Standing on Weaker Leg

Figure 6:
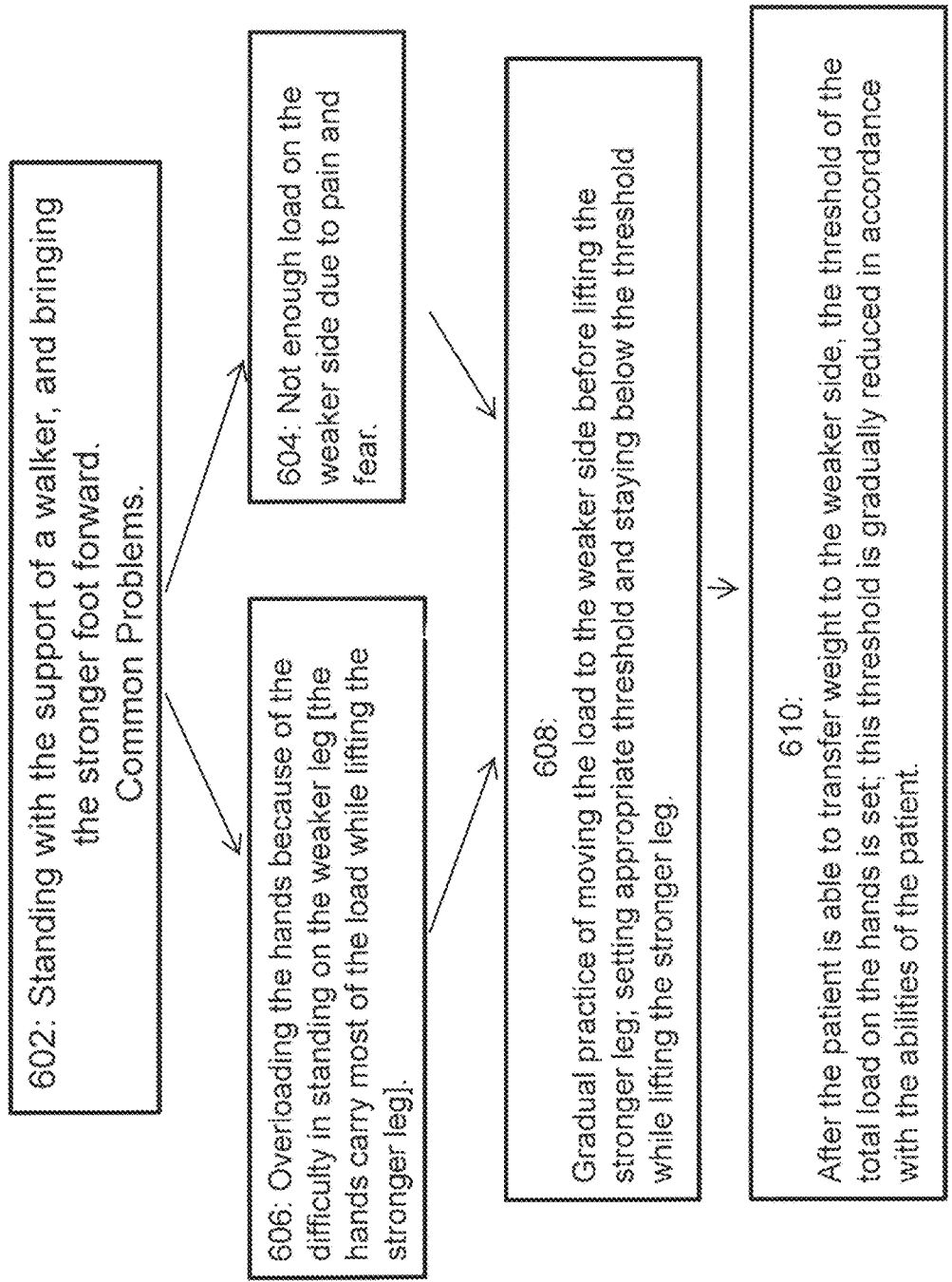
FIG. 6 is a flow chart demonstrating the use of the walker-assist device of FIG. 3 in the weak side support phase (Phase IIb) of rehabilitation of a person with walking difficulties, according to some embodiments of the invention.

FIG. 6 is a flow chart 600 demonstrating the use of the walker-assist device of FIG. 3 in the weak side support phase (Phase IIb) of rehabilitation of a person with walking difficulties, according to some embodiments. In this weak side support phase, a patient stands with the support of a walker and brings her stronger leg forward while supporting herself with her weaker leg (602).

Potential problems experienced by patients in this phase may include insufficient load on the weaker side, for example, due to pain and fear (604). Another potential problem may be overloading the hands, for example, due to the difficulty of standing on the weaker leg, potentially causing the hands to carry most of the load when lifting the stronger leg (606).

Insufficient load on the weaker side 604 and overloading the hands 606 may both be initially addressed by the gradual practice of moving the load to the weaker side before lifting the stronger leg; setting an appropriate threshold and staying below the threshold while lifting the stronger leg (e.g., using the device of FIG. 3) 608. While lifting the stronger leg, the patient will stay below the threshold only if he puts enough weight on his weaker leg, i.e., he does not put too much weight on his hands.

Subsequently, after the patient is able to transfer weight to the weaker side, insufficient load on the weaker side 604 and overloading the hands 606 may both be addressed by setting a new threshold of the total load on the hands and gradually reducing that threshold in accordance with the abilities of the patient 610.

Phase IIIa: Walking Short Long Distances

Figure 7:
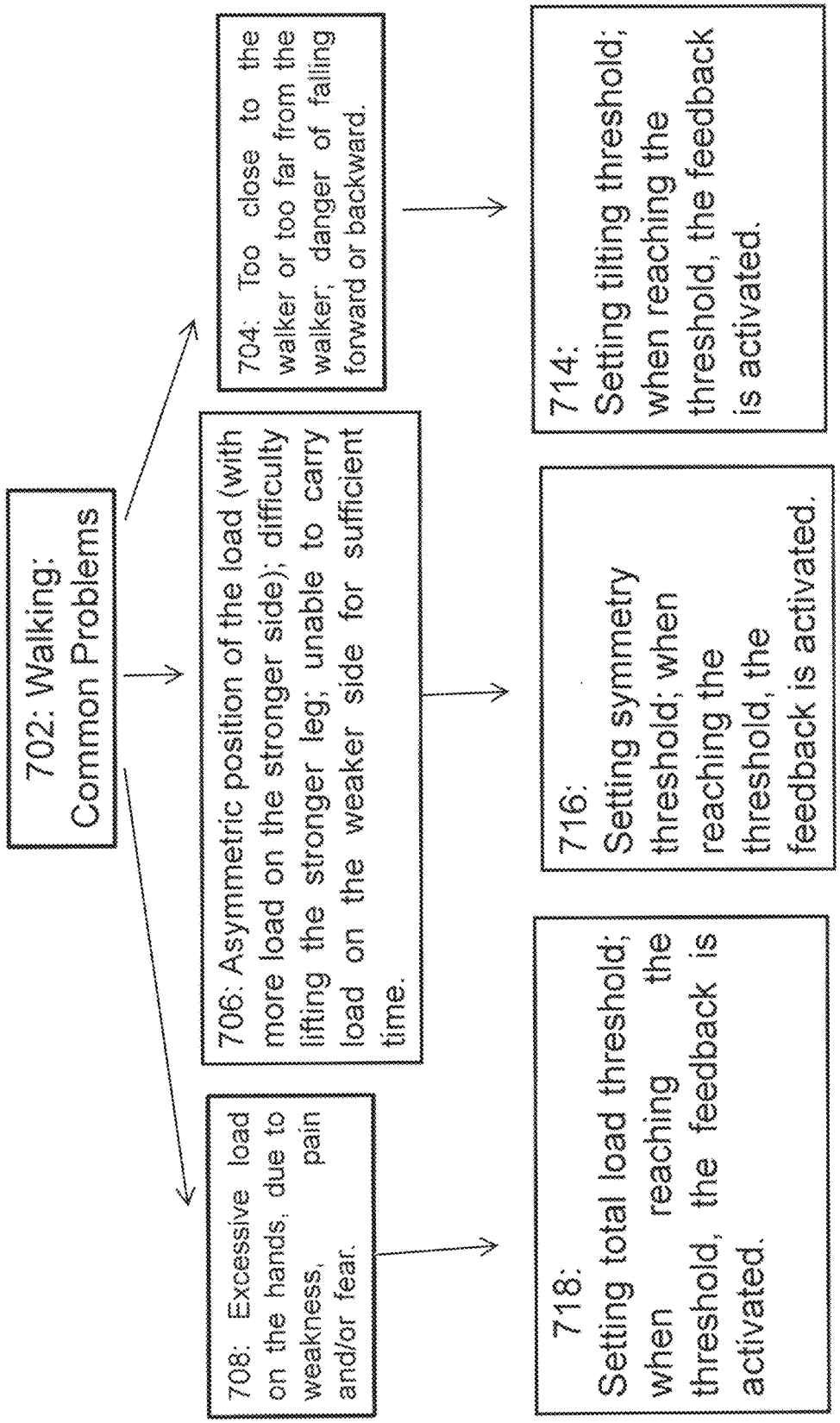
FIG. 7 is a flow chart demonstrating the use of the walker-assist device of FIG. 3 in the short distance walking phase (Phase IIIa) of rehabilitation of a person with walking difficulties, according to some embodiments of the invention.

FIG. 7 is a flow chart 700 demonstrating the use of the walker-assist device of FIG. 3 in the short distance walking phase (Phase IIIa) of rehabilitation of a person with walking difficulties, according to some embodiments. In this short distance walking phase, a patient walks short distances with the support of a walker alternating between taking a step by bringing her stronger leg forward and taking a step by bringing her weaker leg forward 702.

Potential problems experienced by patients in this phase may include placing the body of the patient too close to the walker or too far from the walker, potentially causing a danger of falling forward or backward, respectively 704.

Another potential problem may be asymmetric position of the load (with more load on the stronger side), potentially making it difficult to lift the stronger leg when the patient is unable to carry sufficient load on her weaker side for sufficient time 706.

Another potential problem may be the placement of excessive load on the hands, for example, as a result of weakness, pain and/or fear 708.

Placing the body of the patient too close to the walker or too far from the walker 704 may be addressed, at 714, by setting a threshold for tilting and configuring the system to send a feedback signal to the patient and/or her monitor when that tilting threshold is reached (using the device of FIG. 3).

Asymmetric position of the load 706 may be addressed, at 716, by setting a symmetry threshold and configuring the system to send a feedback signal to the patient and/or her monitor when that symmetry threshold is reached (using the device of FIG. 3).

Excessive load on the hands 708 may be addressed, at 718, by setting a total load threshold and configuring the system to send a feedback signal to the patient and/or her monitor when that total load threshold is reached to alert the patient and/or her monitor to the need to reduce the load on the hands.

Phase IIIb: Walking Long Distances

Figure 8:
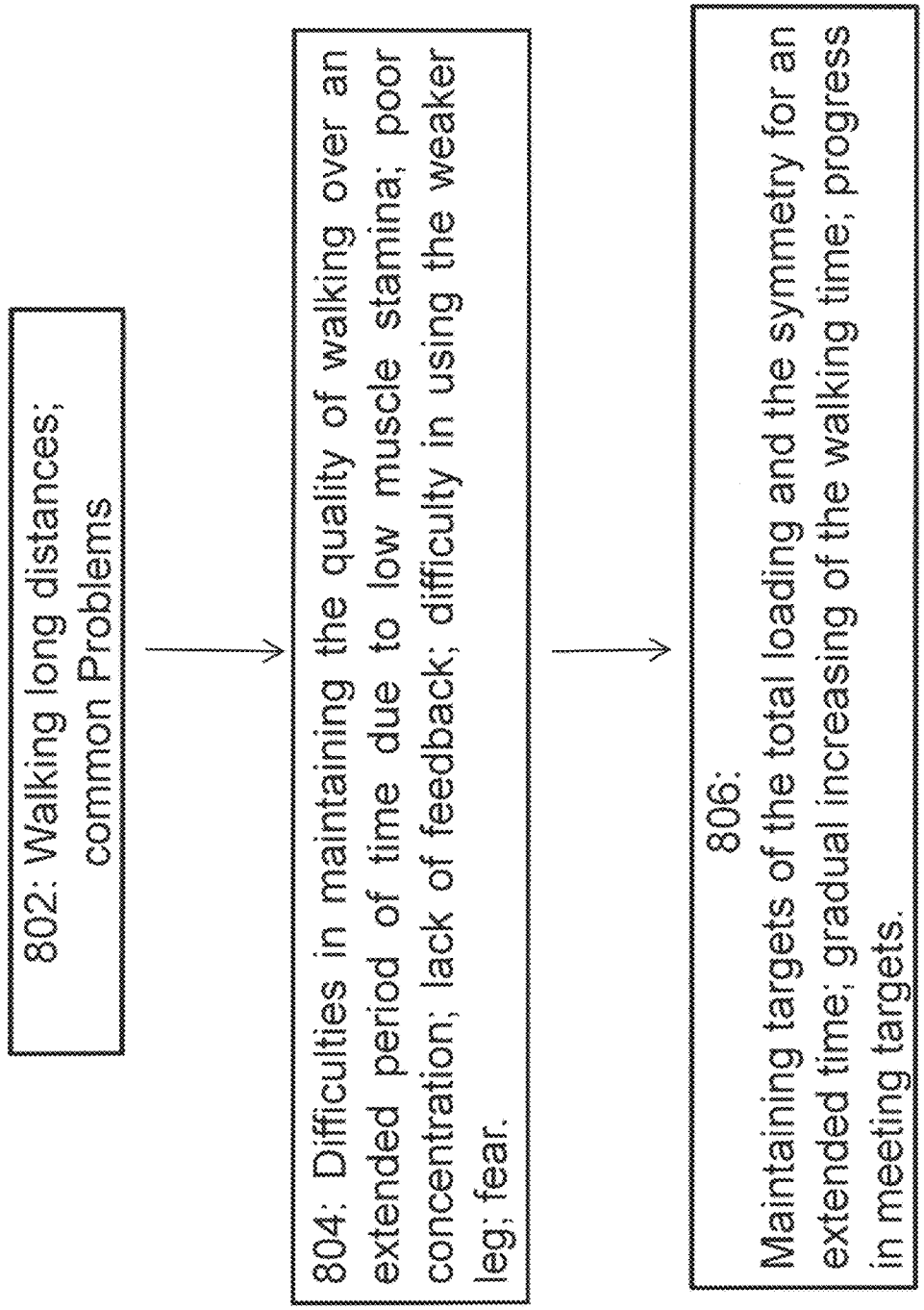
FIG. 8 is a flow chart demonstrating the use of the walker-assist device of FIG. 3 in the long distance walking phase (Phase IIIb) of rehabilitation of a person with walking difficulties, according to some embodiments of the invention.

FIG. 8 is a flow chart 800 demonstrating the use of the walker-assist device of FIG. 3 in the long distance walking phase (Phase IIIb) of rehabilitation of a person with walking difficulties, according to some embodiments. In this long distance walking phase, a patient walks long distances with the support of a walker alternating between taking a step by bringing her stronger leg forward and taking a step by bringing her weaker leg forward 802.

Potential problems experienced by patients in this phase may include, at 804, difficulties in maintaining the quality of walking over an extended period of time, for example, due to low muscle stamina; poor concentration; lack of feedback; difficulty in using the weaker leg and/or fear.

Difficulties in maintaining the quality of walking over an extended period of time 804 may be addressed, at 806, by assisting the patient to maintain targets of the total loading and the symmetry for an extended time; to gradually increasing walking time; and progress in meeting the targets, according to the ability of the individual patient (using the device of FIG. 3).

Connecting Port

According to some embodiments, outlet 352 is a USB port configured to accept a USB cable which connects outlet 352 to computer 382. Optionally, the USB cable also acts as a charger for walker-assist device 300. Computer 382 contains a processor, a memory coupled to the processor and a power supply cable 380. Optionally, software 384 is provided separately for uploading to computer 382 for interaction with the walker-assist device. Optionally or alternatively, the walker-assist device contains plug and play software.

Calibrating Walker-Assist Device

Figure 9:
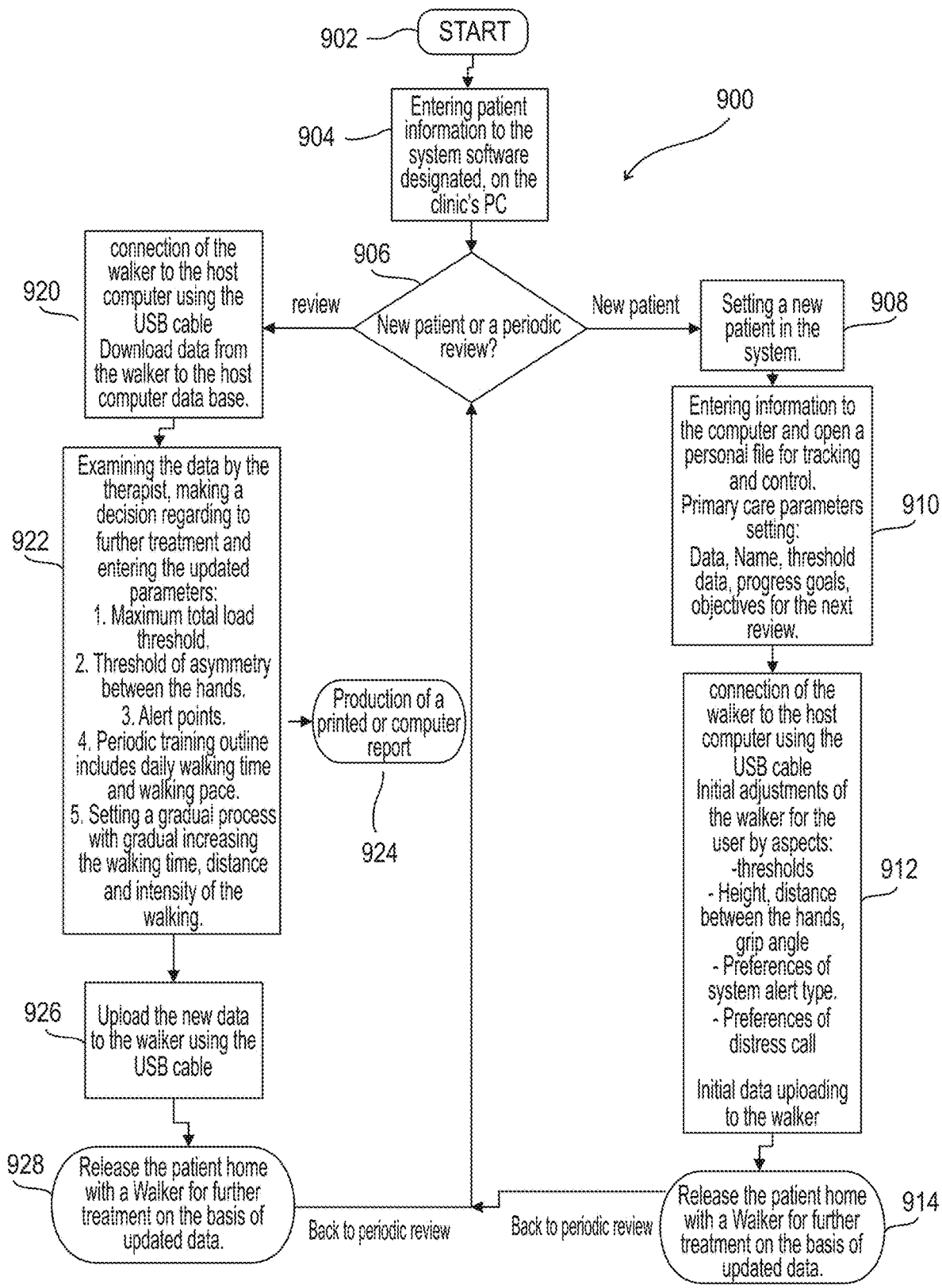
FIG. 9 is a flow chart showing the different acts in the calibration of a walker-assist device and/or walker, according to some embodiments of the invention.

FIG. 9 is a flow chart 900 showing the different acts in the interfacing of the walker-assist device of FIG. 3 with a computer processor, according to some embodiments. At 902, the display screen of the walker-assist device displays a "start" prompt. Selecting "start" leads to a prompt 904 asking whether patient information will be entered, in order to be transmitted to the system software designated on the clinic's computer system.

The display screen then asks whether the patient is a new patient or an existing patient who is undergoing a periodic review 906. If "new patient" is selected, a new patient profile is created 908 followed by the entering of additional information and the opening of a personal file for tracking and control of the new patient. Primary care parameters are also set, including date, name, threshold data, progress goals and/or objectives for the next review 910, according to some embodiments.

According to some embodiments, the walker-assist device then transmits patient data to the host computer at the clinic via a USB cable, wireless connection, flash drive and/or other means of connection 912. Initial adjustments of the walker-assist device and/or walker are optionally made at this point for the particular patient whose data has been received. These adjustments may include choosing thresholds, choosing system and alert and distress call preferences, selecting the height of the walker, distance between the side grips and the angles of the side grips (when the walker is adjustable) and/or calibrating that information in the computer system. The information created by the computer is then uploaded to the walker-assist device. For example, the computer processor may analyze the data and send feedback to control unit 340.

According to some embodiments, some or all of the computing processes are performed by a computerized processor located inside the walker-assist device. Optionally or alternatively, some or all of the computing processes are performed by a computerized processor located in a smart phone device. Optionally or alternatively, some or all of the computing processes are performed by a computerized processor located in a remote location. For example, the computerized processor may be located at a clinic while the walker-assist device may be located in a patient's home. Alternatively, the computerized processor may be located in a remote location while the walker-assist device may be located in a clinic. Optionally or alternatively, the computerized programming takes place in a cloud, such as an Internet cloud.

According to some embodiments, the patient then begins use of the walker-assist device, as it has been calibrated, away from the clinic 914. Alternatively, the patient then begins use of the walker-assist device, as it has been calibrated, in the clinic. On the patient's next visit to the clinic, upon reaching prompt 906, "periodic review" will be selected instead of "new patient."

After selecting "periodic review," data stored in the walker-assist device is downloaded to the computer in the clinic or to a remote computer or smart phone via a USB cable, wireless connection, flash drive and/or other means of connection 920.

According to some embodiments, the data is then analyzed by the computerized processor and reviewed by a therapist 922. According to some embodiments, a decision is made regarding further treatment and parameters and/or thresholds for any further treatment are updated. These thresholds may include maximum total load threshold, threshold for asymmetry between the hands and alert thresholds. Optionally, a training outline is updated, including daily walking time and/or pace. For example, a training outline may be established to set gradually increasing goals for walking time, walking distance and walking intensity.

According to some embodiments, these updated parameters, thresholds and/or training outlines and/or goals are then uploaded to the walker-assist device via a USB cable, wireless connection, flash drive and/or other means of connection 926. According to some embodiments, the patient then continues use of the walker-assist device, as it has been re-calibrated, away from the clinic 928. Alternatively, the patient then begins use of the walker-assist device, as it has been calibrated, in the clinic.

Automatic Feedback Activation

Figure 10A:
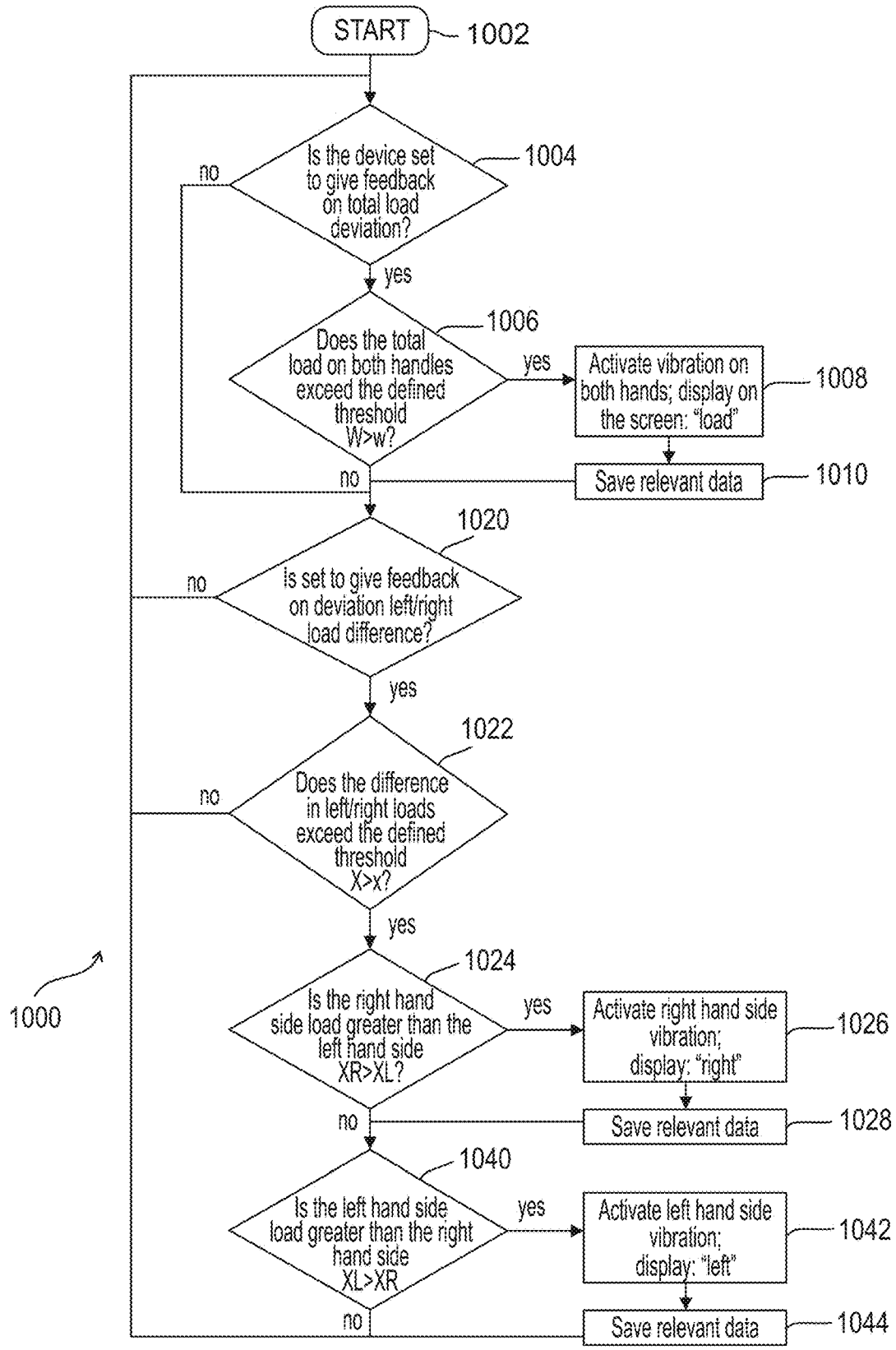
FIGS. 10a and 10b are flow charts showing the different acts in the automatic determination of whether thresholds have been exceeded in the use of a walker-assist device, according to some embodiments of the invention.

FIG. 10A is a flow chart 1000 showing the different acts in the automatic generation of feedback in the regular use of the walker, according to some embodiments. At 1002, the walker-assist device enters "start" mode, for example, because "start" has been selected and/or the walker-assist device automatically detects movement.

According to some embodiments, after entering "start" mode, the walker-assist device automatically begins checking whether pre-determined thresholds have been exceeded. For example, the walker-assist device may begin by determining whether a total load threshold (w) has been set 1004. If the walker-assist device does have a total load threshold setting then the device checks whether the actual total load (W) measured by the sensors on the walker-assist device exceeds that threshold (w) 1006.

According to some embodiments, if W exceeds w, an immediate feedback signal will be sent 1008. For example, vibrating elements may be activated inside both hand grips and/or the words "excessive load" may be displayed on the display screen. Optionally, relevant data regarding the incident in which the threshold was exceeded may be saved, for example the date, time and measure of the relevant parameters, such as load on the left side and load on the right side 1010.

According to some embodiments, if a total load threshold was not set when reaching 1004, the walker-assist device then determines whether a deviation threshold (x) has been set for the difference between the left and right loads 1020. If a total load threshold was set, then determining whether a deviation threshold has been set 1020 takes place after determining that a total load threshold was not exceeded 1006 or after saving data regarding the exceeding of a total load threshold 1010.

If the walker-assist device does have a load deviation threshold setting (x), then the device checks whether the actual total load deviation (X) measured by the sensors on the walker-assist device exceed the set threshold (x) 1022.

According to some embodiments, if X exceeds x, the walker-assist device then determines whether the load on the right side load is greater than the load on the left side 1024. If the load on the right side load is greater than the load on the left side, an immediate feedback signal will be sent indicating that the right side load is too large 1026. For example, vibrating elements may be activated inside the right hand grip and/or the words "excessive load on RIGHT side" may be displayed on the display screen. Optionally, relevant data regarding the incident in which the threshold was exceeded may be saved, for example the date, time and measure of the relevant parameters, such as load on the left side and load on the right side 1028.

According to some embodiments, if the load on the right side load is not greater than the load on the left side, the walker-assist device checks whether the load on the left side is greater than the load on the right side 1040. If the load on the left side is greater than the load on the right side, an immediate feedback signal will be sent indicating that the left side load is too large 1042. For example, vibrating elements may be activated inside the left hand grip and/or the words "excessive load on LEFT side" may be displayed on the display screen. Optionally, relevant data regarding the incident in which the threshold was exceeded may be saved, for example the date, time and measure of the relevant parameters, such as load on the left side and load on the right side 1044.

According to some embodiments, these acts are continuously and automatically repeated in order to check for any incident in which the thresholds are exceeded. Optionally, one or more other thresholds, for example thresholds for the speed, acceleration, gait, blood oxygen saturation and/or force, variability and/or rapidity of the pulse of the patient, are checked in a similar fashion.

Figure 10B:
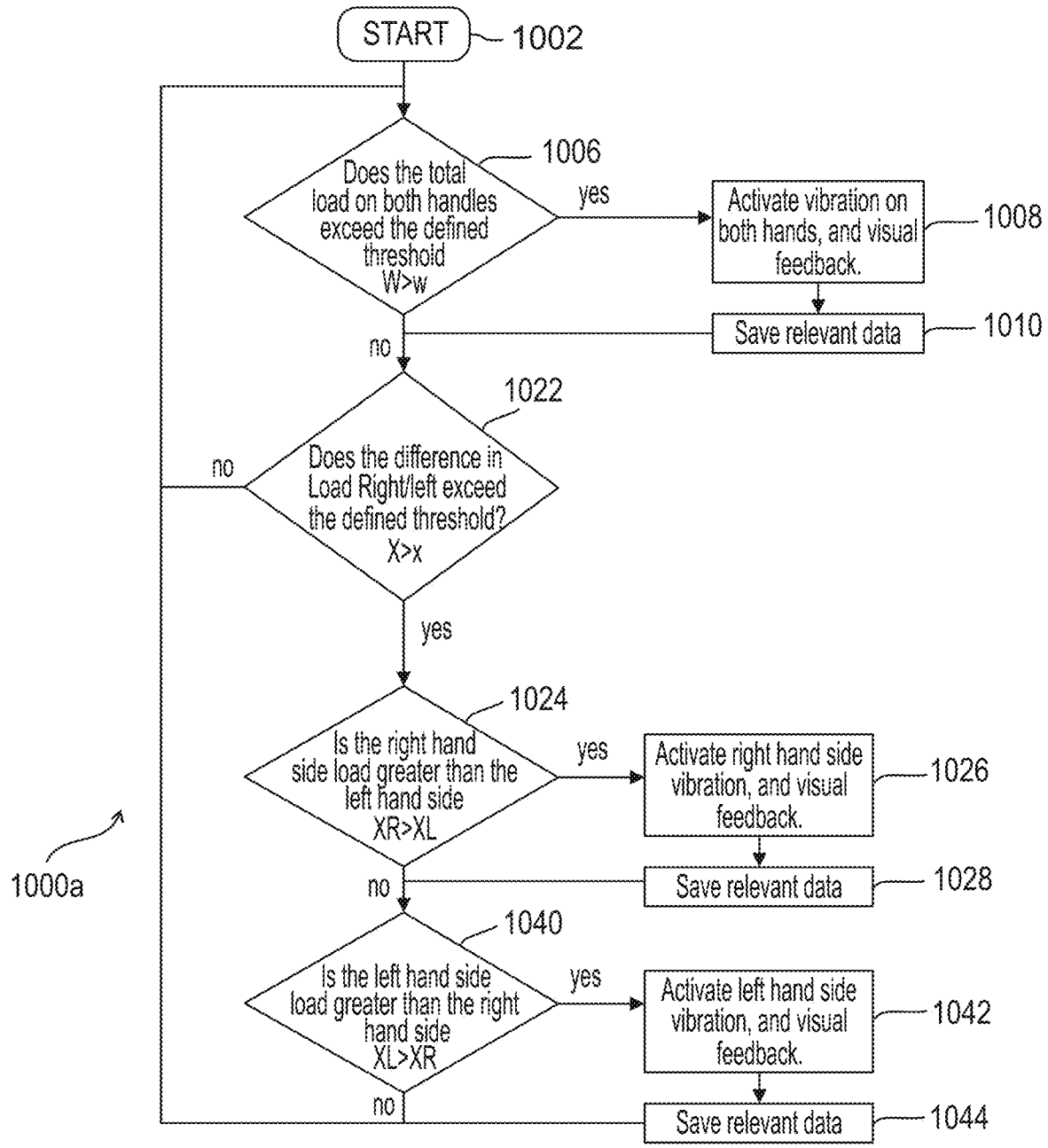

FIG. 10B is a flow chart 1000a showing an alternative embodiment of the different acts in the automatic generation of feedback in the regular use of the walker, according to some embodiments. As most of the steps are identical to those shown in FIG. 10A, they may not be described again herein. According to some embodiments, after entering "start" mode, the walker-assist device automatically begins checking whether pre-determined thresholds have been exceeded. For example, if the walker-assist device does have a total load threshold setting (step 1004 in FIG. 10A), then the device checks whether the actual total load (W) measured by the sensors on the walker-assist device exceeds that threshold (w) 1006.

Then the device checks whether the actual total load deviation (X) measured by the sensors on the walker-assist device exceed the set threshold (x) 1022.

According to some embodiments, these acts are continuously and automatically repeated in order to check for any incident in which the thresholds are exceeded, as discussed above with regard to FIG. 10A.

Manual Feedback Activation

Figure 11:
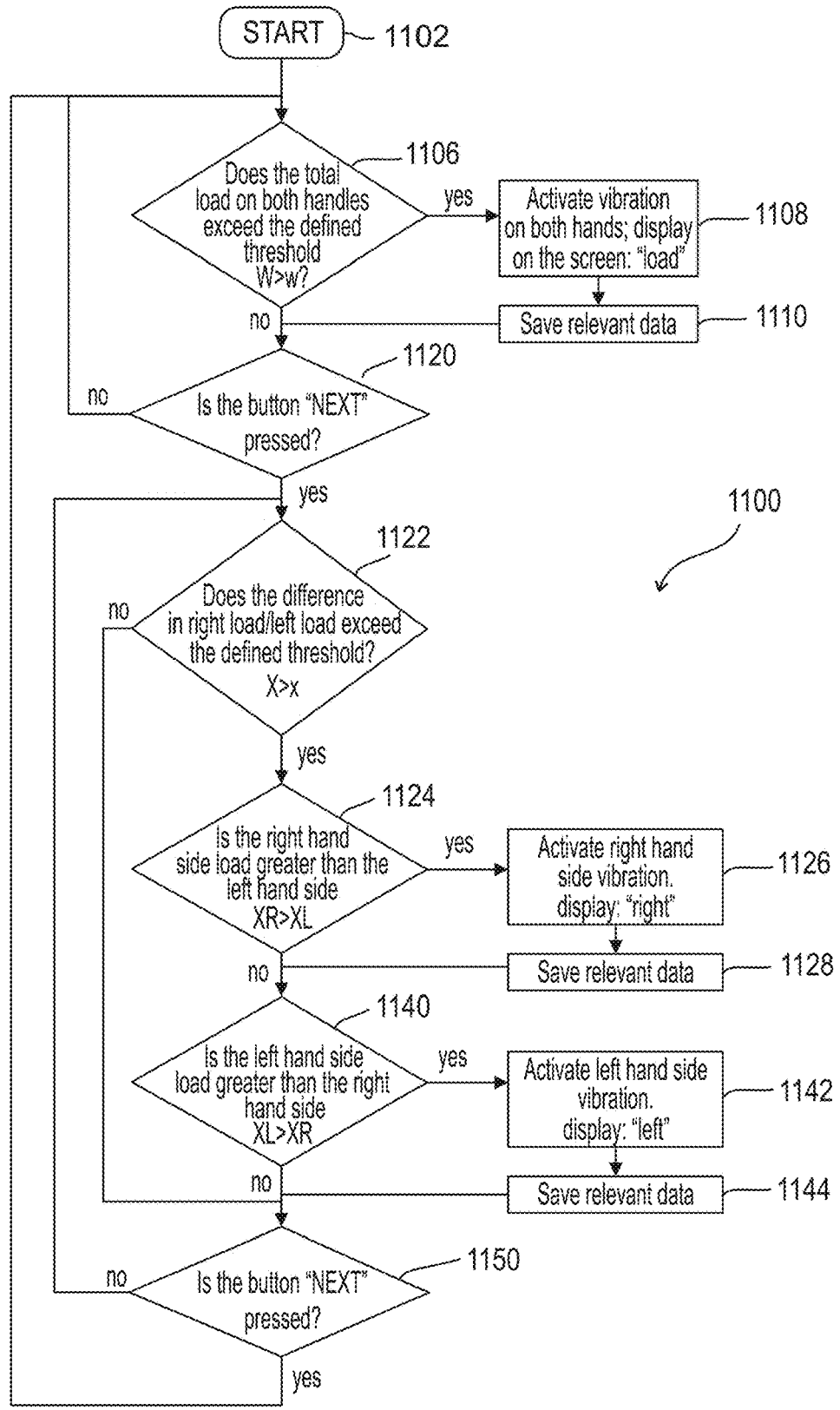
FIG. 11 is a flow chart showing the different acts in the manual determination of whether thresholds have been exceeded in the use of a walker-assist device, according to some embodiments of the invention.

According to some embodiments, feedback is generated manually in the regular use of the walker. For example, as shown in flow chart 1100 in FIG. 11, a patient may be prompted to manually move from one threshold check to another in order to manually generate feedback, according to some embodiments.

At 1102, the walker-assist device displays a prompt to "start" determining whether a threshold has been exceeded. If "Start" is selected, the walker-assist device determines whether the actual total load (W) measured by the sensors on the walker-assist device exceeds the pre-determined total load threshold (w) 1106.

According to some embodiments, if W exceeds w, an immediate feedback signal will be sent 1108. For example, vibrating elements may be activated inside both hand grips and/or the words "excessive load" may be displayed on the display screen. Optionally, relevant data regarding the incident in which the threshold was exceeded may be saved, for example the date, time and measure of the relevant parameters, such as load on the left side and load on the right side 1110.

According to some embodiments, if the total load threshold was not exceeded 1106, or if data regarding the exceeding of a total load threshold was saved 1110, the walker-assist device then provides a "Next" prompt 1120. If "Next" is selected, the walker-assist device determines whether the actual total load deviation (X) for the difference between the left and right loads, as measured by the sensors on the walker-assist device, exceeds the set deviation threshold (x) 1122.

According to some embodiments, if X exceeds x, the walker-assist device then determines whether the load on the right side load is greater than the load on the left side 1124. If the load on the right side load is greater than the load on the left side, an immediate feedback signal will be sent indicating that the right side load is too large 1126. For example, vibrating elements may be activated inside the right hand grip and/or the words "excessive load on RIGHT side" may be displayed on the display screen. Optionally, relevant data regarding the incident in which the threshold was exceeded may be saved, for example the date, time and measure of the relevant parameters, such as load on the left side and load on the right side 1128.

According to some embodiments, if the load on the right side load is not greater than the load on the left side, the walker-assist device checks whether the load on the left side is greater than the load on the right side 1140. If the load on the left side is greater than the load on the right side, an immediate feedback signal will be sent indicating that the left side load is too large 1142. For example, vibrating elements may be activated inside the left hand grip and/or the words "excessive load on LEFT side" may be displayed on the display screen. Optionally, relevant data regarding the incident in which the threshold was exceeded may be saved, for example the date, time and measure of the relevant parameters, such as load on the left side and load on the right side 1144.

According to some embodiments, prompts are continuously and automatically provide in order to continue allowing the operator of the walking device to determine whether the thresholds are exceeded. For example, if the load on the left side is not greater than the load on the right side, or if data regarding the exceeding of a total load threshold was saved 1128, the walker-assist device then provides a "Next" prompt 1150, which begins a new process of manually determining whether thresholds have been exceeds. Optionally, other thresholds, for example thresholds for the speed, acceleration, gait, blood oxygen saturation and/or force, variability and/or rapidity of the pulse of the patient, are checked in a similar fashion.

Assessment—TUG Test

Figure 12A:
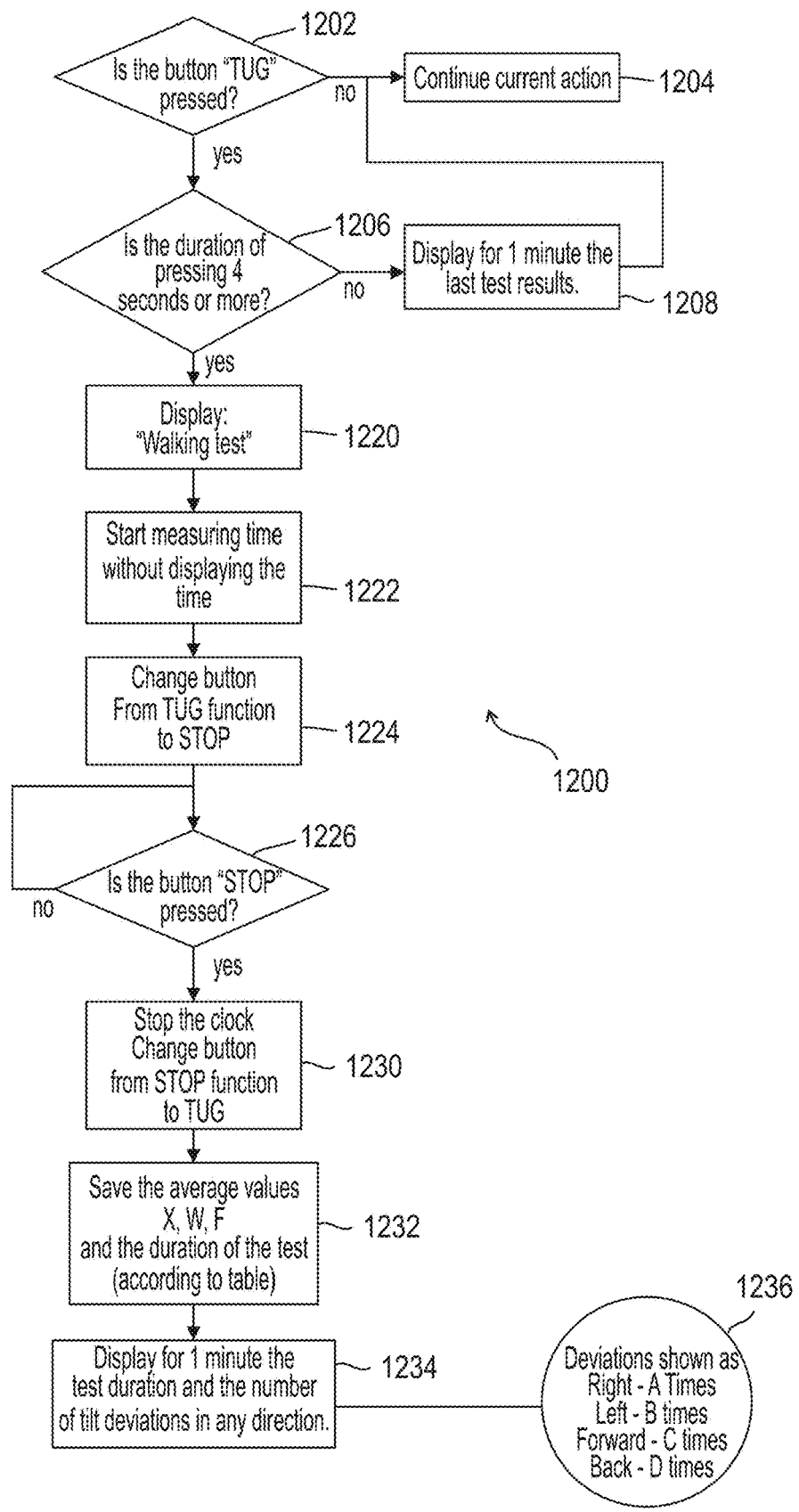
FIGS. 12a and 12b are flow charts showing the different acts in the assessment of a patient during a Timed Up and Go (TUG) test, performed with the aid of a walker and walker-assist device, according to some embodiments of the invention.

FIG. 12A is a flow chart 1200 showing the different acts in the assessment of a patient during a Timed Up and Go (TUG) test, performed with the aid of a walker and walker-assist device, according to some embodiments. As used herein, a "TUG test" refers to the measurement of the time it takes a person to rise from a chair, walk three meters, turn around, walk back to the chair, and sit down.

According to some embodiments, a button is dedicated for endurance testing and for displaying endurance testing results. The dedicated button may be an actual button, for example a button marked "TUG" and located to the side of the display screen on the control panel, or a "TUG" prompt located on the display screen which may be touch activated or may be activated by scrolling through different screen option in order to arrive at and select "TUG." Alternatively, "TUG" may be selected by entering a general menu which then includes a "TUG" prompt.

According to some embodiments, the walker-assist device continuously determines whether "TUG" is selected 1202. If "TUG" is not selected, the walker-assist device continues to perform the action it is already performing or, if no action is already being performed, the walker-assist device continues to operate in stand by status 1204.

If the walker-assist device determines that "TUG" has been selected, the walker-assist device then determines whether the "TUG" button has been pressed for 4 seconds or more 1206. Optionally or alternatively, the walker-assist device determines whether the "TUG" prompt is touched on a touch screen for 4 seconds or more. If the "TUG" button has not been pressed or touched for 4 seconds or more, the most recent TUG test results are displayed for 1 minute 1208. If the "TUG" button has been pressed or touched for 4 seconds or more, "Walking Test" is displayed on the display screen 1220.

Alternatively, when selecting "TUG," the display screen presents a choice of prompts to "Display Latest TUG Test Results" or "Start TUG Test." If "Display Latest TUG Test Results" is selected, the most recent TUG test results are displayed for 1 minute 1208. If "Start TUG Test" is selected, "Walking Test" is displayed on the display screen 1220.

After "Walking Test" is displayed on the display screen 1220, the walker-assist device begins measuring time and/or other parameters, without displaying the time 1222. Alternatively, the elapsed time is displayed.

After the walker-assist device begins measuring time 1222, the "TUG" button acts as a "Stop" button 1224 and pressing, touching or selecting the button stops the measuring of time and/or other parameters 1226. At that point, the button reverts to acting as a "TUG" button 1230 and measurements and/or averages of measurements of time duration and/or other parameters that were measured are saved 1232.

The display screen then displays the duration of time of the test and a summation of other measurements that were made, for example, the number of deviations of load exceeding a deviation threshold 1234. Optionally, the number of deviations is shown separately for each direction, for example, the number of times that deviation exceeded a threshold and caused a tilt to the right, to the left, forward and/or backwards 1236.

Figure 12B:
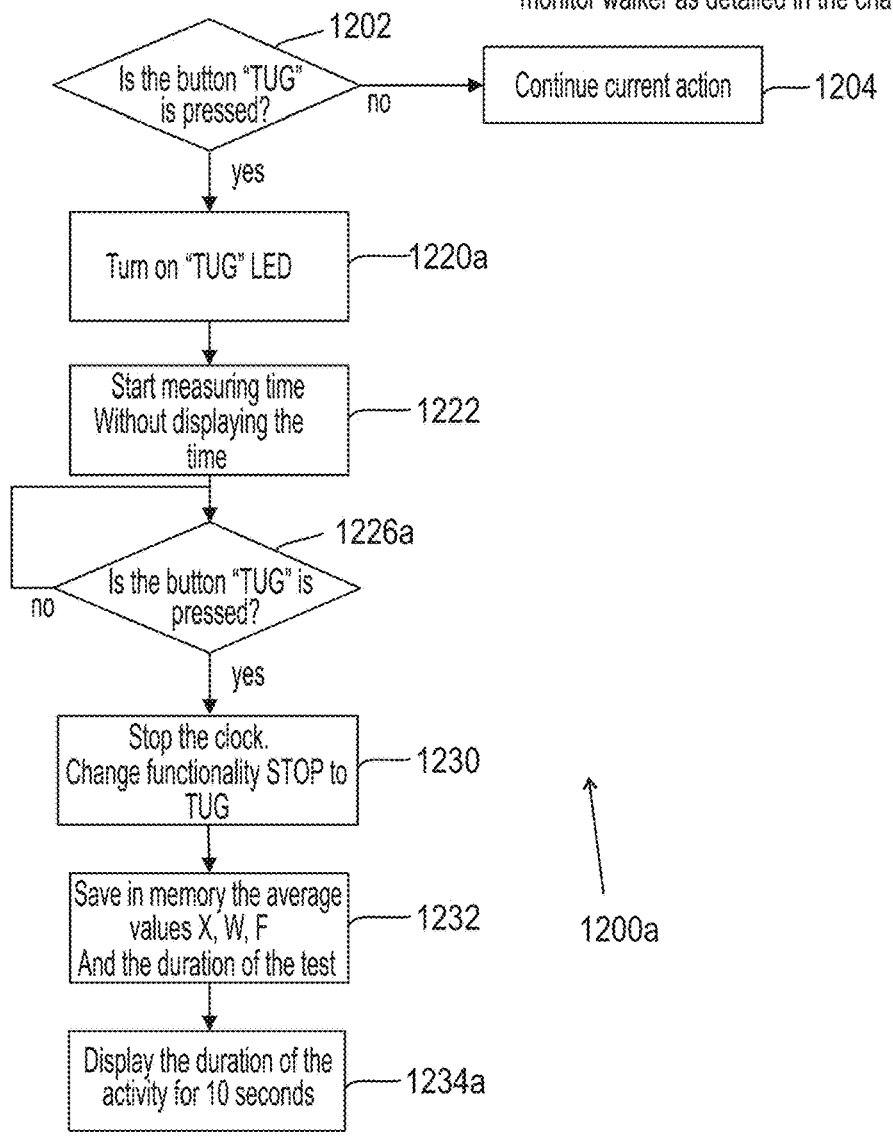

FIG. 12B is a flow chart 1200a showing the different acts in the assessment of a patient during a Timed Up and Go (TUG) test, performed with the aid of a walker and walker-assist device, according to an alternative embodiment. As most of the steps are identical to those shown in FIG. 12A, they may not be described again herein.

According to some embodiments, the walker-assist device continuously determines whether "TUG" is selected, at 1202. If "TUG" is not selected, the walker-assist device continues to perform the action it is already performing or, if no action is already being performed, the walker-assist device continues to operate in stand by status, at 1204.

If the walker-assist device determines that "TUG" has been selected, a "TUG" LED is lit on the display screen, at 1220a. The walker-assist device then begins measuring time and/or other parameters, without displaying the time, at 1222. Alternatively, the elapsed time is displayed.

After the walker-assist device begins measuring time, at 1222, pressing the "TUG" button, at 1226*a* stops the measuring of time and/or other parameters, at 1230. At that point, the button reverts to acting as a "TUG" button and measurements and/or averages of measurements of time duration and/or other parameters that were measured are saved 1232.

The display screen then displays the duration of time of the test and a summation of other measurements that were made, for example, the number of deviations of load exceeding a deviation threshold, at 1234*a*, for 10 seconds.

Displaying TUG Test Results

According to some embodiments, the TUG test results are displayed in a table on the display screen of the control panel. For example, FIG. 16 is a table showing measurements of different parameters and time duration for each stage of the TUG test, according to some embodiments. In an exemplary embodiment, different parameter values (for example, X, W, F1, F2, F3 and/or F4, described below in the section entitled "Parameters in TUG Test") and/or time durations are provided for each of the five acts in the TUG test (rising from a chair, walking three meters, turning around, walking back to the chair, and sitting down).

According to some embodiments, totals for one or more of the measured parameters, including time duration, throughout all the tasks, are provided, for example, on the bottom line. Optionally or alternatively, each of the totals for the five most recent testing results may be displayed in a table together with the corresponding date and time.

According to some embodiments, the saved information will be deleted from the walker after this information is transferred to the host computer or another computer and/or when switching to a different user.

According to some embodiments, a potential advantage of providing a display of this feedback is that it assists a patient in learning a better walking pattern and/or stability in walking.

Parameters in TUG Test

According to some embodiments, the different parameter values measured and displayed include one or more tilt variations in different directions. For example, FIG. 17 is a table showing definitions of the parameters listed in the table in FIG. 16, as well as other parameters, their units of measure, and the corresponding symbol for the pre-determined threshold value of each parameter, according to some embodiments.

According to some embodiments, W represents the actual measured total load, in Kg, and w represents the pre-determined threshold value of that parameter. Optionally, XR represents the actual measured load on the right side in Kg, and no pre-determined threshold value exists for that parameter. Optionally, XL represents the actual measured load on the left side in Kg, and no pre-determined threshold value exists for that parameter. Optionally, X represents the actual measured difference in load between the right side (XR) and the left side (XL), in Kg, and x represents the pre-determined threshold value of that parameter.

According to some embodiments, F1 represents the actual tilt to the right, in degrees, and f1 represents the pre-determined threshold value of that parameter. For example, f1 is the tilting angle at which an immediate danger of falling exists. According to some embodiments, F2 represents the actual tilt to the left, in degrees, and f2 represents the pre-determined threshold value of that parameter. According to some embodiments, F3 represents the actual tilt forward, in degrees, and f3 represents the pre-determined threshold value of that parameter. According to some embodiments, F4 represents the actual tilt backward, in degrees, and f4 represents the pre-determined threshold value of that parameter.

Assessment—Stamina Test

Figure 13A:
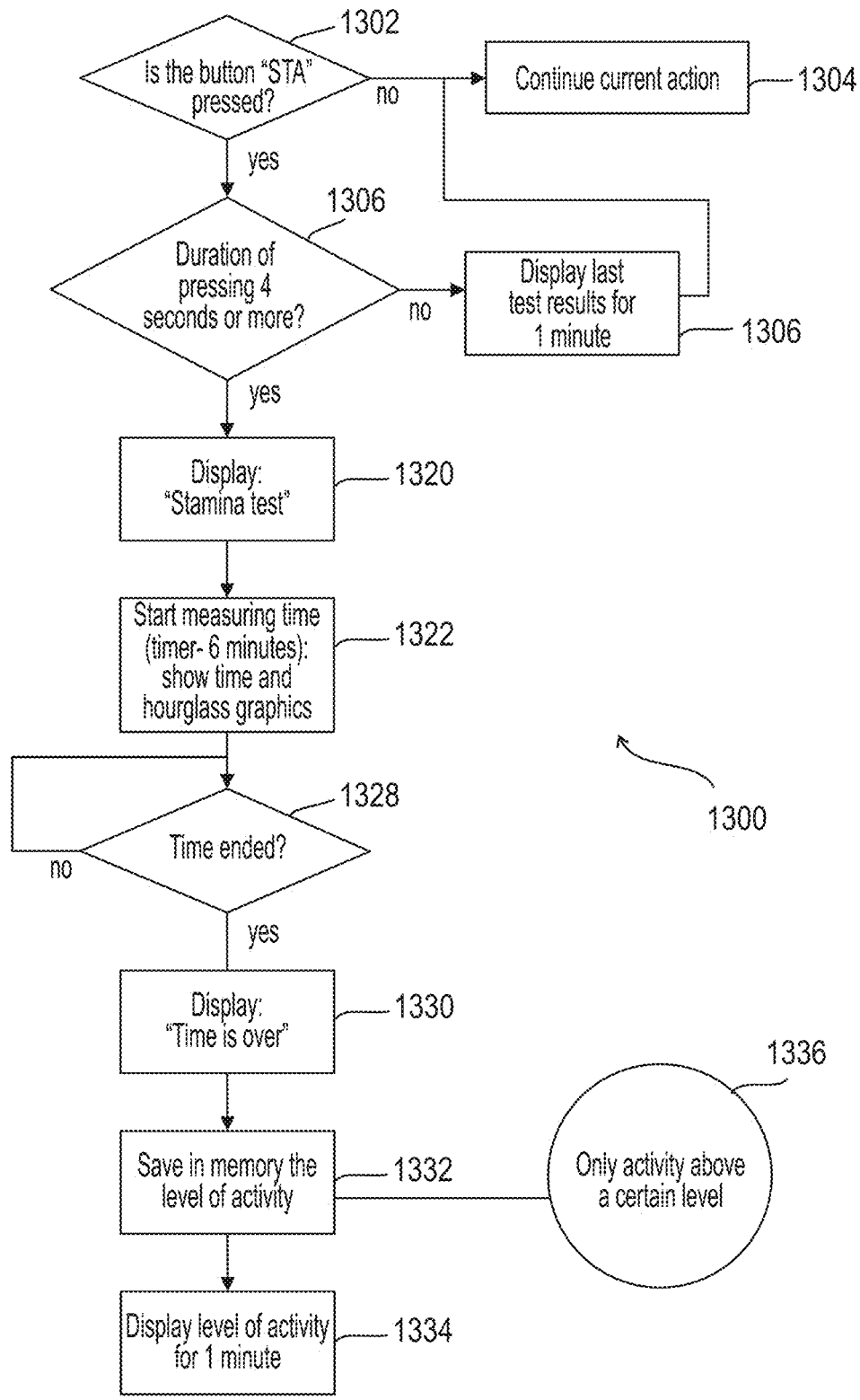
FIGS. 13a and 13b are flow charts showing the different acts in the assessment of a patient's stamina, performed with the aid of a walker and walker-assist device, according to some embodiments of the invention.

FIG. 13A is a flow chart 1300 showing the different acts in the assessment of a patient's stamina, performed with the aid of a walker-assist device, according to some embodiments.

According to some embodiments, a button is dedicated for stamina testing and for displaying stamina testing results. The dedicated button may be an actual button, for example a button marked "STA" (short for stamina) and located to the side of the display screen on the control panel, or an "STA" prompt located on the display screen which may be touch activated or may be activated by scrolling through different screen option in order to arrive at and select "STA." Alternatively, "STA" may be selected by entering a general menu which then includes a "STA" prompt.

According to some embodiments, the walker-assist device continuously determines whether "STA" is selected 1302. If "STA" is not selected, the walker-assist device continues to perform the action it is already performing or, if no action is already being performed, the walker-assist device continues to operate in stand by status 1304.

If the walker-assist device determines that "STA" has been selected, the walker-assist device then determines whether the "STA" button has been pressed for 4 seconds or more 1306. Optionally or alternatively, the walker-assist device determines whether the "STA" prompt is touched on a touch screen for 4 seconds or more. If the "STA" button has not been pressed or touched for 4 seconds or more, the most recent stamina test results are displayed for 1 minute 1308. If the "STA" button has been pressed or touched for 4 seconds or more, "Stamina Test" is displayed on the display screen 1320.

Alternatively, when selecting "STA," the display screen presents a choice of prompts to "Display Latest Stamina Test Results" or "Start Stamina Test." If "Display Latest Stamina Test Results" is selected, the most recent STA test results are displayed for 1 minute 1308. If "Start Stamina Test" is selected, "Stamina Test" is displayed on the display screen 1320.

After "Stamina Test" is displayed on the display screen 1320, the walker-assist device begins measuring a six minute time duration and/or other parameters, while displaying the time remaining in the six minute time duration 1322. Optionally, the time remaining is shown in digital form and/or in hourglass graphics. Alternatively, the elapsed time is not displayed.

After the walker-assist device begins measuring time 1322, the walker-assist device determines whether the six minute time duration has expired 1328. If it is determined that the six minute time duration has not expired, this act is repeated, continuously, until it is determined that the six minute time duration has expired.

After it is determined that the six minute time duration has expired, the display screen displays "Time is Over" 1330. After "Time is Over" is displayed, the level of activity over time, or the average level of activity, that was maintained during the six minute stamina test, is saved in the memory of the walker-assist device and/or a remote computer 1332. The level of activity over time, or the average level of activity, is then displayed on the display screen 1334.

According to some embodiments, this saved information will be deleted from the walker after this information is transferred to the host computer or another computer and/or when switching to a different user.

According to some embodiments, a potential advantage of providing a display of this feedback is that it assists a patient in learning a better walking pattern and/or stability in walking.

Figure 13B:
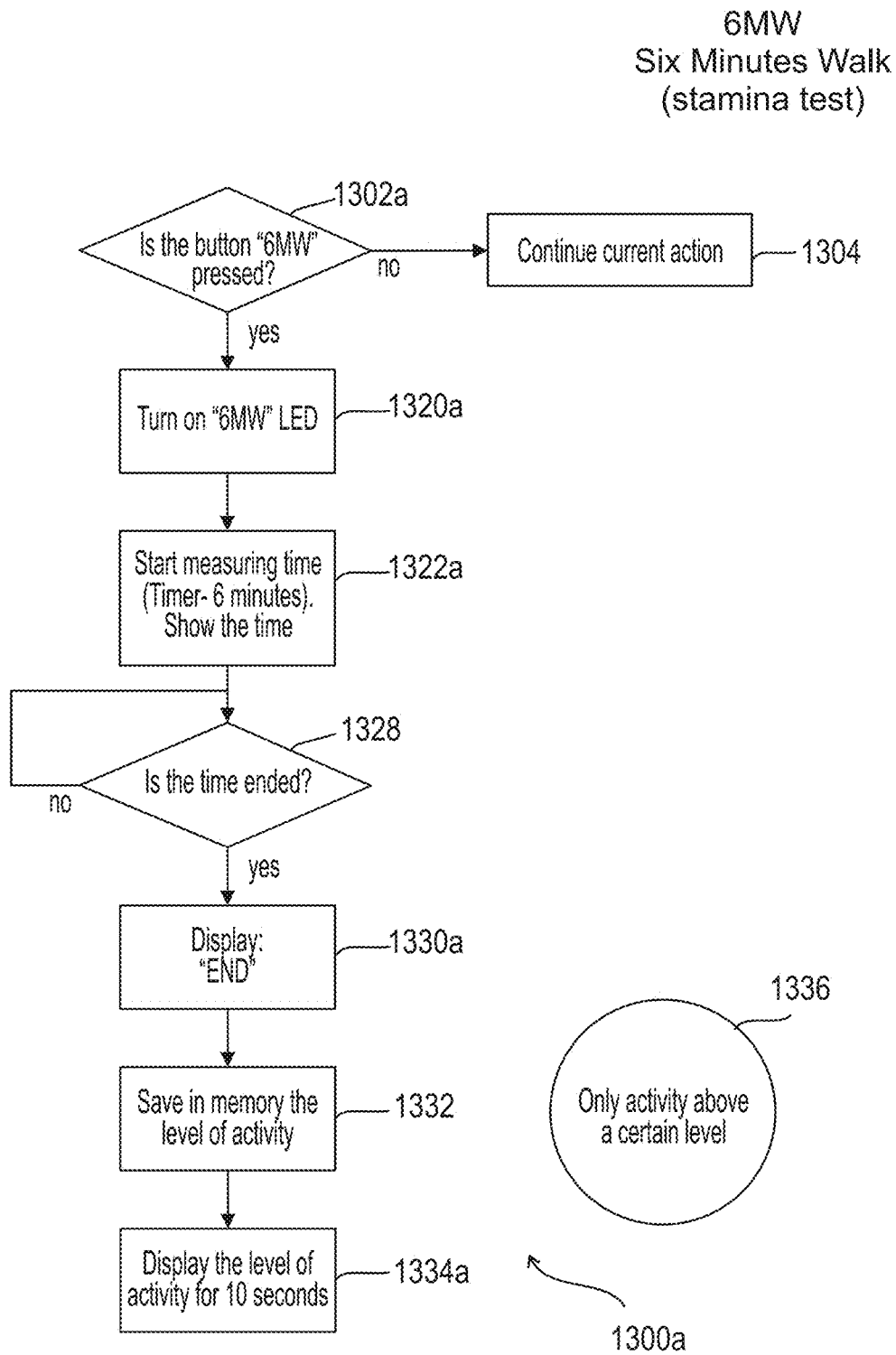

FIG. 13B is a flow chart 1300a showing the different acts in the assessment of a patient's stamina, performed with the aid of a walker-assist device, according to an alternative embodiment. As most of the steps are identical to those shown in FIG. 13A, they may not be described again herein.

According to some embodiments, a button is dedicated for stamina testing and for displaying stamina testing results. The dedicated button may be an actual button, for example a button marked "6MW" (short for "six minute walk") and located to the side of the display screen on the control panel, or a "6MW" prompt located on the display screen which may be touch activated or may be activated by scrolling through different screen options in order to arrive at and select "6MW." Alternatively, "6MW" may be selected by entering a general menu which then includes a "6MW" prompt.

According to some embodiments, the walker-assist device continuously determines whether "6MW" is selected, at 1302a. If "6MW" is not selected, the walker-assist device continues to perform the action it is already performing or, if no action is already being performed, the walker-assist device continues to operate in stand by status 1304.

If the walker-assist device determines that "6MW" has been selected, a "6MW) LED is lit up on the display screen, at 1320a. The walker-assist device then begins measuring a six minute time duration and/or other parameters, while displaying the time remaining in the six minute time duration 1322a.

After the walker-assist device begins measuring time 1322, the walker-assist device determines whether the six minute time duration has expired, at 1328. If it is determined that the six minute time duration has not expired, this act is repeated, continuously, until it is determined that the six minute time duration has expired.

After it is determined that the six minute time duration has expired, the display screen displays "END" at 1330a. After "END" is displayed, the level of activity over time, or the average level of activity, that was maintained during the six minute stamina test, is saved in the memory of the walker-assist device and/or a remote computer, at 1332. The level of activity over time, or the average level of activity, is then displayed on the display screen for 10 seconds, at 1334a.

Control Unit

FIG. 18A is a schematic illustration of a control unit 1800 including an upper portion 1822 having buttons, speaker and display screen 1801 of a walker-assist device, for example control unit 340 of FIG. 3, according to some embodiments.

According to some embodiments, control unit 1800 includes an on/off switch 1830 and three buttons, a top button 1802, a middle button 1804 and a bottom button 1806, are located on the left of the display screen. Optionally, top button 1802 acts as a "Next" button, for example, in scrolling through program modes or options on the display screen in order to view a display of feedback on different parameters. Optionally, middle button 1804 initiates a stamina test and/or displays stamina test results. Optionally, bottom button 1806 initiates a TUG test and/or displays TUG test results.

Optionally, another button may be provided with which to select the parameters that provide feedback by means of vibrations in the hand grips. These parameters may include weight applied to the hand grips and asymmetry in application of weight to the hand grips, as discussed herein.

According to some embodiments, an SOS button 1808 is located on the display screen. Optionally, button 1808 acts a "Help" or "Panic" button, sending an alert to a third party monitor and/or an audio and/or visual alert from the walker-assist device when pressed, touched or selected. A potential benefit of providing an audio and/or visual alert from the walker-assist device itself is that people in the area of the walker-assist device may learn that the patient is in need of immediate assistance.

According to some embodiments, a speaker (not shown) is located on the display screen. Optionally, the speaker provides an audio alert when SOS button 1808 is activated and/or when certain parameter thresholds are exceeded.

Screen Shots

FIGS. 19-38 are or comprise screen shots of the display screen component of a walker-assist device, according to some embodiments, which may serve to illustrate some features which may be optionally provided in some embodiments of the invention.

Activity Monitoring

Figure 28:
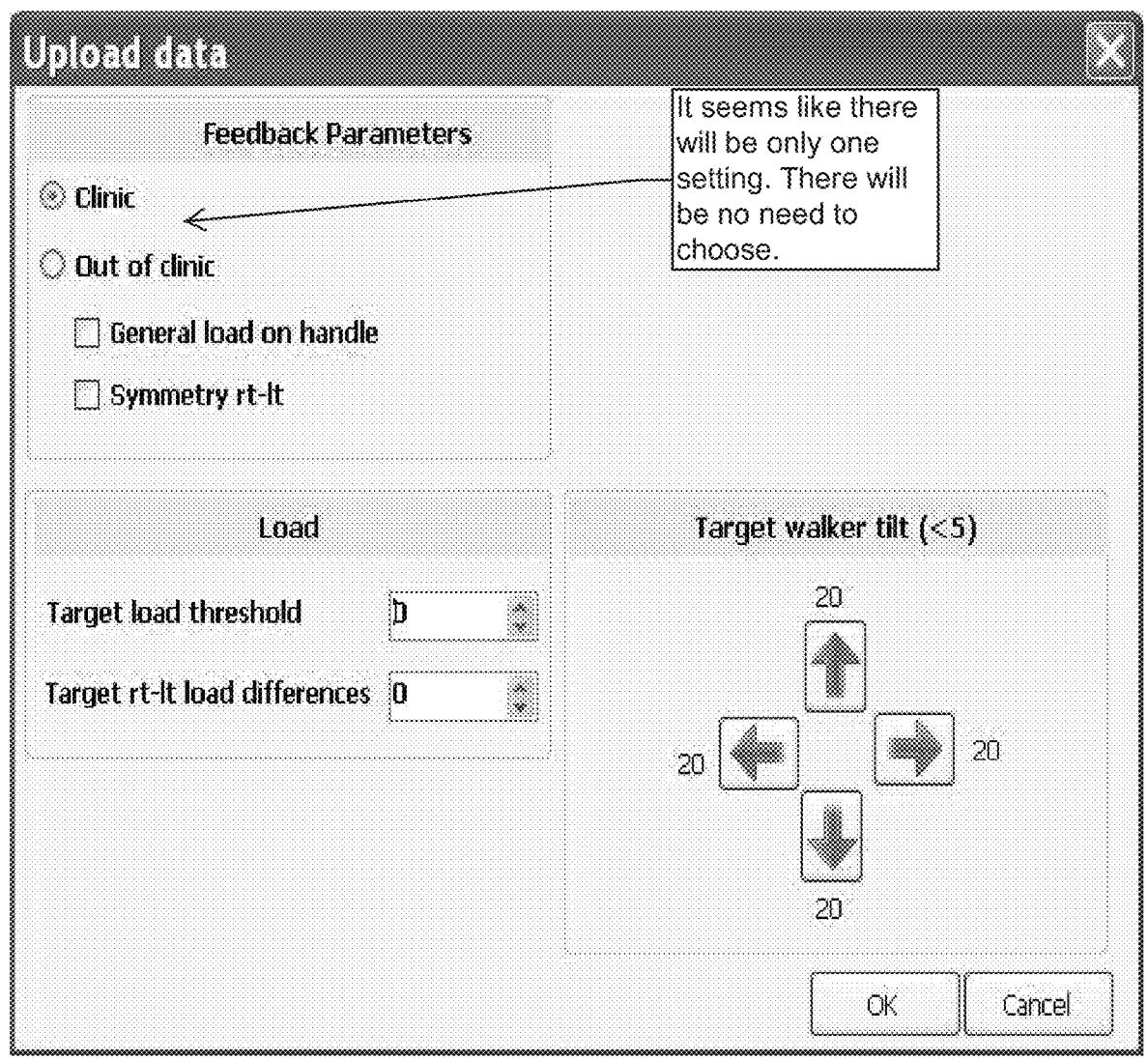
FIG. 28 is screen shot of a determination of load thresholds screen, according to some embodiments of the invention.

FIG. 28, discussed further herein, shows a sample screen shot, on a display screen, indicating load and tilt in four directions along "feedback axes" and prompt choices in the use of a walker-assist device, according to some embodiments.

According to some embodiments, the prompt "Next" or "Mode" appears on the left side of the display screen, next to the top left button 1802. Optionally, the prompt "TUG" appears on the left side of the display screen, next to the bottom left button 1806. Optionally, the display next to the bottom left button 1806 changes to "Stop" once a TUG test begins and reverts back to "TUG" once a TUG test is stopped. Optionally, the prompt "STA" or "6MW" appears on the left side of the display screen, next to the middle left button 1804.

According to some embodiments, a battery status indicator 1812 is located on the right side of the display screen, indicating how much power remains in the battery. Optionally, the total load in kg is displayed in the top right corner of the display screen. Optionally, the current time is displayed in the bottom right corner of the display screen. Optionally or alternatively, the time display changes to a stop watch function, counting the number of minutes and/or seconds that have expired, once a TUG test begins. Optionally or alternatively, the time display reverts back to displaying the time of day once a TUG test is stopped.

According to some embodiments, a graphic display of the tilt and load, in each of four directions (right, left, forward and backward), is provided on axes emanating from the middle of the display screen. For example, the left horizontal axis may indicate the extent of tilt and load in the left direction. Optionally, the right horizontal axis may indicate the extent of tilt and load in the right direction. Optionally, the upper vertical axis may indicate the extent of tilt and load in the forward direction. Optionally, the lower vertical axis may indicate the extent of tilt and load in the backward direction.

Figure 18B:
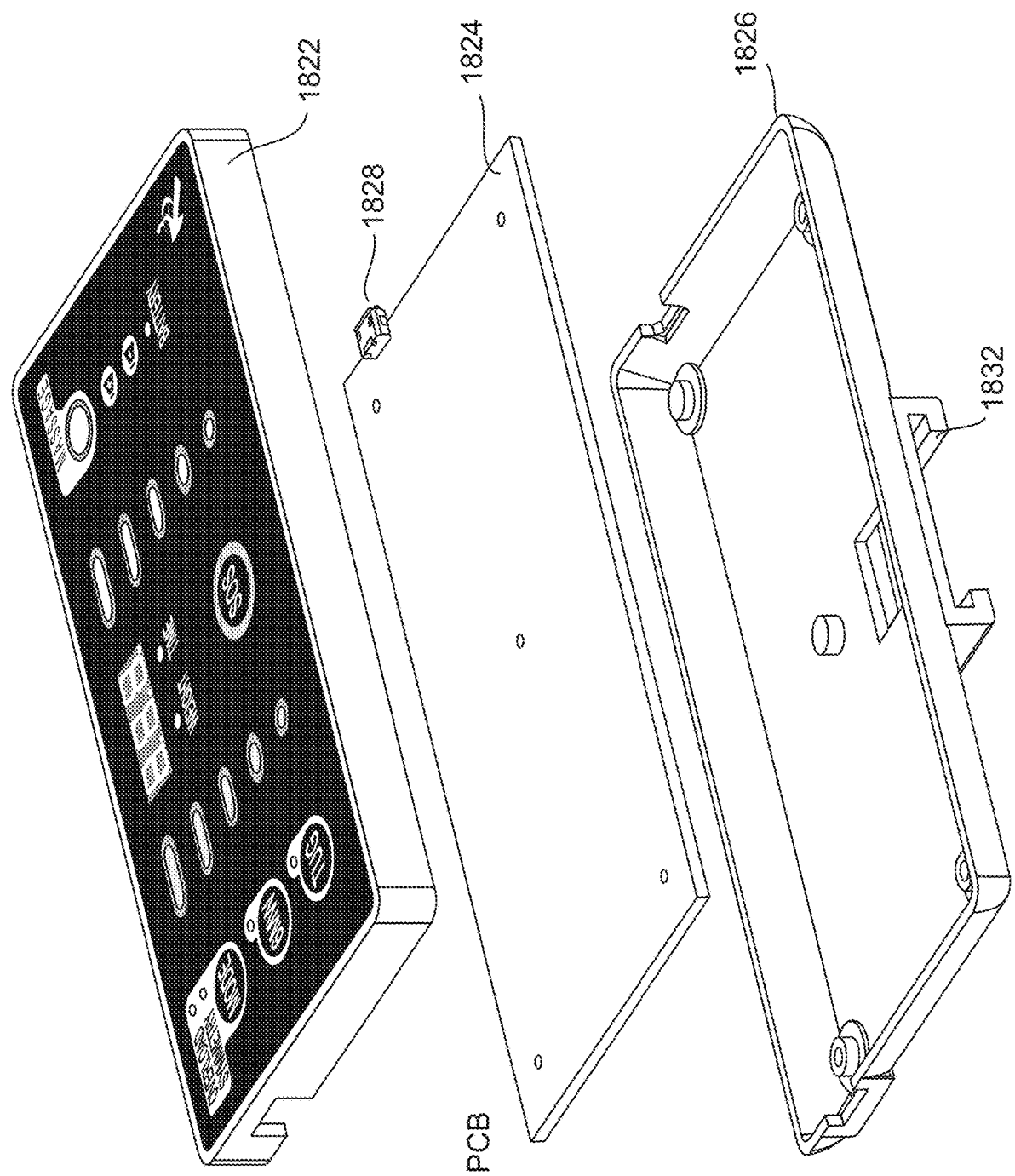
FIG. 18b is an exploded view of the control unit shown in FIG. 18A.

FIG. 18B is an exploded view of the control unit 1800, which in some embodiments may include upper portion 1822, a printed circuit board (PCB) 1824, and a lower portion 1826 including a bracket for attaching the control unit 1800 to a feedback walker, as known in the art. PCB 1824 may include a port 1828, for example, for charging the control unit or for the transfer of data to and/or from the control unit.

Welcome Screen

FIG. 19 is a screen shot of the welcome screen which optionally appears when the walker-assist device 300 of FIG. 3 is manually turned on or automatically turns on due to a detected motion, according to some embodiments. The welcome screen displays the words "Welcome" and a short title describing the rehabilitation program, for example, "Welcome to Biofeedback." Optionally, the welcome screen contains a prompt, for example, "get started," which, when activated, allows a user of the walker-assist device to advance to a log in screen.

Therapist Log in

Figure 20:
FIG. 20 is a screen shot of a therapist log in screen, according to some embodiments of the invention.

FIG. 20 is a screen shot of a log in screen for a therapist, according to some embodiments. According to some embodiments, the log in screen requests a username and password from the therapist treating the patient. Optionally, the username and password may be entered by pressing buttons next to the screen, by touching characters appearing on a touch screen display and/or by transmitting a code via a cell phone, by reading a barcode by a barcode scanner incorporated into the walker-assist device, by reading a radio-frequency identification (RFID) by an RFID reader incorporated into the walker-assist device, or by transmitting a signal by Bluetooth, for example by a Bluetooth keyboard, or any other code recognition system. Optionally or alternatively, the patient herself, or someone assisting her, may input the username and password.

According to some embodiments, the log in screen contains a prompt to "Enter" the provided username and password which have been typed. If the username and password are correct, pressing Enter will lead to a new screen in which a type of patient is selected. Optionally, if the username and password have not been entered correctly, the log in screen refreshes and reappears with the username and password blank.

Patient Identification

Figure 21:
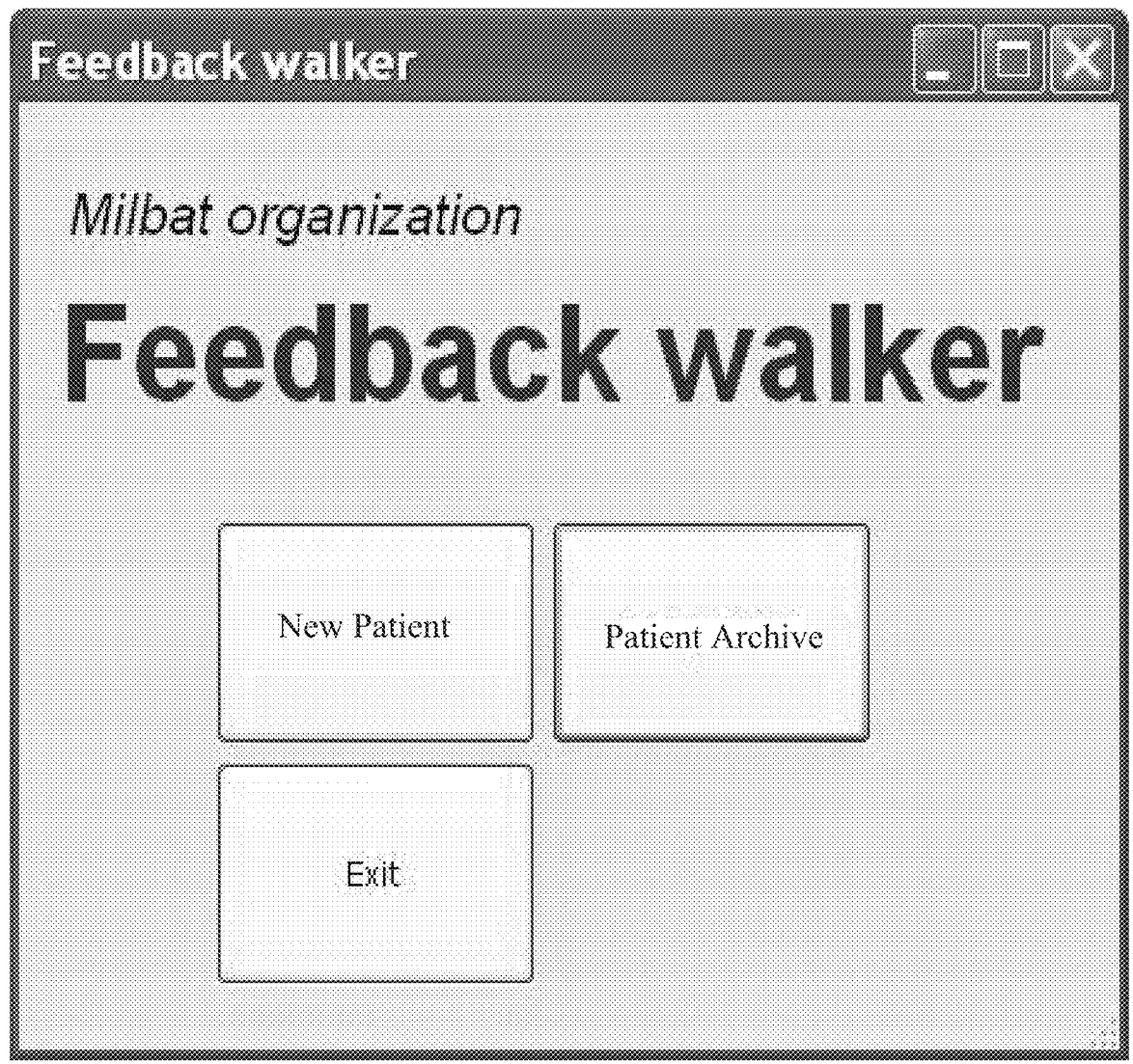
FIG. 21 is a screen shot of a patient type selection screen, according to some embodiments of the invention.
Figure 22:
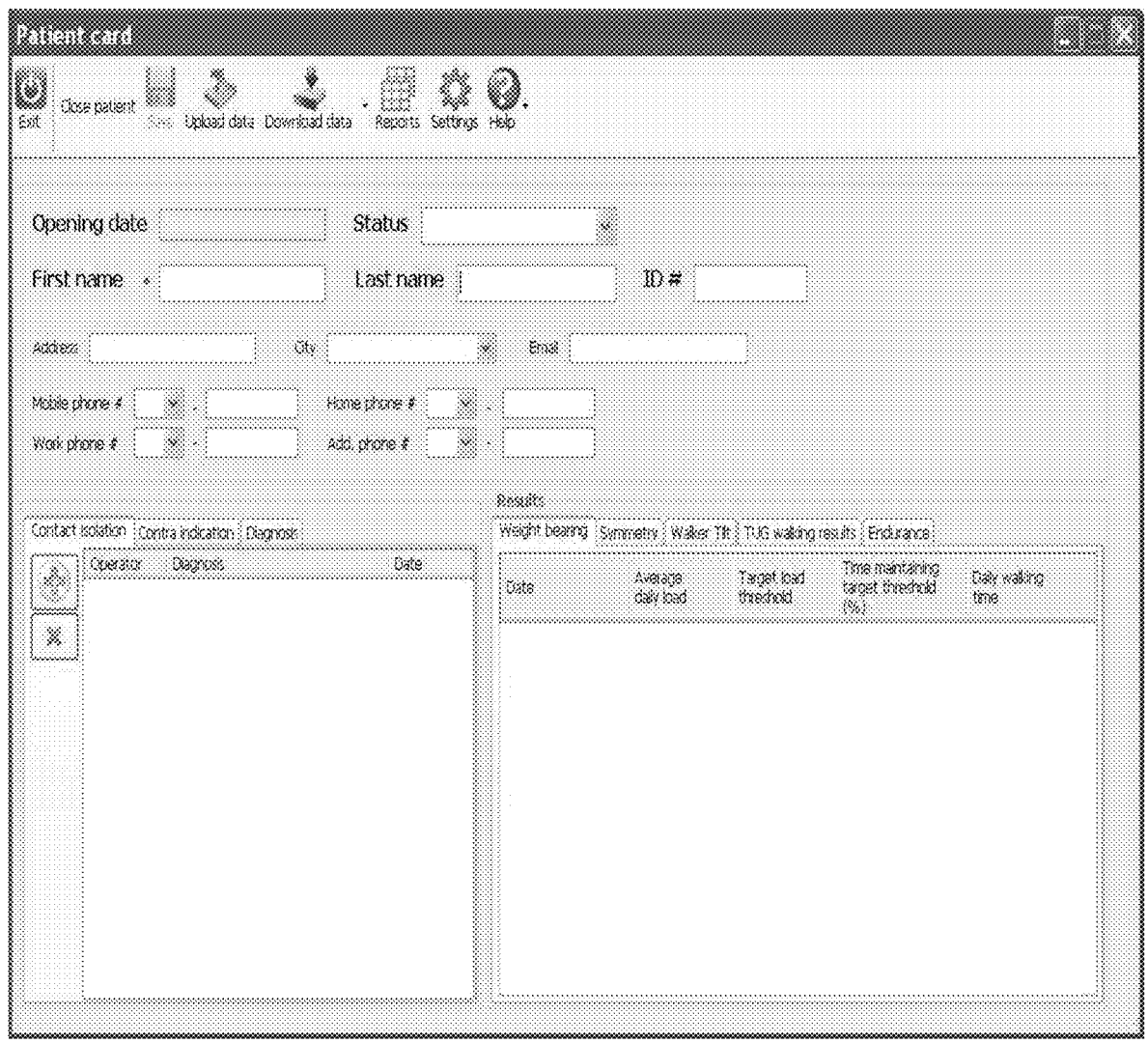
FIG. 22 is a screen shot of a registered patient identification screen, according to some embodiments of the invention.

FIG. 21 is screen shot of a patient type selection screen, according to some embodiments. The therapist, patient and/or patient's assistant selects either "New Patient" or "Existing Patient." If "New Patient" is selected, the display screen will display a registered patient identification screen, as seen in FIG. 22, prompting the therapist to provide the name and identification number of the patient, according to some embodiments. If the name and identification number of the patient are entered correctly, selecting an "Enter" button will cause a main menu to appear on the display screen. If the name and identification number of the patient is not entered correctly, the patient identification screen refreshes and reappears with the name and identification number blank.

Figure 23:
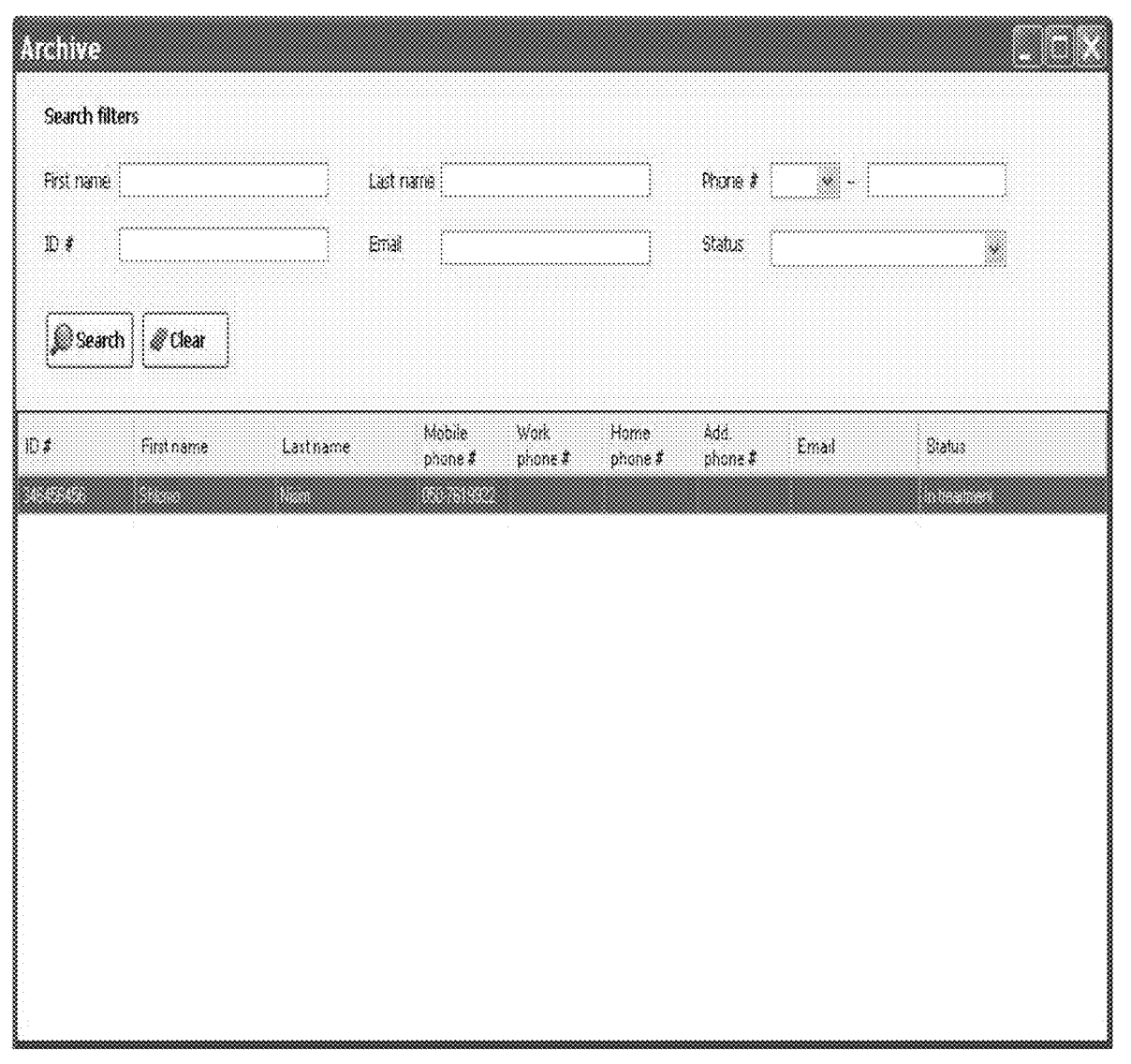

If "Existing Patient" is selected, the display screen will display a new patient identification screen, as seen in FIG. 23, prompting the therapist to provide, for example, the name, identification number and diagnosis of the patient, according to some embodiments. If the name and identification number of the patient is entered correctly and some entry is made for diagnosis, selecting an "Enter" button will cause a main menu to appear on the display screen. If the name and identification number of the patient is not entered correctly, or if no entry is made for diagnosis, the patient identification screen refreshes and reappears with the name and identification number blank.

Alternatively, if the entry for diagnosis does not match a pre-determined list of approved entries, the patient identification screen refreshes and reappears with the name and identification number blank. Optionally or alternatively, the diagnosis entry can or must be selected from a drop down menu in order to progress to the main menu.

Main Menu

Figure 24:
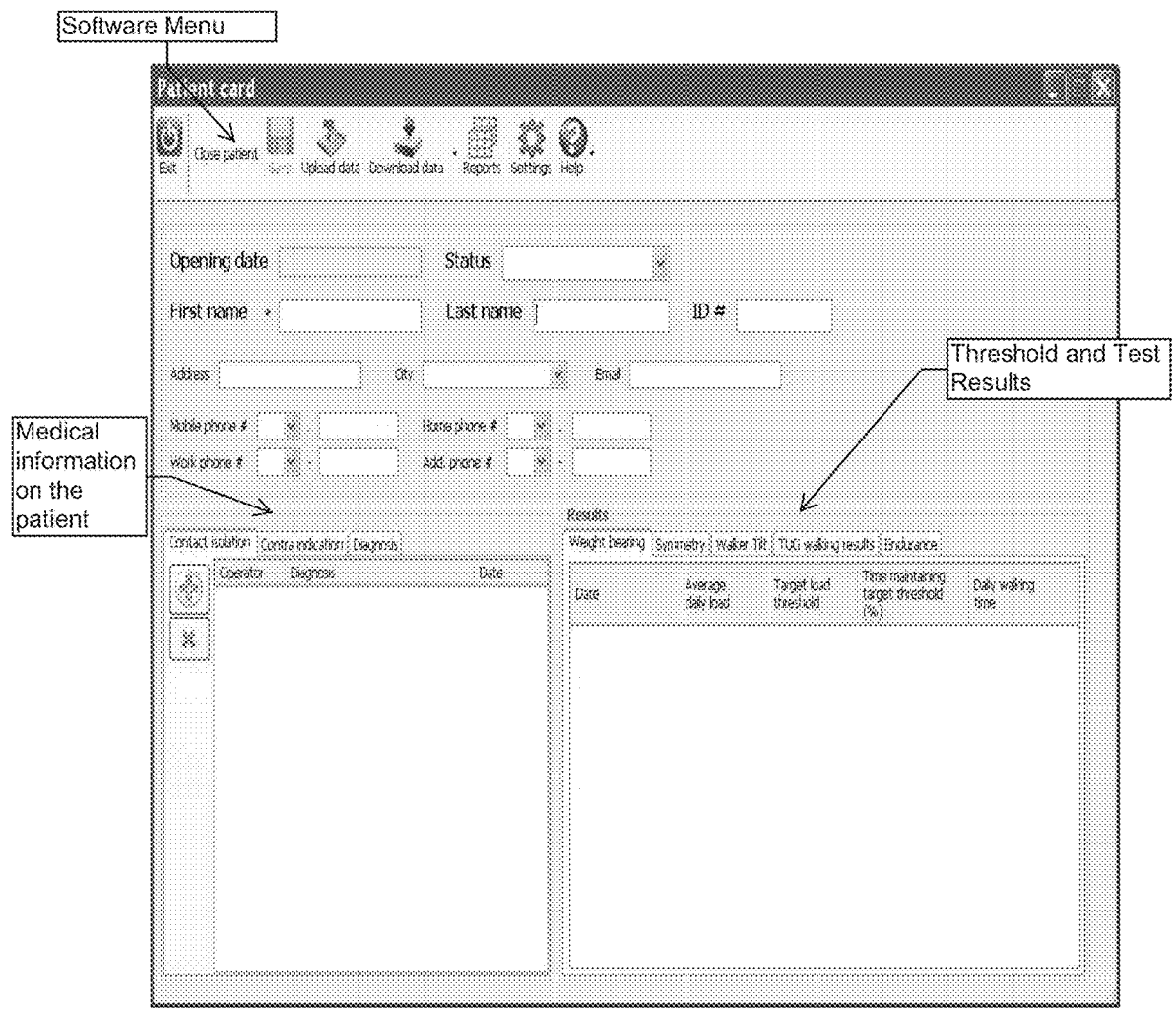
FIG. 24 is screen shot of a main menu of activities and selections, according to some embodiments of the invention.
Figure 25B:
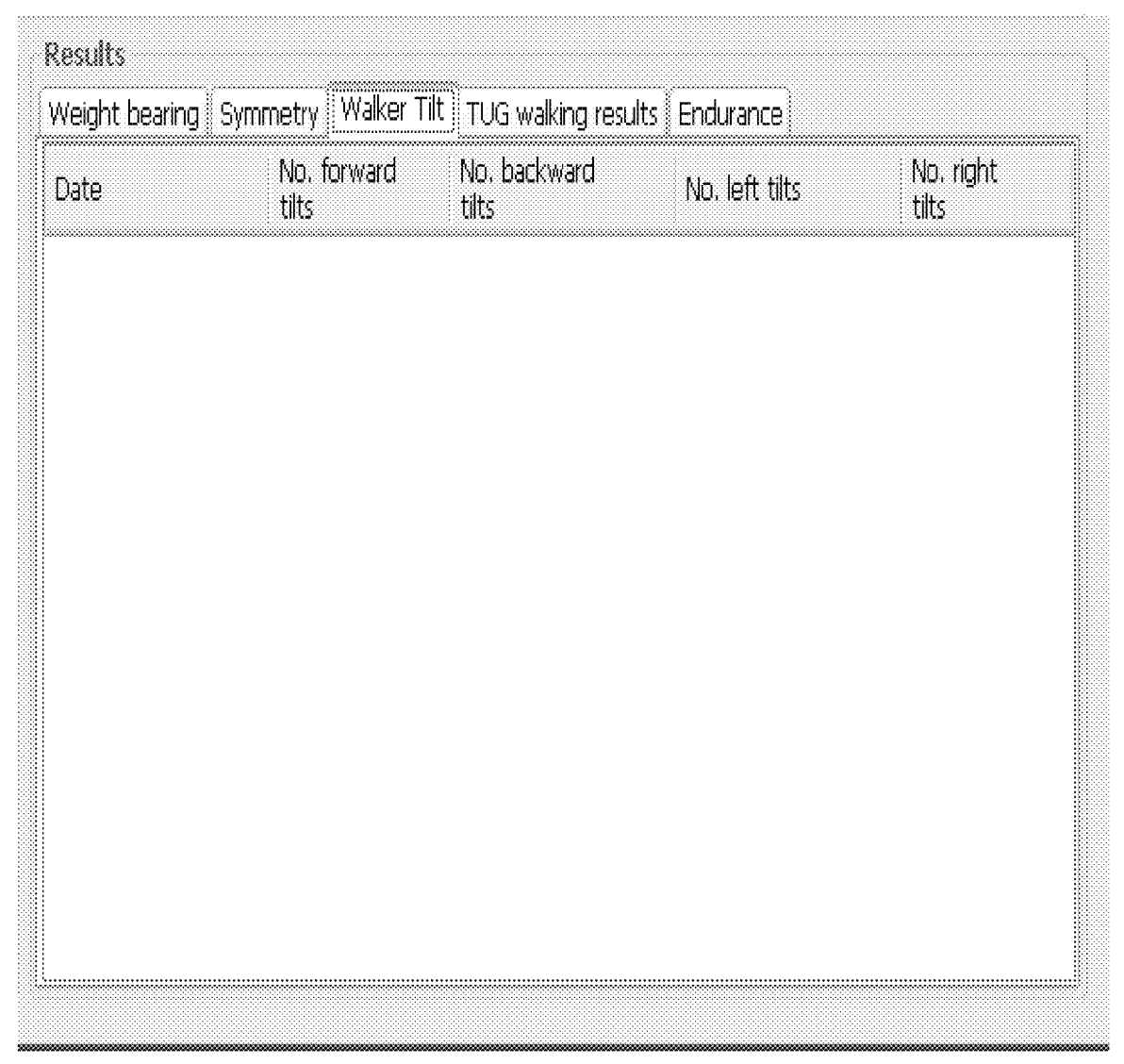
Figure 27:
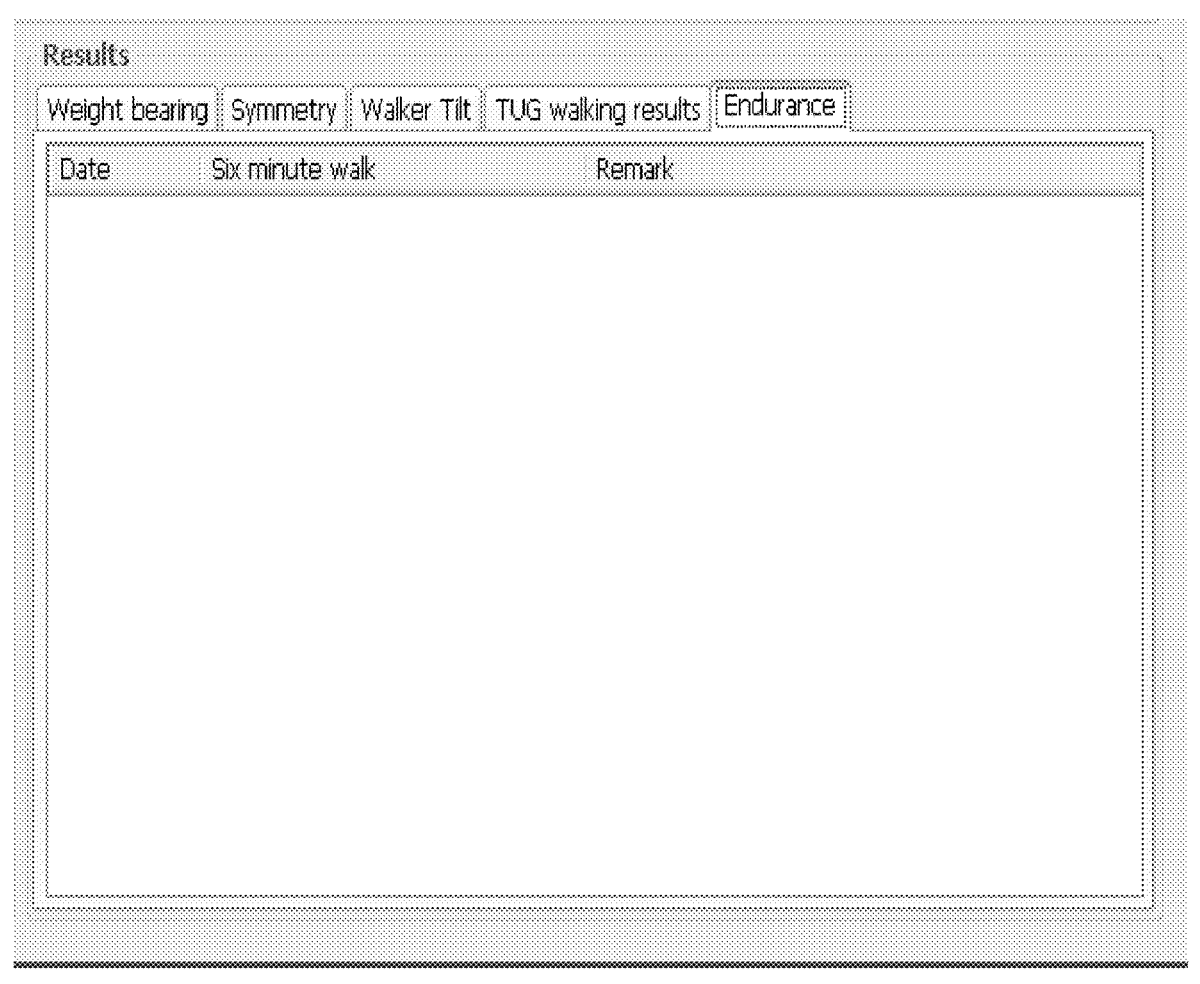

FIG. 24 is screen shot of a main menu of activities and selections, according to some embodiments. Optionally, choices on the main menu include "view reports," "download data from walker-assist device," "begin work" and "general settings." FIGS. 25A-B and 26-27 are exemplary screen shots which appear after clicking on respective tabs labeled symmetry, tilting, TUG results, and stamina in the screen shown in FIG. 24, according to some embodiments.

Begin Work

FIG. 28 is a sample screen shot of choice of a parameters screen, according to some embodiments. If "begin work" is selected on the main menu screen, the choice of parameters screen appears providing a choice between, for example, clinical or outdoor use.

Determining Load Thresholds

The screen shot of FIG. 28 is also a determination of load thresholds screen, according to some embodiments. Prompts request the input of the "General Permitted Load (w)" and the "Permitted Difference in Right/Left Load (x)".

Determining Tilt Thresholds

The screen shot of FIG. 28 is also a screen shot of a determination of tilt thresholds screen, according to some embodiments. Prompts request the input of the "Tilt Permitted" in the "left", "right", "forward" and "backward" directions.

Confirmation of Thresholds

After the load threshold information and tilt threshold information have been input, "cancel," or "confirm" may be selected. Selecting "cancel" erases any selections already made and resets the choice of load thresholds screen. Selecting "confirm" automatically enters the load and tilt threshold entries that were made and causes a confirmation of thresholds screen to appear.

General Settings

Figure 29:
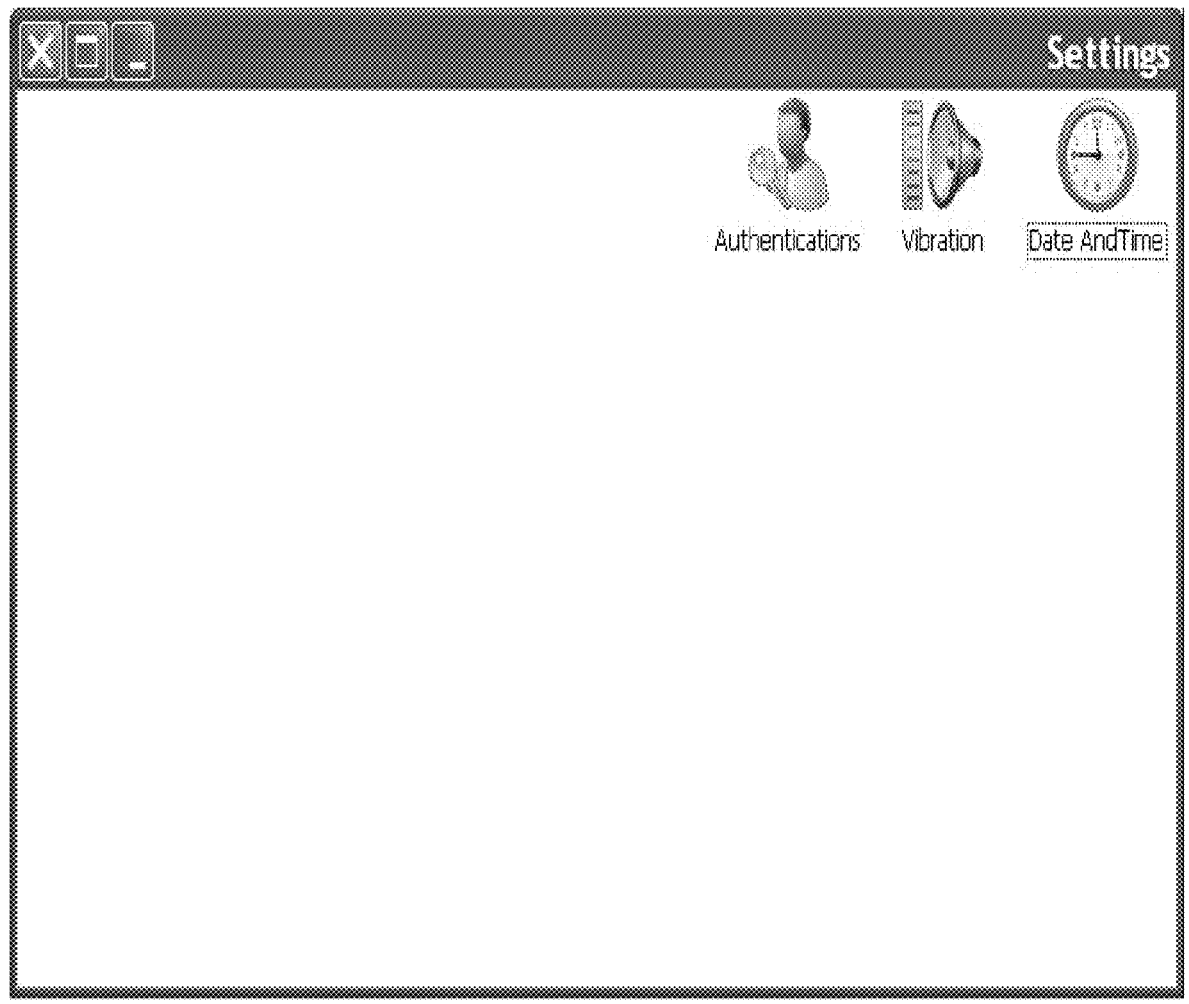
FIG. 29 is a screen shot of a determination of general settings screen, according to some embodiments of the invention.

FIG. 29 is a screen shot of a determination of general settings screen, according to some embodiments. If "general settings" is selected on the main menu screen (FIG. 24), the determination of general settings screen appears providing the choices of setting "Passwords," "Volume and/or Vibration Strength," and "Time and Date." Optionally, there are additionally provided choices of "Display" and "On and Off." When one of these choices is selected, a new screen appears providing choices for choosing settings in the chosen category. Optionally, the only general setting which may be selected is "Passwords."

Time and Date Settings

Figure 30:
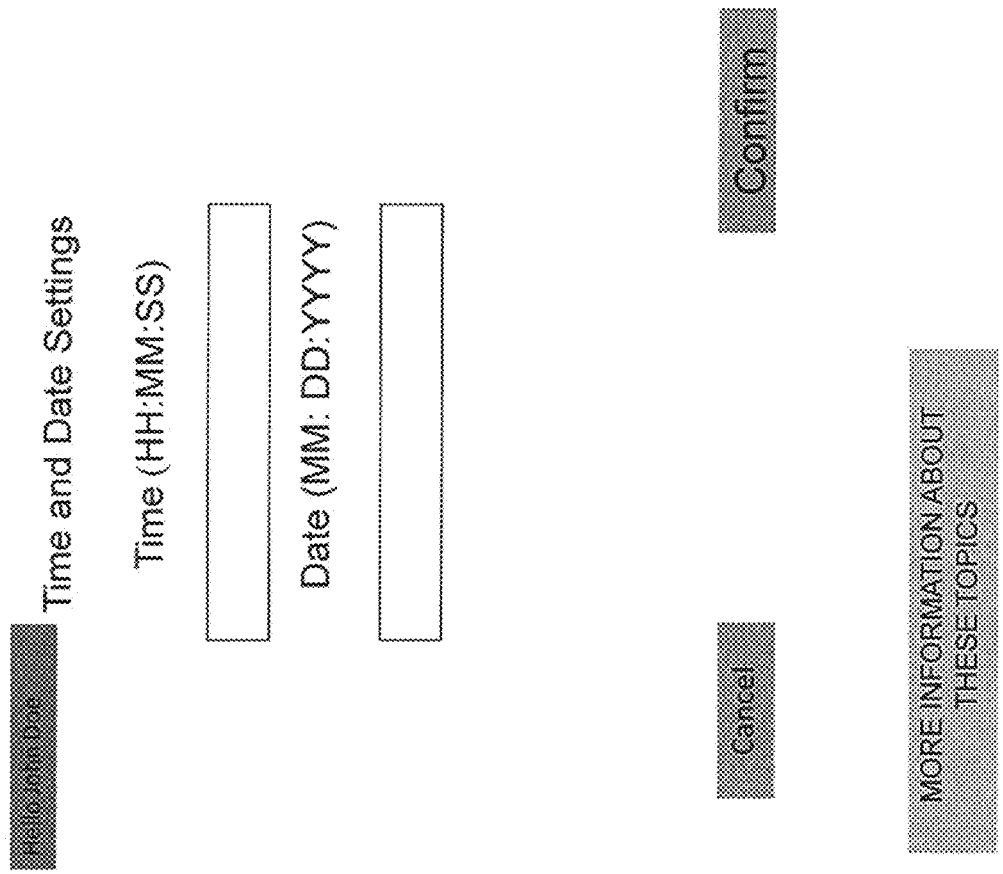
FIG. 30 is a screen shot of a determination of Time and Date settings screen, according to some embodiments of the invention.

FIG. 30 is a screen shot of a determination of Time and Date settings screen, according to some embodiments. This screen appears when "Time and Date" is selected in the "general settings" screen.

Prompts appear for the input of the current Time ("HH:MM:SS") and the current date ("MM:DD:YYYY"). In addition to these prompts, a prompt appears for "more information about these topics" and a "Hello" prompt appears on the left side of the screen.

After inputting time and date entries, "cancel," or "confirm" may be selected. Selecting "cancel" erases any selections already made and resets the choice of date and time. Selecting "confirm" automatically enters the date and time entries that were made and returns the user to the "general settings" screen.

Display Settings

Figure 31:
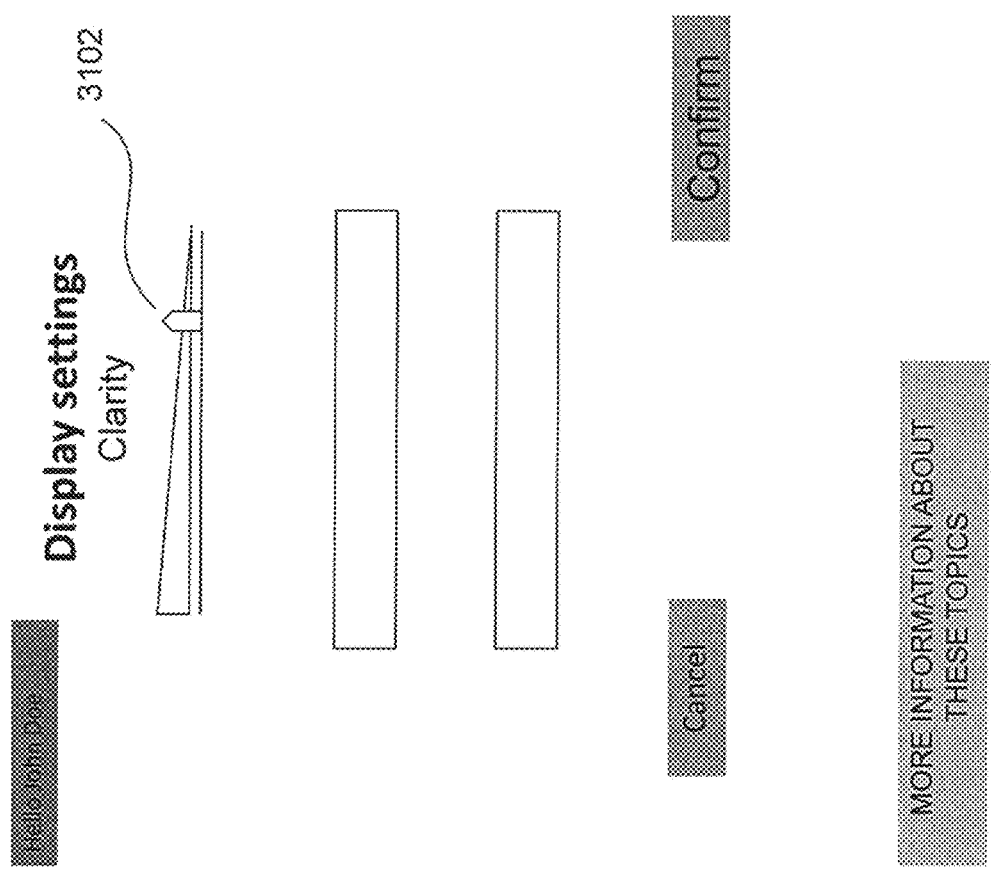
FIG. 31 is a screen shot of a determination of Display Settings screen, according to some embodiments of the invention.

FIG. 31 is a screen shot of a determination of Display Settings screen, according to some embodiments. This screen appears when "Display" is selected in the "general settings" screen.

A moveable selection marker/slider 3102 may be adjusted to increase the clarity of the items displayed in this screen. In addition to these prompts, the above described "more information" and "Hello" prompts appear on the left side of the screen.

After adjusting the slider 3102, "cancel," or "confirm" may be selected. Selecting "cancel" erases any selections already made and resets the choice of display settings. Selecting "confirm" automatically enters the display setting entry that was made and returns the user to the "general settings" screen.

Volume and Vibration Strength

Figure 32:
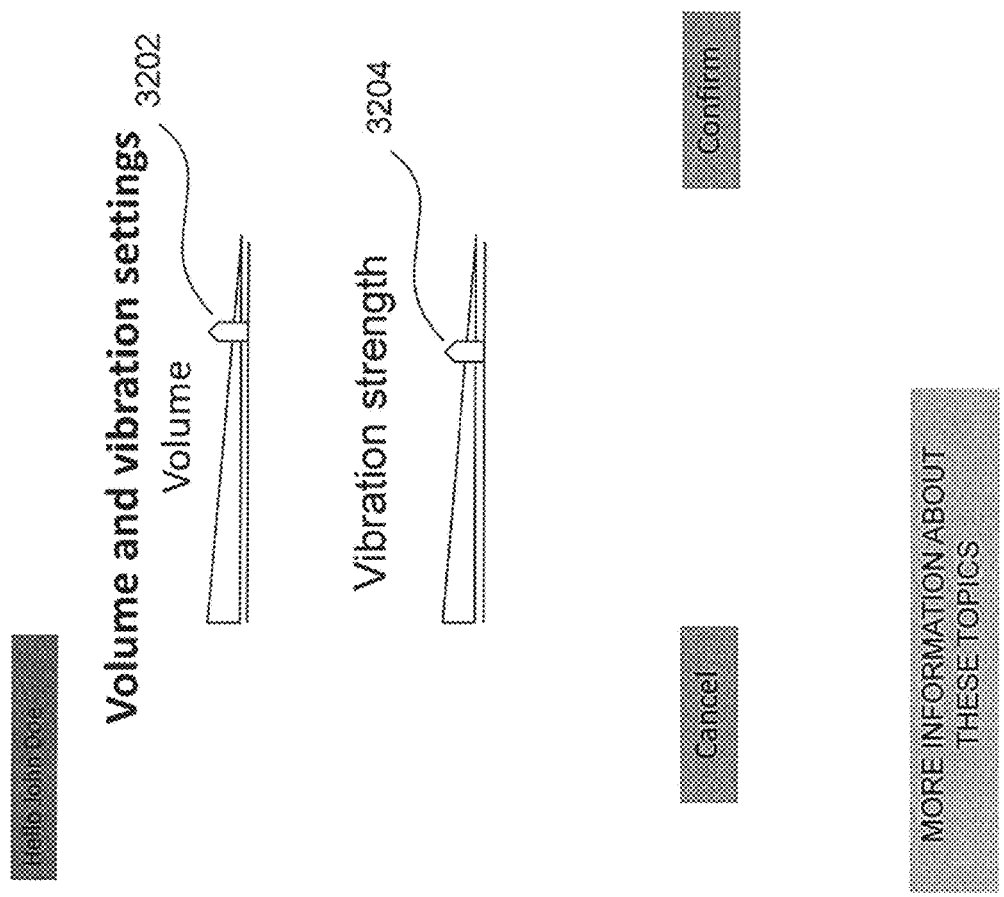
FIG. 32 is a screen shot of a determination of Volume and Vibration Strength Settings screen, according to some embodiments of the invention.

FIG. 32 is a screen shot of a determination of Volume and Vibration Strength Settings screen, according to some embodiments. This screen appears when "Volume and Vibration Strength" is selected in the "general settings" screen.

A moveable selection marker/slider 3202 may be adjusted to increase the volume setting. A moveable selection marker/slider 3204 may be adjusted to increase the vibration strength. In addition to these prompts, the above described "more information" and "Hello" prompts appear on the left side of the screen.

After adjusting the sliders 3202 and 3204, "cancel," or "confirm" may be selected. Selecting "cancel" erases any selections already made and resets the choice of volume and vibration strength settings. Selecting "confirm" automatically enters the volume and vibration strength setting entries that were made and returns the user to the "general settings" screen.

On and Off Settings

Figure 33:
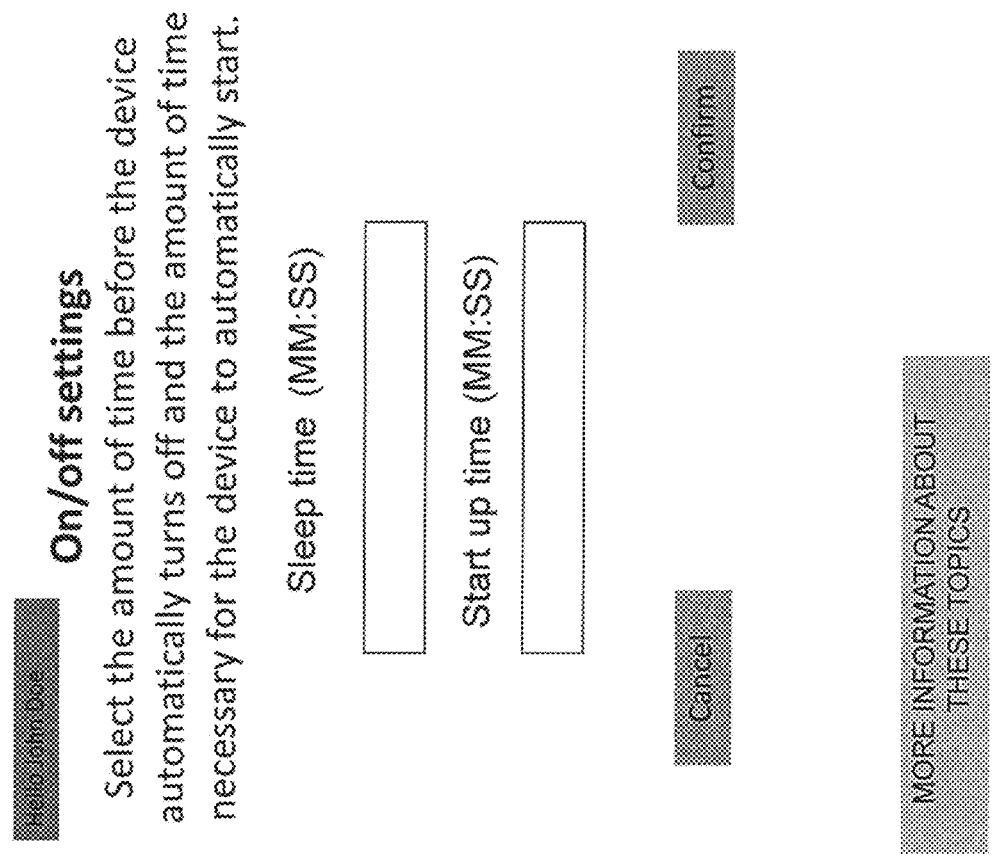
FIG. 33 is a screen shot of a determination of On and Off Settings screen, according to some embodiments of the invention.

FIG. 33 is a screen shot of a determination of On and Off Settings screen, according to some embodiments. This screen appears when "Turning On and Off" is selected in the "general settings" screen.

Prompts appear for the input of the Sleep Time ("MM:SS") that elapses before the walker-assist device automatically turns off during non-use (no movement of load) and the Start Up Time ("MM:SS") that elapses before the walker-assist device automatically starts when being moved without the device having been turned on. In addition to these prompts, the above described "more information" and "Hello" prompts appear on the left side of the screen.

After inputting Sleep Time and Start Up Time entries, "cancel," or "confirm" may be selected. Selecting "cancel" erases any selections already made and resets the choice of Sleep Time and Start Up Time. Selecting "confirm" automatically enters the date and time entries that were made and returns the user to the "general settings" screen.

Optionally, there are no On/Off Settings selectable from the general settings screen (FIG. 29). Instead, there may be a default whereby the walker-assist device automatically turns off after a predetermined amount of time without activity (load or movement) and whereby the walker-assist device automatically starts up when activity is sensed. Additionally, there may be a sensor for complete shutdown of the walker-assist device.

View Reports

FIG. 34 is a screen shot of a patient progress report shown in graph form, according to some embodiments. Variability in weight-bearing symmetry and balance throughout the treatment is shown in two graphs. In one (upper) graph, weight-bearing symmetry is represented on the y-axis and treatment session (for example, first, second, third) is represented on the x-axis. Two different lines (solid and dashed) are represented on the graph: W, for the measured total load, and X, for the measured difference in load measured on the right and left sides.

In a second (lower) graph, duration of activity (in minutes) is represented on the y-axis and treatment session (for example, first, second, third) is represented on the x-axis. Two different lines (solid and dashed) are represented on the graph: W, for the measured total load, and X, for the difference in load measured on the right and left sides.

In both graphs, the value shown for each treatment is the average obtained from all measurements taken on the day of that treatment.

Displaying Data

FIG. 35 is a screen shot of patient data summarizing measured right and left load levels, according to some embodiments. A table is displayed in which the date of the last five treatment sessions is listed. For each treatment session, XL (the load measured on the left side) and XR (the load measured on the right side) are listed.

When measured right and left load levels are displayed, "return to main menu" or "return to previous screen" may be selected. When "return to menu" is selected, the main menu screen is shown. When "return to previous screen" is selected, the previous screen is shown.

FIG. 36 is a screen shot of patient data summarizing activity levels achieved, according to some embodiments. A table is displayed in which the date of the last four treatment sessions is listed. For each treatment session, the activity level for the six minute session is listed, wherein the activity level is associated with the stamina of a patient. As distance traveled is a good measure of activity, for the purposes of this parameter, activity level is estimated by an acceleration sensor, instead of a pedometer.

When activity levels are displayed, "return to main menu" or "return to previous screen" may be selected. When "return to menu" is selected, the main menu screen is shown. When "return to previous screen" is selected, the previous screen is shown.

FIG. 37 is a screen shot of patient data summarizing TUG test results, according to some embodiments. A table is displayed in which the date of the last five treatment sessions is listed. For each treatment session, the duration of activities, W, X, F1, F2, F3 and F4 are listed.

W represents the actual measured total load, in Kg; X represents the actual measured difference in load between the right side and the left side, in Kg; F1 represents the actual tilt to the right, in degrees; F2 represents the actual tilt to the left, in degrees; F3 represents the actual tilt forward, in degrees; and F4 represents the actual tilt backward, in degrees.

When TUG test results are displayed, "return to main menu" or "return to previous screen" may be selected. When "return to menu" is selected, the main menu screen is shown. When "return to previous screen" is selected, the previous screen is shown.

Home Therapy Plan

FIG. 38 is a screen shot of a home therapy program plan, according to some embodiments. A table is displayed in which the date of the next five six-minute treatment sessions is listed. For each treatment session, the activity or activities planned for those six minute sessions is/are listed, as well as thresholds for W, the measured total load; and X, the difference in load measured on the right and left sides.

When the home therapy program plan is displayed, "print", "return to main menu" or "return to previous screen" may be selected. When "print" is selected, the table displayed on the screen is printed at the printer selected by the walker-assist device. If no printer is selected, a prompt will ask for a printer selection. After the print command is sent, "print" may be selected again, or "return to menu" or "return to previous screen" may be selected.

When "return to main menu" is selected, the main menu screen is shown. When "return to previous screen" is selected, the previous screen is shown.

It is expected that during the life of a patent maturing from this application many relevant walker-assist devices will be developed and the scope of the term walker-assist device is intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The present invention may be especially useful in the rehabilitation of patients who have suffered bone fractures or who have undergone elective surgery of the lower limbs.

Such rehabilitation utilizing the walker-assist device may include simple walking; exercises involving movement from a standing position to a sitting position and vice versa; and walking exercises along a specific path such as, for example, around obstacles. Rehabilitation protocol may include a series of exercise periods per day having predetermined exercise periods separated by rest periods of predetermined length(s), in accordance with the ability of each patient. Parameters to be measured may include distance walked continuously each day, for each day of a rehabilitation period; and time of walking continuously each day, for each day of the rehabilitation period. Additional measurements made may include the amount of load applied to hands during walking of a fixed distance, the amount of symmetry of load distribution during walking of a fixed distance, TUG test time and number of tilts of the walker, and activity level during a fixed period of time.

Such rehabilitation should be performed under the supervision of a qualified professional such as, for example, a physiotherapist or physician, and may aid in the strengthening of functioning muscles and in the improvement of range of motion. Additional benefits of the walker-assist device may include a reduction in the number of falls, a reduction in pain, and an increase in self-confidence while walking while experiencing pain. Such pain may be measured by a during rest periods, while walking, five minutes after walking, and during the night.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for monitoring the use of a walker comprising:
    at least one sensor adapted for retrofitting to a walker, for measuring a physical parameter at at least one location on the walker and for sending at least one feedback signal indicating a value of the physical parameter measured;
    wherein said at least one feedback signal provides guidance including at least one adjustment for a user who uses the walker for physical support to make in his use of the walker and wherein said guidance includes at least one of the following:
instructing a user to shift some of his weight from a first hand grip to a second hand grip; and
instructing said user to adjust his gait in a specific manner while not changing a direction of walking, said instruction is in accordance with an amount of pressure/force applied on each of said hand grips.

2. The system of claim 1, further comprising:
a computerized processor configured to receive said at least one signal indicating the value of the physical parameter measured from said at least one sensor, to analyze said at least one signal, and to provide a feedback signal to at least one of a user of the walker and a third party monitor of said user of the walker; and
a memory coupled to said computerized processor.

3. The system of claim 1 in which said physical parameter is at least one of a step length, swing/stance, duration and base of support.

4. The system of claim 1, wherein the walker includes at least one of at least one handle and wheels and wherein said the at least one location includes at least one of the at least one handle and the wheels of the walker.

5. The system of claim 1 in which said at least one sensor includes at least one of a mechanical sensor, an electromechanical sensor, and an electro-optical sensor.

6. The system of claim 1, in which at least one connector fastens said system for monitoring the use of a walker to the walker.

7. The system of claim 6, in which said at least one connector fastens said system for monitoring the use of a walker to the walker without at least one of a need to disassemble the walker, a need to disassemble said system for monitoring the use of a walker, a need for a technician and a need for tools.

8. The system of claim 6, in which said system for monitoring the use of a walker comprises a flexible joint bendable to the shape of a top portion of said walker.

9. The system of claim 1, in which said at least one signal is provided instantly.

10. The system of claim 1, in which:
said at least one sensor comprises one of a pressure sensor and a force sensor;
said measuring a physical parameter comprises measuring one of pressure and force of a hand upon at least one hand grip; and
the analysis of said at least one signal comprises comparing the values of the one of pressure and force measured with values in a table or threshold values.

11. The system of claim 1, further comprising an accelerometer configured to measure at least one of movement and acceleration of the walker along a longitudinal axis, a lateral axis and a vertical axis about the walker's center of mass.

12. The system of claim 11, wherein said accelerometer is comprised in a portable communication device.

13. The system of claim 1, further comprising a GPS monitor measuring the walker's location over time.

14. The system of claim 13, wherein said GPS monitor is comprised in a portable communication device.

15. The system of claim 1, wherein a portable communication device transmits said at least one feedback signal.

16. The system of claim 1, wherein said at least one feedback signal is provided through vibration of at least one part of a frame of the walker.

17. The system of claim 1, wherein said at least one feedback signal is provided on a display screen located in view of the user, and wherein said display screen is an integral part of said system.

18. The system of claim 1, wherein said at least one feedback signal is provided on a display screen located in view of the user, wherein said display screen is comprised in a portable communication device attached to dock, wherein said dock is an integral part of said system.

19. The system of claim 1, wherein an alert signal is provided when at least an increased risk of a user of the walker falling is detected.

20. The system of claim 1, wherein data collected by said system is analyzed to create guidelines for a patient's rehabilitation.

21. The system of claim 1, further comprising a processor is configured to determine the degree to which the user is tilting to a side.

22. The system of claim 1, wherein said at least one feedback signal is an indication of imbalance of the user of the walker.

23. The system of claim 1, wherein said at least one feedback signal provides guidance including instructing a user to adjust his gain in a specific manner, including at least one of:
instructing a user to move a foot forward, instructing a user to take a predetermined number of steps, instructing a user to walk a predetermined distance, instructing a user to walk for a predetermined duration of time, instructing a user to walk in a predetermined direction, instructing a user to place at least one of one of his feet and the walker at a predetermined location with at least one of a predetermined frequency and a predetermined duration, and instructing a user to stabilize his gait.

24. The system of claim 1, wherein said physical parameter is processed to determine asymmetry between hands of the user of the walker.

* * * * *